US006107275A

United States Patent [19]
Harbeson et al.

[11] Patent Number: 6,107,275
[45] Date of Patent: Aug. 22, 2000

[54] CYCLIC ANTIPLATELET PEPTIDES WITH PSEUDO-BOND

[75] Inventors: Scott L. Harbeson, Cambridge, Mass.; Alan J. Bitonti, Maineville, Ohio

[73] Assignee: Merrell Pharmaceuticals Inc., Bridgewater, N.J.

[21] Appl. No.: 08/835,274

[22] Filed: Apr. 9, 1997

Related U.S. Application Data

[63] Continuation of application No. 08/645,936, May 14, 1996, which is a continuation of application No. 08/228,177, Apr. 15, 1994, abandoned, which is a continuation of application No. 08/056,111, May 7, 1993, abandoned, which is a continuation-in-part of application No. 07/894,214, Jun. 4, 1992, abandoned.

[51] Int. Cl.$^7$ .............................. A61K 38/12; C07K 5/12
[52] U.S. Cl. ................................ 514/11; 514/9; 514/2; 530/317; 530/330
[58] Field of Search ................... 514/11, 9, 2; 530/317, 530/330

[56] References Cited

U.S. PATENT DOCUMENTS

| | | | |
|---|---|---|---|
| 4,242,256 | 12/1980 | Sharpe et al. | 260/112.5 |
| 5,023,233 | 6/1991 | Nutt et al. | 514/11 |
| 5,041,380 | 8/1991 | Ruoslahti et al. | 435/240.2 |

FOREIGN PATENT DOCUMENTS

| | | |
|---|---|---|
| 0410540 | 7/1990 | European Pat. Off. . |
| 0410541 | 7/1990 | European Pat. Off. . |
| 9015620 | 12/1990 | WIPO . |
| 9101331 | 2/1991 | WIPO . |
| WO910133 | 2/1991 | WIPO . |
| 9200995 | 1/1992 | WIPO . |

OTHER PUBLICATIONS

Nicholson et al., "In Vitro and In Vivo Effects of a peptide mimetic (SC–47643) of RGD as an antiplatelet and antithrombotic agent", *Thrombosis Research* 62; pp. 567–578, (1991).

Peishoff et al., "Investigation of Conformational Specificity at GPllb/llla: Evaluation of Conformationally Constrained RGD Peptides", *J. Med. Chem.* 35, pp. 3962–3969, (1992).

Barker, et al, "Cyclic RGD Peptide Analogues as Antiplatelet Antithrombotics", *J. Med. Chem.* 35, pp. 2040–2048, (1992).

Plow et al, "Cellular Adhesion: GPlla as a Prototypic Adhesion Receptor", *Prog. Heamost. Thromb.* 9, pp. 117–154, (1989).

Imura, et al., "Synergistic Antighrombotic Properties of G4124, a RGD–Containing Synthetic Peptide, and Argatroban, a Synthetic Thrombin Inhibitor, in a Hamster Femoral Vein Platelet–Rich Thrombosis Model", *Thrombosis and Haemostasis 68*, pp. 336–340 (1992).

Marguerie et al., "Human Platelets Possess an Inducible and Saturable Receptor Specific for Fibrogen" *The Journal of Biological Chemistry*, vol. 254, pp. 5357–5363, (1979).

Plow et al., "Arginyl–Clycyl–Aspartic Acid Sequences and Fibrinogen Binding to Platelets" *Blood*, vol. 70, pp. 110–115, (1987).

Ruoslahti et al., "New Perspectives in Cell Adhesion: RGD and Integrins" *Science* vol. 238, pp. 491–497, (1987).

Yamada, Kenneth M., "Adhesive Recognition Sequences", *The Journal of Biological Chemistry*, vol. 266, No. 20, pp. 12809–12812, (1991).

Spatola et al., *Biopolymers*, vol. 25, S229–S244 (1986).

Derwent Abstract 91–030930/05 of EP 410 539.

Derwent Abstract 91–030928/05 of EP 410 537.

Collen et al, "Fibrin–Specific Thrombolyc Agents and New Approaches to Coronary Arterial Thrombolysis" *Thrombolysis in Cardiovascular Disease* pp. 45–67.

Pierschbacher et al., "Influence of Stereochemistry of the Sequence Arg–Gly–Asp–Xaa on Binding Specificity in Cell Adhesion", *The Journal of Biological chemistry*, vol. 262 No. 36 pp. 17294–17298, (19870.

Spatola et al, *Tetrahedron*, vol. 44, No. 3, pp. 821–833, (1988).

Sasaki et al, *J. Med. Chem.*, vol. 30, pp. 1162–1166, (1987).

*Primary Examiner*—Keith D. MacMillan
*Assistant Examiner*—T. D. Wessendorf
*Attorney, Agent, or Firm*—T. Helen Payne

[57] ABSTRACT

The present invention relates to cyclic peptide analogs containing a pseudo-bond, useful as platelet aggregation inhibitors. An example of a compound of this invention includes Cyclo[AlaΨ[CH$_2$NH]-Arg-Gly-Asp-δ-Glu] (NHBn)•CF$_3$CO$_2$H. These compounds inhibit the binding of fibrinogen to the platelet GPIIb-IIIa integrin receptor which inhibits platelet aggregation and therefore these compounds act as potent antithrombotics.

11 Claims, No Drawings

CYCLIC ANTIPLATELET PEPTIDES WITH PSEUDO-BOND

This is a continuation of application Ser. No. 08/645,936, filed May 14, 1996, which is a Continuation of Ser. No. 08/228,177, filed Apr. 15, 1994, now abandoned, which is a Continuation of Ser. No. 08/056,111 filed May 7, 1993, now abandoned, which is a Continuation In Part of Ser. No. 07/894,214, filed Jun. 4, 1992, now abandoned.

FIELD OF THE INVENTION

The present invention relates to conformationally restrained peptide analogs as platelet aggregation inhibitors. These compounds inhibit the binding of fibrinogen to the platelet GPIIb-IIIa integrin receptor which inhibits platelet aggregation and therefore these compounds act as potent antithrombotics.

BACKGROUND OF THE INVENTION

Platelets occur in whole blood and are an integral component of thrombus formation and blood coagulation. Glycoprotein IIb-IIIa, a member of the integrin superfamily, is found on the platelet surface and participates in platelet function by interacting with proteins such as fibrinogen, which contain the amino acid sequence Arg-Gly-Asp. Various factors activate the GPIIb-IIIa receptor allowing interaction with fibrinogen and stimulating platelet aggregation and thrombus formation. A compound which blocks the interaction of GPIIb-IIIa with Arg-Gly-Asp containing peptides such as fibrinogen would antagonize platelet activation by any stimulus and would be an important anti-thrombotic agent.

Many disease states are characterized by blood vessel occlusion due to thrombus formation. Some of these thrombotic diseases are myocardial infarction, stroke, pulmonary embolism, deep vein thrombosis, peripheral arterial occlusion and coronary artery reocclusion following angioplasty. Patients whose blood flows over artificial surfaces are also at risk for thrombus formation. An agent which blocks platelet aggregation by inhibiting fibrinogen binding to the GPIIb-IIIa receptor should be useful in these hyperthrombotic states.

This invention describes such an agent which is a peptide of varying length and contains the Arg-Gly-Asp sequence or an analog thereof and is conformationally restrained by cyclization of an amino acid residue side-chain onto a backbone ($CH_2NH$) amide bond replacement. The cyclization strategy described allows the preparation of a linear peptide of varying length containing a conformational restraint at the important Arg-Gly-Asp sequence. A combination of varying peptide length and localized conformational restraint will provide peptides with high platelet aggregation inhibiting activity.

SUMMARY OF THE INVENTION

Antiplatelet agents consisting of conformationally restrained peptide analogs having the following formula 1

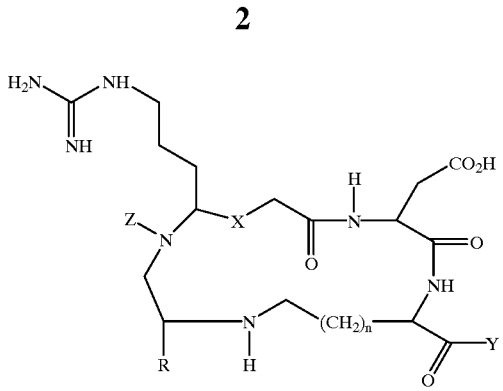

wherein
Y is a fragment —$A_1$—$A_2$—$A_3$—$NR_1R_2$ wherein
$A_1$ is a bond or an amino acid selected from the group consisting of Ser, Asp, Met, Trp, Phe or Ala; $A_2$ is a bond or an amino acid selected from the group consisting of Pro, Nle, Met, Leu, Asn, Asp, Val, Arg or Leu; $A_3$ is a bond or an amino acid selected from the group consisting of Ala, Asp, Pro or Asn and $R_1$ and $R_2$ are each independently hydrogen, $C_1$–$C_{10}$ alkyl, benzyl, indolyl, pyridinyl, or phenyl optionally substituted with 1 to 3 substituents selected from the group consisting of Cl, Br, $NO_2$, $NH_2$, OH or $OCH_3$;
Z is a fragment W—$A_6$—$A_5$—$A_4$— wherein
$A_4$ is a bond or an amino acid selected from the group consisting of Gly or βAla; $A_5$ is a bond or an amino acid selected from the group consisting of Arg, Lys, Thr, Ile, Leu, Phe, Asp, Asn or Val; $A_6$ is a bond or an amino acid selected from the group consisting of Val, Lys, Arg, Asp, Asn or Ala and W is hydrogen, succinyl, $C_1$–$C_{10}$ acyl, $C_1$–$C_{10}$ alkyl, —$(CH_2)_mC_6H_5$ wherein m is an integer 1–3, or —$(CH_2)_pCO_2H$ wherein p is an integer 1–4;
X is CONH, $CH_2NH$, $COCH_2$, $CH_2CH_2$, —$CH_2O$— or —CH=CH—;
R is hydrogen, $C_1$–$C_{10}$ alkyl, benzyl, indolyl, naphthyl, thienyl, p-HO-benzyl, p-$NO_2$-benzyl, p-Cl-benzyl; and p-$NH_2$-benzyl; and
n is an integer 1–3,
with the proviso that when either of $A_6$, $A_5$ and $A_4$ are amino acids, W is not $C_1$–$C_{10}$ alkyl, —$(CH_2)_mC_6H_5$ or —$(CH_2)_p$ $CO_2H$, or a pharmaceutically acceptable salt thereof.

These conformationally restrained peptide analogs and their pharmaceutical compositions are useful as antithrombotic agents.

DETAILED DESCRIPTION OF THE INVENTION

The term "$C_1$–$C_{10}$ alkyl" refers to a straight or branched alkyl of from 1 to 10 carbon atoms such as methyl, ethyl, propyl, isopropyl, butyl, isobutyl, tert-butyl, pentyl, isopentyl, sec-pentyl, hexyl, isohexyl, heptyl, octyl, nonyl, or decyl. The term "$C_1$–$C_{10}$ acyl" refers to a straight or branched acyl group of from 1–10 carbon atoms such as acetyl, propionyl, butyryl, valeryl, hexanoyl, heptanoyl, octanoyl, nonanoyl, decanoyl and the like.

The following common abbreviations of the naturally occurring amino acids are used throughout this specification:
Ala—alanine
Arg—arginine
Gly—glycine
Asp—aspartic acid Glu—glutamic acid
Leu—leucine
Trp—tryptophan
Ser—serine
Met—methionine
Phe—phenylalanine
Pro—proline
Nle—norleucine
Asn—asparagine
Val—valine
βAla—beta alanine
Lys—lysine
Ile—isoleucine The following common abbreviations of various protecting groups are used throughout this specification:
Boc=t-butyloxycarbonyl
Bn=benzyl
Chxl=cyclohexyl
Tos or Tosyl=p-toluenesulfonyl
Cbz=carbobenzyloxy
Ac=acetyl
Suc=succinyl
TFA=trifluoroacetic acid
$C_6H_5$=unsubstituted phenyl The α-amino protecting group employed with each amino acid introduced into the peptide sequence may be any such protecting group known in the art. Among the classes of—amino protecting groups contemplated are (1) acyl type protecting groups such as: formyl, trifluoroacetyl, phthalyl, toluenesulfonyl (Tos or tosyl), benzenesulfonyl, nitrophenylsulfenyl, tritylsulfenyl, o-nitrophenoxyacetyl and α-chlorobutyryl; (2) aromatic urethane type protecting groups such as benzyloxycarbonyl and substituted benzyloxycarbonyl, such as p-chlorobenzyloxycarbonyl, p-nitrobenzyloxycarbonyl, p-bromobenzyloxycarbonyl, p-methoxybenzyloxycarbonyl, 1-(p-biphenylyl)-1-methylethoxycarbonyl, α,α-dimethyl-3,5-dimethoxybenzyloxycarbonyl and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl (Boc).

Other nomenclature designations used to described the conformationally restrained peptide derivatives of this invention are Ψ[$CH_2NH$], Ψ[$COCH_2$], Ψ[$CH_2O$], Ψ[$CH_2CH_2$] and Ψ[erythro-CH=CH] wherein the symbol "Ψ" designates a modified peptide bond.

The natural amino acids, with the exception of glycine, contain a chiral carbon atom. Unless otherwise specifically indicated, the optically active amino acids, referred to herein, are of the L-configuration. The stereochemistry at the carbon atom bearing the R substituent is either the D- or L-configuration. As is customary, the structure of peptides written out herein is such that the amino terminal end is on the left side of the chain and the carboxy terminal end is on the right side of the chain.

Certain conformationally restrained peptides of formula 1 are preferred in the method of treating hyperthrombotic states. Applicants prefer those peptide derivatives of the formula 1 wherein X is CONH, $COCH_2$ or $CH_2CH_2$; those peptide derivatives wherein Y is benzylamine or Asp-$NH_2$; those peptide derivatives wherein n is 2, those peptide derivatives wherein R is $CH_3$, benzyl or p-OH-benzyl and those peptide derivatives wherein Z is succinyl, —$(CH_2)_3$ $CO_2H$ or $CH_3CO$-Asp-Gly-.

The peptide derivatives of the formula 1 can form pharmaceutically acceptable salts with any non-toxic, organic or inorganic acid. Illustrative inorganic acids which form suitable salts include hydrochloric, hydrobromic, sulphuric and phosphoric acid and acid metals salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic, trifluoromethane sulfonic and 2-hydroxyethane sulfonic acid.

As with any generic group of chemical compounds, certain groups are preferred. Applicants prefer those peptide derivatives of formula 1 wherein Z is H, Ph-$(CH_2)_3$—, $HO_2C$—$(CH_2)_3$—, or Ac-Asp-Gly-, X is —CONH—, —$COCH_2$—, or —$CH_2CH_2$—, Y is $NHCH_2Ph$ or Asp-$NH_2$, and R is —$CH_3$, —$CH_2Ph$ or 4—OH—$CH_2Ph$.

The conformationally restrained peptides of formula 1 wherein X is CONH can be prepared by one of ordinary skill in the art. A general synthetic procedure for preparing these compounds is set forth in Scheme A. In Scheme A, all substituents are as previously described unless otherwise indicated.

Scheme A

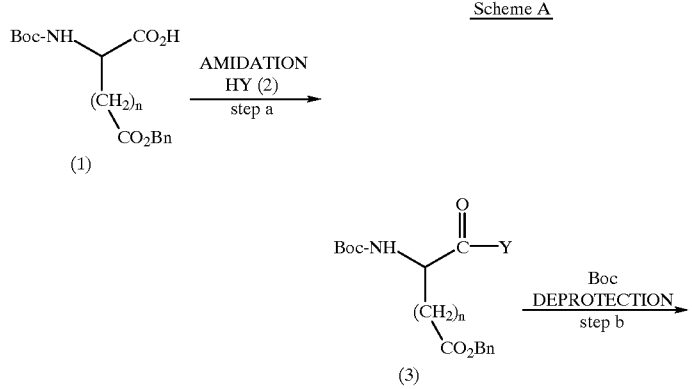

-continued
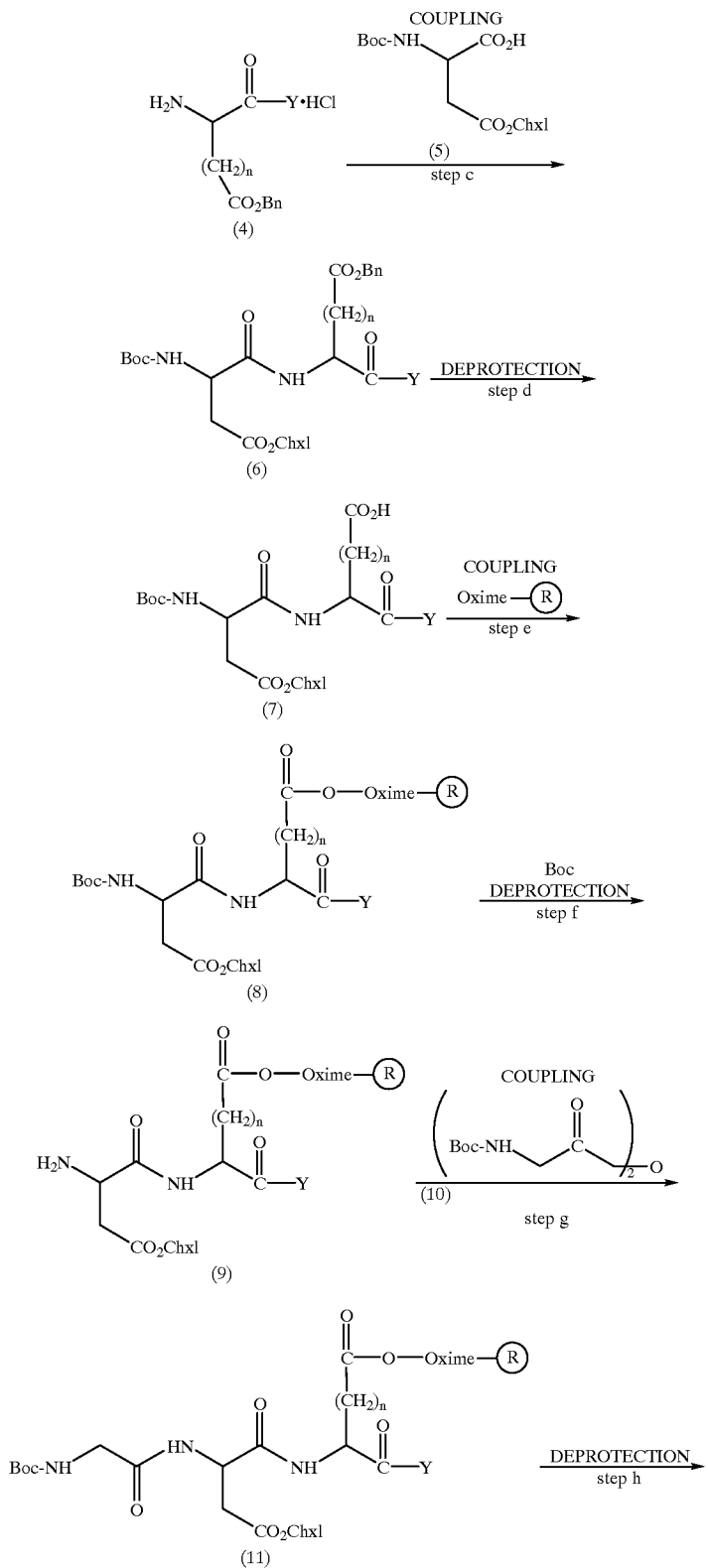

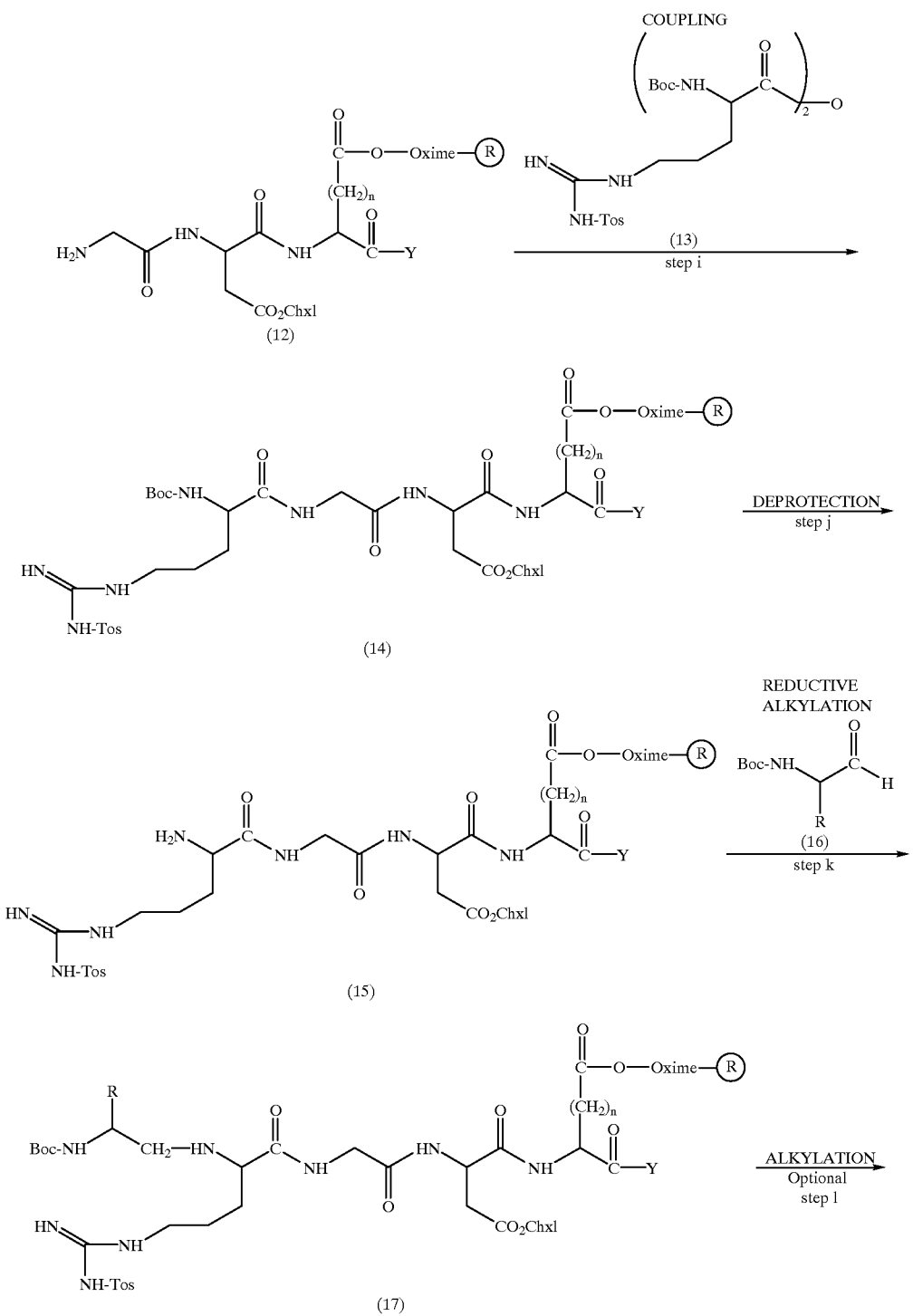

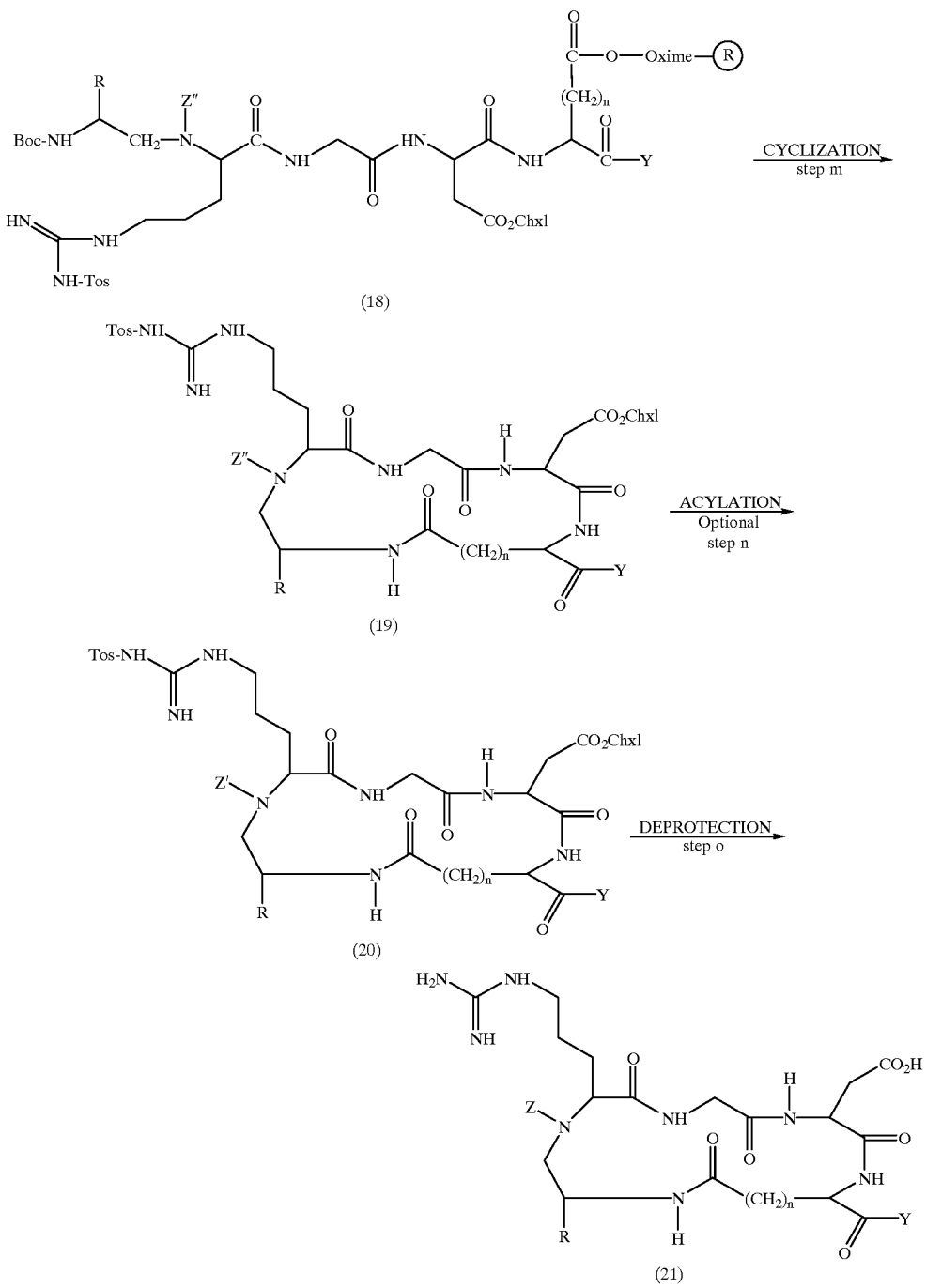

Z' = W—A_6—A_5—A_4— wherein W is $C_1$–$C_{10}$ acyl or succinyl
Z" = W—A_6—A_5—A_4— wherein W is hydrogen or $C_1$–$C_{10}$ alkyl,
—$(CH_2)_mC_6H_5$ or —$(CH_2)_pCO_2H$, m is an integer 1–3, p is
an integer 1–4 and $A_6$, $A_5$ and $A_4$ are bonds Scheme A provides a general synthetic procedure for preparing the compounds of formula 1 wherein X is $CONH_2$.

In step a, the appropriate N-Boc-amino(O-Bn) acid of structure (1) is amidated with the appropriate amine or peptide residue of structure (2) to give the corresponding N-Boc-amino(O-Bn) acid amide of structure (3). Examples of appropriate N-Boc amino(O-Bn) acid starting materials of structure (1) are Boc-Asp(β-Bn) (n=1), Boc-Glu(δ-Bn) (n=2) or $O^\epsilon$-Bn-$N^\alpha$-Boc-aminoadipic acid (n=3).

For example, the appropriate N-Boc-amino(O-Bn) acid of structure (1) is contacted with a molar equivalent of the appropriate amine or peptide residue of structure (2), a molar excess of an activating agent such as a mixture of 1-hydroxybenzotriazole hydrate and 1-(3-dimethylaminopropyl)-3-ethylcarbodiimide hydrochloride.

The reactants are typically contacted in a suitable organic solvent such as methylene chloride or tetrahydrofuran. The reactants are typically stirred together at room temperature for a period of time ranging from 5–24 hours. The N-Boc-amino(O-Bn) acid amide of structure (3) is recovered from the reaction zone by extractive procedures as is known in the art. It may be purified by chromatography.

The selection of an appropriate coupling reagent is within the skill of the art. Suitable coupling agents are (1) carbodiimides (e.g., N,N'-dicyclohexylcarbodiimide; (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Phe-O-Phe-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, 1–27 1970, which is incorporated herein by reference.

In step b, the N-Boc protecting group of the appropriate N-Boc-amino(O-Bn) acid amide of structure (3) is cleaved to give the corresponding amino(O-Bn) acid amide salt of structure (4).

For example, the appropriate N-Boc-amino(O-Bn) acid amide of structure (3) is contacted with a suitable acid, such as anhydrous hydrochloric acid or trifluoroacetic acid. The reactants are typically contacted in a suitable polar organic solvent such as dioxane. The reactants are typically stirred together at room temperature for a period of time ranging from 15 minutes to 4 hours. The amino(O-Bn) acid amide salt of structure (4) is recovered from the reaction zone by evaporation of the solvents. It may be purified by chromatography.

In step c, the appropriate amino(O-Bn) acid amide salt of structure (4) is coupled with N-Boc-Asp($\beta$-Chxl) of structure (5) to give the corresponding N-Boc-Asp($\beta$-Chxl)-amnio(O-Bn) acid amide of structure (6) as described previously in step a.

In step d, the benzyl protecting group of the appropriate N-Boc-Asp($\beta$-Chxl)-amino(O-Bn) acid amide of structure (6) is removed to give the corresponding N-Boc-Asp($\beta$-Chxl)-amino acid amide of structure (7).

For example, the appropriate N-Boc-Asp($\beta$-Chxl)-amino (O-Bn) acid amide of structure (6) is contacted with a catalytic amount of a suitable hydrogenation catalyst such as Perlman's catalyst. The reactants are typically contacted in a suitable protic organic solvent such as methanol. The reactants are typically subjected to hydrogenation at room temperature on a Paar Hydrogenation Apparatus for a period of time ranging from 2–24 hours. The N-Boc-Asp($\beta$-Chxl)-amino acid amide of structure (7) is recovered from the reaction zone by filtration and evaporation of the solvent. It may be purified by chromatography.

In step e, the appropriate N-Boc-Asp($\beta$-Chxl)-amino acid amide of structure (7) is coupled with oxime resin to give the corresponding N-Boc-Asp($\beta$-Chxl)-amino acid amide oxime resin of structure (8).

For example, the appropriate N-Boc-Asp($\beta$-Chxl)-amino acid amide of structure (7) is contacted with a molar excess of a suitable coupling agent such as 1,3-dicyclohexylcarbodiimide. The reactants are typically contacted in a suitable organic solvent such as methylene chloride or tetrahydrofuran. The reactants are typically stirred together at room temperature for a period of time ranging from 2–24 hours, filtered and stirred with a suitable capping mixture such as acetic anhydride:diisopropylethylamine:dimethylformamide (6:2:24) for a period of time ranging from 15 minutes to 10 hours.

The N-Boc-Asp($\beta$-Chxl)-amino acid amide oxime resin of structure (8) is recovered from the reaction zone by filtration.

In step f, the N-Boc protecting group of the appropriate N-Boc-Asp($\beta$-Chxl)-amino acid amide oxime resin of structure (8) is cleaved to give the corresponding Asp($\beta$-Chxl)-amino acid amide oxime resin of structure (9).

For example, the appropriate N-Boc-Asp($\beta$-Chxl)-amino acid amide oxime resin of structure (8) is contacted with a suitable acid such as trifluoroacetic acid with anisole. The reactants are typically contacted in a suitable organic solvent such as methylene chloride. The reactants are typically stirred together at room temperature for a period of time ranging from 10 minutes to 30 minutes. The Asp($\beta$-Chxl)-amino acid amide oxime resin of structure (9) is recovered from the reaction zone by filtration.

In step g, the appropriate Asp($\beta$-Chxl)-amino acid amide oxime resin of structure (9) is coupled with N-Boc-Gly symmetrical anhydride (10) to give the corresponding N-Boc-Gly-Asp($\beta$-Chxl)-amino acid amide oxime resin of structure (11).

For example, the appropriate Asp($\beta$-Chxl)-amino acid amide oxime resin of structure (9) is contacted with 2.5 molar equivalents of N-Boc-Gly symmetrical anhydride (10). The reactants are typically contacted in a suitable organic solvent such as dimethylformamide. The reactants are typically stirred together at room temperature for a period of time ranging from 1–12 hours, filtered and stirred with a suitable capping mixture such as acetic anhydride:diisopropylethylamine:dimethylformamide (6:2:24) for a period of time ranging from 15 minutes to 10 hour. The N-Boc-Gly-Asp($\beta$-Chxl)-amino acid amide oxime resin of structure (11) is recovered from the reaction zone by filtration.

In step h, the N-Boc protecting group of the appropriate N-Boc-Gly-Asp($\beta$-Chxl)-amino acid amide oxime resin of structure (11) is cleaved to give the corresponding Gly-Asp ($\beta$-Chxl)-amino acid amide oxime resin of structure (12) as described previously in step f.

In step i, the appropriate Gly-Asp($\beta$-Chxl)-amino acid amide oxime resin of structure (12) is coupled with N-Boc-Arg($N^g$-Tos) symmetrical anhydride (13) to give the corresponding N-Boc-Arg($N^g$-Tos)-Gly-Asp($\beta$-Chxl)-amino acid amide oxime resin of structure (14) as described previously in step g.

In step j, the N-Boc protecting group of the appropriate N-Boc-Arg($N^g$-Tos)-Gly-Asp($\beta$-Chxl)-amino acid amide oxime resin of structure (14) is cleaved to give the corresponding Arg($N^g$-Tos)-Gly-Asp($\beta$-Chxl)-amino acid amide oxime resin of structure (15) as described previously in step f.

In step k, the appropriate Arg($N^g$-Tos)-Gly-Asp($\beta$-Chxl)-amino acid amide oxime resin of structure (15) is coupled with the appropriate D or L-N-Boc-NHCHR-aldehyde of structure (16) to give the corresponding N-Boc-NHCHR-$\Psi$ [$CH_2NH$]-Arg($N^g$-Tos)-Gly-Asp($\beta$-Chxl)-amino acid amide oxime resin of structure (17).

For example, the appropriate Arg($N^g$-Tos)-Gly-Asp(β-Chxl)-amino acid amide oxime resin of structure (15) is contacted with 2.5 molar equivalents of the appropriate D or L-N-Boc-NHCHR-aldehyde of structure (16) and a molar equivalent of sodium cyanoborohydride. The reactants are typically stirred together at room temperature for a period of time ranging from 1–10 hours. The N-Boc-NHCHR-Ψ[CH$_2$NH]-Arg($N^g$-Tos)-Gly-Asp(β-Chxl)-amino acid amide oxime resin of structure (17) is recovered from the reaction zone by filtration and washing with solvent.

In optional step l, the Ψ[CH$_2$NH] functionality of the appropriate N-Boc-NHCHR-Ψ[CH$_2$NH]-Arg($N^g$-Tos)-Gly-Asp(β-Chxl)-amino acid amide oxime resin of structure (17) may be alkylated to give the corresponding N-Boc-NHCHR-Ψ[CH$_2$N(Z")]-Arg($N^g$-Tos)-Gly-Asp(β-Chxl)-amino acid amide oxime resin of structure (18) wherein Z" is W—A$_6$—A$_5$—A$_4$— wherein W is C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds as is well known in the art, such as reductive alkylation.

In step m, the appropriate N-Boc-NHCHR-Ψ[CH$_2$NH]-Arg($N^g$-Tos)-Gly-Asp(β-Chxl)-amino acid amide oxime resin of structure (17) or N-Boc-NHCHR-Ψ[CH$_2$N(Z")]-Arg($N^g$-Tos)-Gly-Asp(β-Chxl)-amino acid amide oxime resin of structure (18) wherein Z" is W—A$_6$—A$_5$—A$_4$— wherein W is C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds is cyclized to give the corresponding Cyclo[NHCHR-Ψ[CH$_2$N(Z")]-Arg($N^g$-Tos)-Gly-Asp(β-Chxl)-amino acid]amide of structure (19) wherein Z" is W—A$_6$—A$_5$—A$_4$— wherein W is hydrogen, C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds.

For example, the N-Boc of the appropriate N-Boc-NHCHR-Ψ[CH$_2$NH]-Arg($N^g$-Tos)-Gly-Asp(β-Chxl)-amino acid amide oxime resin of structure (17) or N-Boc-NHCHR-Ψ[CH$_2$N(Z")]-Arg($N^g$-Tos)-Gly-Asp(β-Chxl)-amino acid amide oxime resin of structure (18) wherein Z" is W—A$_6$—A$_5$—A$_4$— wherein W is C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds is first cleaved to give the corresponding intermediate NH$_2$CHR-Ψ[CH$_2$NH)-Arg($N^g$-Tos)-Gly-Asp(β-Chxl)-amino acid amide oxime resin or NH$_2$CHR-Ψ[CH$_2$N(Z')]-Arg($N^g$-Tos)-Gly-Asp(β-Chxl)-amino acid amide oxime resin wherein Z" is W—A$_6$—A$_5$—A$_4$— wherein W is C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds as described previously in step f.

The intermediate NH$_2$CHR-Ψ[CH$_2$NH]-Arg($N^g$-Tos)-Gly-Asp(β-Chxl)-amino acid amide oxime resin or NH$_2$CHR-Ψ[CH$_2$N(Z')]-Arg($N^g$-Tos)-Gly-Asp(β-Chxl)-amino acid amide oxime resin wherein Z" is W—A$_6$—A$_5$—A$_4$— wherein W is C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds is then cyclized and cleaved from the oxime resin by contacting with a suitable dilute acid, such as 1% acetic acid in dimethylformamide. The reactants are typically shaken together at room temperature for a period of time ranging from 2 hours to 2 days. The Cyclo[NHCHR-Ψ[CH$_2$N(Z")]-Arg($N^g$-Tos)-Gly-Asp(β-Chxl)-amino acid]amide of structure (19) wherein Z" is W—A$_6$—A$_5$—A$_4$— wherein W is hydrogen or C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds is recovered from the reaction zone by evaporation of the solvent. It may be purified by chromatography.

In optional step n, the appropriate Cyclo[NHCHR-Ψ[CH$_2$N(Z")]-Arg($N^g$-Tos)-Gly-Asp(β-Chxl)-amino acid] amide of structure (19) wherein Z" is W—A$_6$—A$_5$—A$_4$— wherein W is hydrogen and A$_6$, A$_5$ and A$_4$ are bonds may be acylated as is known in the art to give the corresponding Cyclo[NHCHR-Ψ[CH$_2$N(Z')]-Arg($N^g$-Tos)-Gly-Asp(β-Chxl)-amino acid]amide of structure (20) wherein Z' is W—A$_6$—A$_5$—A$_4$— wherein W is C$_1$–C$_{10}$ acyl or succinyl and A$_6$, A$_5$ and A$_4$ are bonds.

In addition, the appropriate Cyclo[NHCHR-Ψ[CH$_2$N(Z")]-Arg($N^g$-Tos)-Gly-Asp(β-Chxl)-amino acid]amide of structure (19) wherein Z" is W—A$_6$—A$_5$—A$_4$— wherein W is hydrogen and A$_6$, A$_5$ and A$_4$ are bonds may be converted to the corresponding Cyclo[NHCHR-Ψ[CH$_2$N(Z')]-Arg($N^g$-Tos)-Gly-Asp(β-Chxl)-amino acid]amide of structure (20) wherein Z' is W—A$_6$—A$_5$—A$_4$— wherein W is hydrogen and at least one of A$_6$, A$_5$ and A$_4$ is an amino acid by standard peptide chemistry as is known in the art. The terminal amino of the peptide side chain A$_6$—A$_5$—A$_4$ may then be acylated as is known in the art to give the corresponding Cyclo[NHCHR-Ψ[CH$_2$N(Z')]-Arg($N^g$-Tos)-Gly-Asp(β-Chxl)-amino acid]amide of structure (20) wherein Z' is W—A$_6$—A$_5$—A$_4$— wherein W is C$_1$–C$_{10}$ acyl or succinyl and at least one of A$_6$, A$_5$ and A$_4$ is an amino acid.

In step o, the protecting groups of the appropriate Cyclo[NHCHR-Ψ[CH$_2$N(Z")]-Arg($N^g$-Tos)-Gly-Asp(β-Chxl)-amino acid]amide of structure (19) wherein Z" is W—A$_6$—A$_5$—A$_4$— wherein W is hydrogen, C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds or the appropriate Cyclo[NHCHR-Ψ[CH$_2$N(Z)]-Arg($N^g$-Tos)-Gly-Asp(β-Chxl)-amino acid]amide of structure (20) wherein Z' is W—A$_6$—A$_5$—A$_4$— wherein W is hydrogen, C$_1$–C$_{10}$ acyl or succinyl and at least one of A$_6$, A$_5$ and A$_4$ is an amino acid are removed to give the corresponding Cyclo[NHCHR-Ψ[CH$_2$N(Z)]-Arg-Gly-Asp-amino acid] amide of structure (21).

For example, the appropriate Cyclo[NHCHR-Ψ[CH$_2$N(Z")]-Arg($N^g$-Tos)-Gly-Asp(β-Chxl)-amino acid]amide of structure (19) wherein Z" is W—A$_6$—A$_5$—A$_4$— wherein W is hydrogen, C$_1$–C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds or the appropriate Cyclo[NHCHR-Ψ[CH$_2$N(Z)]-Arg($N^g$-Tos)-Gly-Asp(β-Chxl)-amino acid]amide of structure (20) wherein Z' is W—A$_6$—A$_5$—A$_4$— wherein W is hydrogen, C$_1$–C$_{10}$ acyl or succinyl and at least one of A$_6$, A$_5$ and A$_4$ is an amino acid is contacted with hydrogen fluoride and and a suitable scavenger such as anisole. The reactants are typically stirred together at 0° C. for a period of time ranging from 20 minutes to 1 hour. The Cyclo[NHCHR-Ψ[CH$_2$N(Z)]-Arg-Gly-Asp-amino acid]amide of structure (21) is recovered from the reaction zone by evaporation of the solvent. It may be purified by chromatography.

Starting materials for use in Scheme A are readily available to one of ordinary skill in the art. For example, oxime resin is described in *J. Org. Chem.*, 45 1295–1300 1980.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "µL" refers to microliters; "µg" refers to micrograms; and "µM" refers to micromolar.

EXAMPLE 1

MDL-101,429KM

Cyclo[AlaΨ[CH$_2$NH]-Arg-Gly-Asp-δ-Glu](NHBn)
•CF$_3$CO$_2$H-SEQ ID NO: 1

Step a
Boc-Glu(δ-Bn)(NHBn)

Dissolve Boc-Glu(δ-Bn) (6.68 g, 19.8 mmol) in dichloromethane (40 mL) and add 1-hydroxybenzotriazole hydrate (3.4 g, 25.2 mmol), 1-(3-dimethylaminopropyl)3-ethylcarbodiimide hydrochloride (4.2 g, 21.9 mmol) and benzylamine (2.2 mL, 20 mmol). Stir at room temperature overnight and dilute with ethyl acetate (250 mL). Wash with 0.5N hydrochloric acid (3×80 mL), saturated sodium hydrogen carbonate (3×80 mL) and saturated sodium chloride (80 mL). Dry (MgSO$_4$), filter and evaporate the solvent in vacuo to give the title compound as a white crystalline solid (8.19 g, 97%).

Step b
Glu(δ-Bn)(NHBn) hydrochloride

Dissolve Boc-Glu(δ-Bn)(NHBn) (8.19 g, 19.2 mmol) in a solution of 4N hydrochloric acid in dioxane (40 mL). Stir at room temperature for 30 minutes and evaporate the solvent in vacuo to give the title compound as a brittle foam.

Step c
Boc-Asp(β-Chxl)-Glu(δ-Bn)(NHBn)

Dissolve Glu(δ-Bn)(NHBn) hydrochloride (19.2 mmol) in dimethylformamide (50 mL) and add 1-hydroxybenzotriazole hydrate (3.27 g, 21 mmol), Boc-Asp(β-Chxl) (6.04 g, 19.2 mmol), triethylamine (4.7 mL) and 1-(3-dimethylaminopropyl)3-ethylcarbodiimide hydrochloride (4.08 g, 21.3 mmol). Stir at room temperature overnight and dilute with ethyl acetate (300 mL). Wash with 0.5N hydrochloric acid (3×125 mL), saturated sodium hydrogen carbonate (3×100 mL), water (150 mL) and saturated sodium chloride (150 mL). Dry (MgSO$_4$), filter and evaporate the solvent in vacuo to give the title compound as a white crystalline solid (11.57 g, 97%).

Step d
Boc-Asp(β-Chxl)-Glu(NHBn)

Dissolve Boc-Asp(β-Chxl)-Glu(δ-Bn)(NHBn) (11.57 g, 18.6 mmol) in methanol (200 mL) and add Perlman's catalyst (200 mg). Hydrogenate on a Paar Hydrogenation Apparatus for 4 hours, filter through Celite filter aid and evaporate the solvent in vacuo to give the title compound as a brittle glass foam (10 g, 100%).

Step e
Boc-Asp(β-Chxl)-Glu(δ-oxime resin)(NHBn)

Dissolve Boc-Asp(β-Chxl)-Glu(NHBn) (10 g, 18.6 mmol) in methylene chloride (140 mL). Add oxime resin (21 g, 0.69 meq/g, 14.5 mmol) and a 0.5M solution of 1,3-dicyclohexylcarbodiimide in methylene chloride (42 mL, 21 mmol) and mix on a rotary evaporator for 20 hours. Filter, wash with dimethylformamide (2×200 mL), methylene chloride (200 mL), methanol (3×200 mL) and methylene chloride (3×200 mL). Suspend in a capping mixture of acetic anhydride:diisopropylethylamine:dimethylformamide (6:2:24) for 30 minutes. Filter and wash with dimethylformamide (2×200 mL), methanol (3×200 mL) and methylene chloride (3×200 mL). Dry in vacuo to give the title compound (26.3 g).

Step f
Asp(β-Chxl)-Glu(δ-oxime resin)(NHBn)

Briefly wash Boc-Asp(β-Chxl)-Glu(δ-oxime resin)(NHBn) (5.2 g, 2 mmol) with 50 mL of a solution of 25% trifluoroactic acid in methylene chloride with 1% anisole and filter. Treat with 50 mL of a solution of 25% trifluoroactic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step g
Boc-Gly-Asp(β-Chxl)-Glu(δ-oxime resin)(NHBn)

Mix Boc-Gly (2.1 g, 12 mmol), methylene chloride (12 mL) and add a 0.5M solution of 1,3-dicyclohexylcarbodiimide in methylene chloride (12 mL, 6 mmol). Stir at room temperature for 1 hour, filter and use the resulting Boc-Gly symmetrical anhydride as a solution.

Add Asp(β-Chxl)-Glu(δ-oxime resin)(NHBn) to the solution of Boc-Gly symmetrical anhydride. Stir at room temperature for 2 hours, filter and wash with dimethylformamide (2×50 mL). Suspend in a capping mixture of acetic anhydride:diisopropylethylamine:dimethylformamide (6:2:24) for 30 minutes. Filter, wash with dimethylformamide (3×50 mL), isopropanol (3×50 mL) and methylene chloride (2×50 mL). Dry in vacuo to give the title compound (5.15 g).

Step h
Gly-Asp(β-Chxl)-Glu(δ-oxime resin)(NHBn)

Briefly wash Boc-Gly-Asp(β-Chxl)-Glu(δ-oxime resin)(NHBn) (5.15 g) with 50 mL of a solution of 25% trifluoroactic acid in methylene chloride with 1% anisole and filter. Treat with 50 mL of a solution of 25% trifluoroactic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step i
N$^\alpha$-Boc-Arg(N$^g$-Tos)-Gly-Asp($\beta$-Chxl)-Glu($\delta$-oxime resin)(NHBn)-SEQ ID NO: 2

Suspend N$^\alpha$-Boc-Arg(N$^g$-Tos) (6.43 g, 15 mmol) in methylene chloride (15 mL) and add a 0.5M solution of 1,3-dicyclohexylcarbodiimide in methylene chloride (15 mL, 7.5 mmol) and dimethylformamide (4 mL). Stir at room temperature for 1 hour, filter and use the resulting N$^\alpha$-Boc-Arg(N$^g$-Tos) symmetrical anhydride as a solution.

Add Gly-Asp($\beta$-Chxl)-Glu($\delta$-oxime resin)(NHBn) to the solution of N$^\alpha$-Boc-Arg(N$^g$-Tos) symmetrical anhydride. Shake at room temperature for 3 hours, filter and wash with dimethylformamide (2×50 mL) and methylene chloride. Dry in vacuo to give the title compound (6.11 g).

Step j
Arg(N$^g$-Tos)-Gly-Asp($\beta$-Chxl)-Glu($\delta$-oxime resin)(NHBn)-SEQ ID NO: 3

Briefly wash N$^\alpha$-Boc-Arg(N$^g$-Tos)-Gly-Asp($\beta$-Chxl)-Glu ($\delta$-oxime resin)(NHBn)(SEQ ID NO: 2) (6.11 g) with 50 mL of a solution of 25% trifluoroactic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound (6 g).

Step k
Boc-Ala$\Psi$[CH$_2$NH]-Arg(N$^g$-Tos)-Gly-Asp($\beta$-Chxl)-Glu($\delta$-oxime resin)(NHBn)-SEQ ID NO: 4

Dissolve Boc-Ala (1.89 g, 10 mmol) in anhydrous tetrahydrofuran (30 mL) and add 1,1'-carbonyldiimidazole (1.8 g, 11 mmol). Stir for 30 minutes and add a solution of N,O-dimethylhydroxylamine hydrochloride (1.44 g, 15 mmol) in dimethylformamide (10 mL) and diisopropylethylamine (2.6 mL). Stir at room temperature overnight and dilute with ethyl acetate (150 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give Boc-Ala(NCH$_3$(OCH$_3$)) as a white crystalline solid (1.95 g, 84%); mp 148–149° C.

Anal. Calcd for C$_{10}$H$_{20}$N$_2$O$_4$: C, 51.71; H, 8.68; N, 12.06; Found: C, 52.07; H, 8.87; N, 12.00.

Dissolve Boc-Ala(NCH$_3$(OCH$_3$)) (1.16 g, 5 mmol) in anhydrous tetrahydrofuran (40 mL) and cool in an ice bath. Add a 1M solution of lithium aluminum hyride in tetrahydrofuran (3.1 mL) and stir for 40 minutes at 5° C. Quench with an aqueous solution of sodium hydrogen sulfate (0.75 g in 15 mL) and dilute with water (150 mL). Extract into ethyl acetate (3×40 mL), dry (MgSO$_4$) and evaporate the solvent in vacuo to give Boc-Ala-al as a white crystalline solid.

Dissolve Boc-Ala-al (5 mmol) in a solution of 1% acetic acid in dimethylformamide (10 mL). Add Arg(N$^g$-Tos)-Gly-Asp($\beta$-Chxl)-Glu($\delta$-oxime resin)(NHBn)(SEQ ID NO: 3) (1.5 g, 0.5 mmol) and sodium cyanoborohydride (150 mg). Shake for 2 hours and filter. Wash with dimethylformamide (3×20 mL), methylene chloride (3×20 mL) and collect by filtration to give the title compound (1.42 g).

Step m
Cyclo[Ala$\Psi$[CH$_2$NH]-Arg(N$^g$-Tos)-Gly-Asp($\beta$-Chxl)-$\delta$-Glu](NHBn)-SEQ ID NO: 5

Treat Boc-Ala$\Psi$[CH$_2$NH-Arg(N$^g$-Tos)-Gly-Asp($\beta$-Chxl)-Glu($\delta$-oxime resin)(NHBn) (SEQ ID NO: 4) (5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound (269 mg, 68%).

Step o
Cyclo[Ala$\Psi$[CH$_2$NH]-Arg-Gly-Asp-$\delta$-Glu](NHBn)·CF$_3$CO$_2$H-SEQ ID NO: 1

Suspend Cyclo[Ala$\Psi$[CH$_2$NH]-Arg(N$^g$-Tos)-Gly-Asp($\beta$-Chxl)-$\delta$-Glu]($\alpha$-NHBn) (SEQ ID NO: 5) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound (34.2 mg).

FAB MS: 604.2 (M+H.)$^+$

AAA: Asp, 0.98; Glu, 1.02; Gly, 0.86.

EXAMPLE 2

Cyclo[Ala$\Psi$[(CH$_2$N(CO(CH$_2$)$_2$CO$_2$H)]-Arg-Gly-Asp-$\delta$-Glu](NHBn)·CF$_3$CO$_2$H-SEQ ID NO: 6

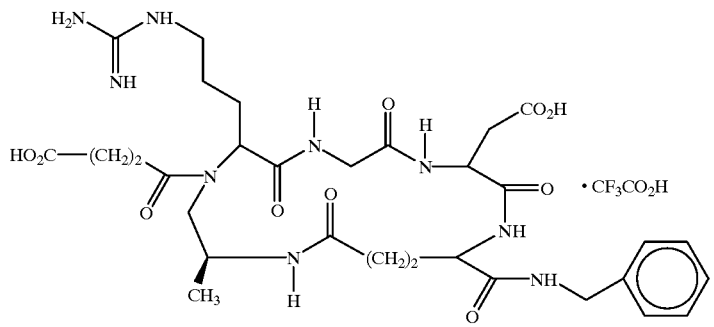

Optional step n
Cyclo[Ala$\Psi$[CH$_2$N(CO(CH$_2$)$_2$CO$_2$H)]-Arg(N$^g$-Tos)-Gly-Asp($\beta$-Chxl)-$\delta$-Glu](NHBn)-SEQ ID NO: 7

Suspend Cyclo[Ala$\Psi$[CH$_2$NH]-Arg(N$^g$-Tos)-Gly-Asp($\beta$-Chxl)-$\delta$-Glu](NHBn) (SEQ ID NO: 5) (0.5 mmol) in dimethylformamide (10 mL) and add diisopropylethylamine (0.44 mL) and succinic anhydride (250 mg, 2.5 mmol).

Shake for 4 hours, filter, wash with dimethylformamide and dry in vacuo to give the title compound.

Step o

Cyclo[AlaΨ[CH$_2$N(CO(CH$_2$)$_2$CO$_2$H)]-Arg-Gly-Asp-δ-Glu](NHBn)•CF$_3$CO$_2$H-SEQ ID NO: 6

Suspend Cyclo(AlaΨ[CH$_2$N(CO(CH$_2$)$_2$CO$_2$H)]-Arg(N$^g$-Tos)-Gly-Asp(β-Chxl)-δ-Glu](NHBn) (SEQ ID NO: 7) (183 mg) in hydrogen fluoride and anisole. Stir for 1 hour at 0° C. Allow the solvent to evaporate and extract into 30% aqueous acetic acid. Lyophillize to give the title compound (139 mg). Purify by reverse phase HPLC (aqueous trifluoroacetic acid/acetonitrile) to give the title compound.

EXAMPLE 3

MDL 100,187

Cyclo[AlaΨ[CH$_2$N((CH$_2$)$_3$CO$_2$H)]-Arg-Gly-Asp-δ-Glu](NHBn)•CF$_3$CO$_2$H-SEQ ID NO: 8

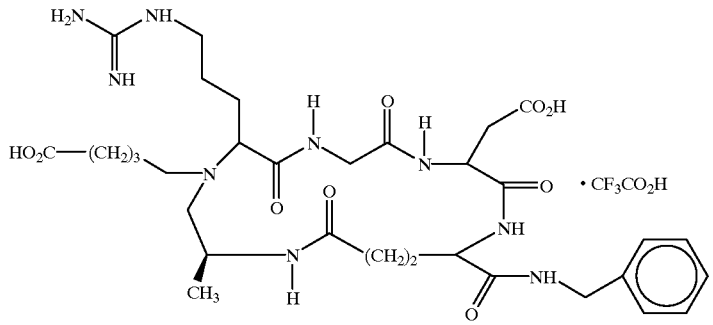

Optional step 1

Boc-AlaΨ[CH$_2$N((CH$_2$)$_3$CO$_2$H)]-Arg(N$^g$-Tos)-Gly-Asp(β-Chxl)-Glu(δ-oxime resin)(NHBn)-SEQ ID NO: 9

Suspend Boc-AlaΨ[CH$_2$NH]-Arg(N$^g$-Tos)-Gly-Asp(β-Chxl)-Glu(δ-oxime resin)(NHBn) (SEQ ID NO: 4) (0.5 mmol) in 1% acetic acid in dimethylformamide (10 mL). Add succinic semialdehyde (1.6 mL, 15% in water) and sodium cyanohydride (100 mg). Shake for 4 hours, filter, wash with dimethylformamide and dichloromethane and dry in vacuo to give the title compound.

Step m

Cyclo[AlaΨ[CH$_2$N((CH$_2$)$_3$CO$_2$H)]-Arg(N$^g$-Tos)-Gly-Asp(β-Chxl)-δ-Glu](NHBn)-SEQ ID NO: 10

Treat Boc-AlaΨ[CH$_2$N((CH$_2$)$_3$CO$_2$H)]-Arg(N$^g$-Tos)-Gly-Asp(β-Chxl)-Glu(δ-oxime resin)(NHBn) (SEQ ID NO: 9) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 4 days. Filter and wash with dimethylformamide. Evaporate the solvent in vacuo and dissolve the residual oil in acetic acid. Lyophillize to give the title compound (408 mg, %).

Step o

Cyclo[AlaΨ[CH$_2$N((CH$_2$)$_3$CO$_2$H)]-Arg-Gly-Asp-δ-Glu](NHBn)•CF$_3$CO$_2$H-SEQ ID NO: 8

Suspend Cyclo[AlaΨ[CH$_2$N((CH$_2$)$_3$CO$_2$H)]-Arg(N$^g$-TOS)-Gly-Asp(β-Chxl)-δ-Glu](NHBn) (SEQ ID NO: 10) (408 mg) in hydrogen fluoride and anisole. Stir for 1 hour at 0° C. Allow the solvent to evaporate and extract into 30% aqueous acetic acid. Lyophillize to give the title compound (329 mg) and purify by Reverse phase-HPLC (aqueous trifluoroacetic acid/acetonitrile) to give the title compound (32.7 mg).

(M+H)$^+$=690.4

AAA: Asp, 1.04; Glu, 1.05; Gly, 0.91; 61.8% peptide

EXAMPLE 4

Cyclo[AlaΨ[CH$_2$N((CH$_2$)$_3$Ph)]-Arg-Gly-Asp-δ-Glu](NHBn)•CF$_3$CO$_2$H-SEQ ID NO: 11

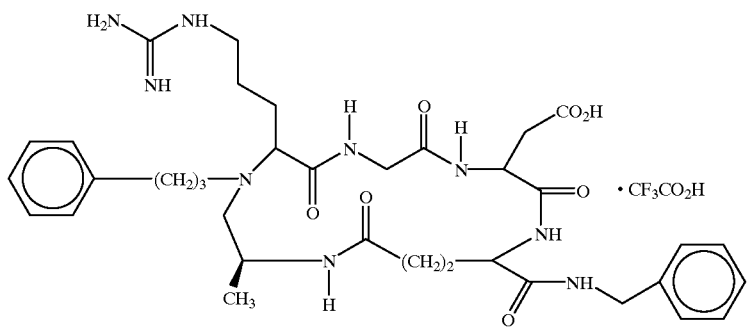

Optional Step 1

Boc-AlaΨ[CH$_2$N((CH$_2$)$_3$Ph)]-Arg(N$^g$-Tos)-Gly-Asp(β-Chxl)-Glu(δ-oxime resin)(NHBn)-SEQ ID NO: 12

Suspend Boc-AlaΨ[CH$_2$NH]-Arg(N$^g$-Tos)-Gly-Asp(β-Chxl)-Glu(δ-oxime resin)(NHBn) (SEQ ID NO: 4) (0.5 mmol) in 1% acetic acid in dimethylformamide (10 mL). Add dihydrocinnamaldehyde (0.33 mL, 336 mg) and sodium cyanohydride (100 mg). Shake for 4 hours, filter, wash with dimethylformamide and methylene chloride. Dry in vacuo to give the title compound.

Step m

Cyclo[AlaΨ[CH$_2$N((CH$_2$)$_3$Ph)]-Arq(N$^g$-Tos)-Gly-Asp-(β-Chxl)-δ-Glu](NHBn)-SEQ ID NO: 13

Treat Boc-AlaΨ[CH$_2$N((CH$_2$)$_3$Ph)]-Arg(N$^g$-Tos)-Gly-Asp(β-Chxl)-Glu(δ-oxime resin)(NHBn) (SEQ ID NO: 12) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 4 days. Filter and wash with dimethylformamide. Evaporate the solvent in vacuo and dissolve the residual oil in acetic acid. Lyophillize to give the title compound (176 mg).

Step o

Cyclo[AlaΨ[CH$_2$N((CH$_2$)$_3$Ph)]-Arg-Gly-Asp-δ-Glu](NHBn)•CF$_3$CO$_2$H-SEQ ID NO: 11

Suspend Cyclo[AlaΨ[CH$_2$N((CH$_2$)$_3$Ph)]-Arg(N$^g$-Tos)-Gly-Asp(β-Chxl)-δ-Glu](NHBn) (SEQ ID NO: 13) (176 mg) in hydrogen fluoride and anisole. Stir for 1 hour at 0° C. Allow the solvent to evaporate and extract into 30% aqueous acetic acid. Lyophillize to give the title compound and purify by Reverse phase-HPLC (aqueous trifluoroacetic acid/acetonitrile) to give the title compound.

(M+H)$^+$=722.5

AAA: Asp, 1.01; Glu, 1.03; Gly, 0.96; 57.5% peptide

EXAMPLE 5

Cyclo[AlaΨ[CH$_2$N(CO(CH$_2$)$_2$Ph)]-Arg-Gly-Asp-δ-Glu](NHBn)•CF$_3$CO$_2$H-SEQ ID NO: 14

Optional Step n

Cyclo[AlaΨ[CH$_2$N(CO(CH$_2$)$_2$Ph)]-Arg(N$^g$-Tos)-Gly-Asp(β-Chxl)-δ-Glu](NHBn)-SEQ ID NO: 15

Mix hydrocinnamic acid (751 mg, 5 mmol), methylene chloride (12 mL) and add a 1M solution of 1,3-dicyclohexylcarbodiimide in 1-methyl-2-pyrrolidinone (2.5 mL) along with methylene chloride (5 mL). Stir at room temperature for 1 hour and filter to give a solution of hydrocinnamic acid symmetrical anhydride.

Suspend Cyclo[AlaΨ[CH$_2$NH]-Arg(N$^g$-Tos)-Gly-Asp(β-Chxl)-δ-Glu](NHBn) (SEQ ID NO: 5) (0.5 mmol) in the solution of hydrocinnamic acid symmetrical anhydride. Add diisopropylethylamine (0.44 mL) and shake for 4 hours. Filter, wash with dimethylformamide and methylene chloride. Dry in vacuo to give the title compound.

Step o

Cyclo[AlaΨ[CH$_2$N(CO(CH$_2$)$_2$Ph)]-Arg-Gly-Asp-δ-Glu](NHBn)•CF$_3$CO$_2$H-SEQ ID NO: 14

Suspend Cyclo[AlaΨ[CH$_2$N(CO(CH$_2$)$_2$Ph)]-Arg(N$^g$-Tos)-Gly-Asp(δ-Chxl)-δ-Glu](NHBn) (SEQ ID NO: 15) (0.5 mmol) in hydrogen fluoride and anisole. Stir for 1 hour at 0° C. Allow the solvent to evaporate and extract into 30% aqueous acetic acid. Lyophillize to give the title compound and purify by Reverse phase-HPLC (aqueous trifluoroacetic acid/acetonitrile) to give the title compound.

EXAMPLE 6

Cyclo[AlaΨ[CH$_2$NH]-Arg-Gly-Asp-δ-Glu](LeuNHBn)•CF$_3$CO$_2$H

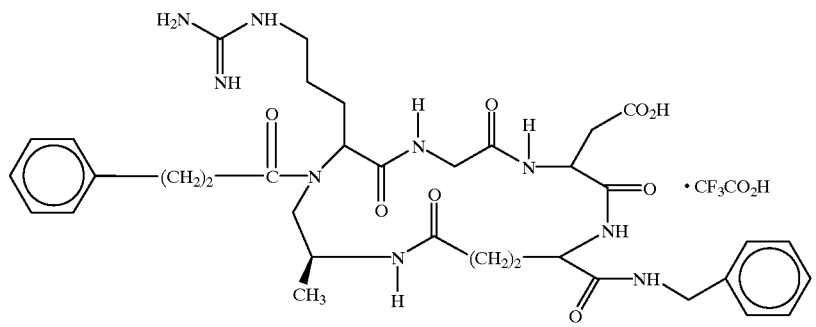

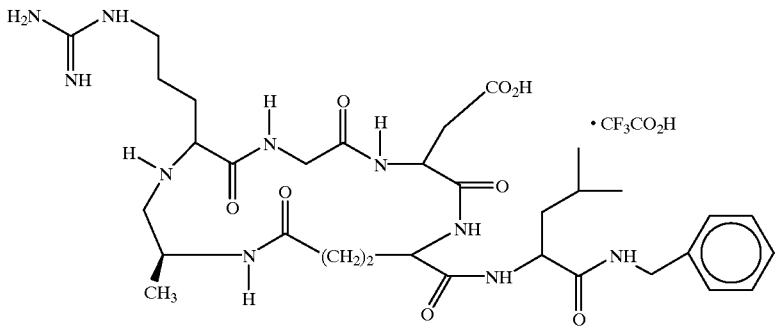

Step a
Boc-Glu(δ-Bn)(LeuNHBn)

Dissolve Boc-Leu(NHBn) (1.60 g, 5 mmol) in a solution of 4N hydrochloric acid in dioxane (10 mL). Stir at room temperature for 30 minutes and evaporate the solvent in vacuo to give Leu(NHBn)•hydrochloride.

Dissolve Boc-Glu(δ-Bn) (1.60 g, 5 mmol) in dichloromethane (10 mL) and add 1-hydroxybenzotriazole hydrate (0.84 g, 5.5 mmol), 1-(3-dimethylaminopropyl)3-ethylcarbodiimide hydrochloride (1.05 g, 5.5 mmol), Leu (NHBn)•hydrochloride (5 mmol) and diisopropylethylamine (1.36 mL, mmol). Stir at room temperature overnight and dilute with ethyl acetate (200 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a white crystalline solid (2.5 g, 93%).

MS (CI/CH$_4$) 540 (M+H$^+$)

Step b
Glu(δ-Bn)-Leu(NHBn) hydrochloride

Dissolve Boc-Glu(δ-Bn)-Leu(NHBn) (2.5 g) in a solution of 4N hydrochloric acid in dioxane (10 mL). Stir at room temperature for 30 minutes and evaporate the solvent in vacuo to give the title compound.

Step c
Boc-Asp(β-Chxl)-Glu(δ-Bn)-Leu(NHBn)

Dissolve Glu(δ-Bn)-Leu(NHBn) hydrochloride (4.6 mmol) in dimethylformamide (10 mL) and add 1-hydroxybenzotriazole hydrate (0.78 g, 5.06 mmol), Boc-Asp(β-Chxl) (1.46 g, 4.6 mmol), diisopropylethylamine (1.34 mL) and 1-(3-dimethylaminopropyl)3-ethylcarbodiimide hydrochloride (0.98 g, 5.06 mmol). Stir at room temperature overnight and dilute with ethyl acetate (150 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a solid (3.27 g, 96%).

MS (CI/CH$_4$) 737 (M+H$^+$)

Step d
Boc-Asp(β-Chxl)-Glu-Leu(NHBn)

Dissolve Boc-Asp(β-Chxl)-Glu(δ-Bn)-Leu(NHBn) (18.6 mmol) in methanol (200 mL) and add Perlman's catalyst (200 mg). Hydrogenate on a Paar Hydrogenation Apparatus for 4 hours, filter through Celite filter aid and evaporate the solvent in vacuo to give the title compound.

Step e
Boc-Asp(β-Chxl)-Glu(δ-oxime resin)-Leu(NHBn)

Dissolve Boc-Asp(β-Chxl)-Glu-Leu(NHBn) (18.6 mmol) in methylene chloride (140 mL). Add oxime resin (21 g, 0.69 meq/g, 14.5 mmol) and a 0.5M solution of 1,3-dicyclohexylcarbodiimide in methylene chloride (42 mL, 21 mmol) and mix on a rotary evaporator for 20 hours. Filter, wash with dimethylformamide (2×200 mL), methylene chloride (200 mL), methanol (3×200 mL) and methylene chloride (3×200 mL). Suspend in a capping mixture of acetic anhydride:diisopropylethylamine:dimethylformamide (6:2:24) for 30 minutes. Filter and wash with dimethylformamide (2×200 mL), methanol (3×200 mL) and methylene chloride (3×200 mL). Dry in vacuo to give the title compound.

Step f
Asp(β-Chxl)-Glu(δ-oxime resin)-Leu(NHBn)

Briefly wash Boc-Asp(β-Chxl)-Glu(δ-oxime resin)-Leu (NHBn) (2 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step g
Boc-Gly-Asp(β-Chxl)-Glu(δ-oxime resin)-Leu(NHBn)-SEQ ID NO: 16

Add Asp(β-Chxl)-Glu(δ-oxime resin)-Leu(NHBn) to a solution of Boc-Gly symmetrical anhydride. Stir at room temperature for 2 hours, filter and wash with dimethylformamide (2×50 mL). Suspend in a capping mixture of acetic anhydride:diisopropylethylamine:dimethylformamide (6:2:24) for 30 minutes. Filter, wash with dimethylformamide (3×50 mL), isopropanol (3×50 mL) and methylene chloride (2×50 mL). Dry in vacuo to give the title compound.

Step h
Gly-Asp(β-Chxl)-Glu(δ-oxime resin)-Leu(NHBn)-SEQ ID NO: 17

Briefly wash Boc-Gly-Asp(β-Chxl)-Glu(δ-oxime resin)-Leu(NHBn) (SEQ ID NO: 16) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step i
N$^\alpha$-Boc-Arg(N$^g$-Tos)-Gly-Asp(β-Chxl)-Glu(δ-oxime resin)-Leu(NHBn)-SEQ ID NO: 18

Dissolve N$^\alpha$-Boc-Arg(N$^g$-Tos) symmetrical anhydride (7.5 mmol) in dimethylformamide (40 mL) and add Gly- Asp(β-Chxl)-Glu(δ-oxime resin)-Leu(NHBn) (SEQ ID NO: 17) (0.5 mmol). Shake at room temperature for 3 hours, filter and wash with dimethylformamide (2×50 mL) and methylene chloride. Dry in vacuo to give the title compound.

Step j
Arg(N$^g$-Tos)-Gly-Asp(β-Chxl)-Glu(δ-oxime resin)-Leu(NHBn)-SEQ ID NO: 19

Briefly wash N$^α$-Boc-Arg(N$^g$-Tos)-Gly-Asp(α-Chxl)-Glu (δ-oxime resin)-Leu(NHBn) (SEQ ID NO: 18) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step k
Boc-AlaΨ[CH$_2$NH]-Arg(N$^g$-Tos)-Gly-Asp(β-Chxl)-Glu(δ-oxime resin)-Leu(NHBn)-SEQ ID NO: 20

Dissolve Boc-Ala-al (5mmol) in a solution of 1% acetic acid in dimethylformamide (10 mL). Add Arg(N$^g$-Tos)-Gly-Asp(δ-Chxl)-Glu(δ-oxime resin)-Leu(NHBn) (SEQ ID NO: 19) (0.5 mmol) and sodium cyanoborohydride (150 mg). Shake for 2 hours and filter. Wash with dimethylformamide (3×20 mL), methylene chloride (3×20 mL) and evaporate the solvent in vacuo to give the title compound.

Step m
Cyclo[AlaΨ[CH$_2$NH]-Arg(N$^g$-Tos)-Gly-Asp(β-Chxl)-δGlu]-Leu(NHBn)

Treat Boc-AlaΨ[CH$_2$NH]-Arg(N$^g$-Tos)-Gly-Asp(β-Chxl)-Glu(δ-oxime resin)-Leu(NHBn) (SEQ ID NO: 20) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step o
Cyclo[AlaΨ[CH$_2$NH]-Arg-Gly-Asp-δ-Glu]-Leu(NHBn)•CF$_3$CO$_2$H

Suspend Cyclo[AlaΨ[CH$_2$NH]-Arg(N$^g$-Tos)-Gly-Asp(β-Chxl)-δ-Glu]-Leu(NHBn) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

EXAMPLE 7

Cyclo[AlaΨ[CH$_2$NH]-Arg-Gly-Asp-δ-Glu]-Trp(NHBn)•CF$_3$CO$_2$H

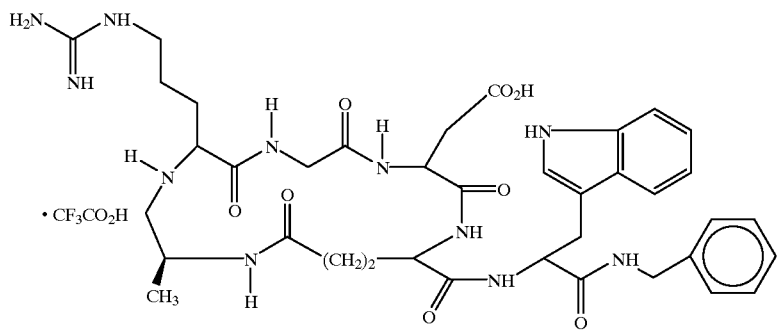

Step a
Boc-Glu(δ-Bn)-Trp(NHBn)

Dissolve Boc-Trp(NHBn) (1.97 g, 5 mmol) in a solution of 4N hydrochloric acid in dioxane (10 mL). Stir at room temperature for 30 minutes and evaporate the solvent in vacuo to give Trp(NHBn)•hydrochloride.

Dissolve Boc-Glu(δBn) (1.60 g, 5 mmol) in dichloromethane (10 mL) and add 1-hydroxybenzotriazole hydrate (0.84 g, 5.5 mmol), 1-(3-dimethylaminopropyl)3-ethylcarbodiimide hydrochloride (1.05 g, 5.5 mmol), Trp(NHBn)•hydrochloride (5 mmol) and diisopropylethylamine (1.36 mL, mmol). Stir at room temperature overnight and dilute with ethyl acetate (200 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a solid (3.11 g, 100%).

MS (CI/CH$_4$) 613 (M+H$^+$)

Step b
Glu(δ-Bn)-Trp(NHBn) hydrochloride

Dissolve Boc-Glu(δ-Bn)-Trp(NHBn) (3.11 g) in a solution of 4N hydrochloric acid in dioxane (10 mL). Stir at room temperature for 30 minutes and evaporate the solvent innvacuo to give the title compound.

Step c
Boc-Asp(β-Chxl)-Glu(δ-Bn)-Trp(NHBn)

Dissolve Glu(δ-Bn)-Trp(NHBn) hydrochloride (5 mmol) in dimethylformamide (10 mL) and add 1-hydroxybenzotriazole hydrate (0.84 g, 5.5 mmol), Boc-Asp(β-Chxl) (1.58 g, 5 mmol), diisopropylethylamine (1.46 mL) and 1-(3-dimethylaminopropyl)3-ethylcarbodiimide hydrochloride (1.05 g, 5.5 mmol). Stir at room temperature overnight and dilute with ethyl acetate (150 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a solid (3.77 g, 93%).

MS (CI/CH$_4$) 810 (M+H$^+$)

Step d
Boc-Asp(β-Chxl)-Glu-Trp(NHBn)

Dissolve Boc-Asp(β-Chxl)-Glu(δ-Bn)-Trp(NHBn) (18.6 mmol) in methanol (200 mL) and add Perlman's catalyst (200 mg). Hydrogenate on a Paar Hydrogenation Apparatus for 4 hours, filter through Celite filter aid and evaporate the solvent in vacuo to give the title compound.

Step e

Boc-Asp(β-Chxl)-Glu(δ-oxime resin)-Trp(NHBn)

Dissolve Boc-Asp(β-Chxl)-Glu-Trp(NHBn) (18.6 mmol) in methylene chloride (140 mL). Add oxime resin (21 g, 0.69 meq/g, 14.5 mmol) and a 0.5M solution of 1,3-dicyclohexylcarbodiimide in methylene chloride (42 mL, 21 mmol) and mix on a rotary evaporator for 20 hours. Filter, wash with dimethylformamide (2×200 mL), methylene chloride (200 mL), methanol (3×200 mL) and methylene chloride (3×200 mL). Suspend in a capping mixture of acetic anhydride:diisopropylethylamine:dimethylformamide (6:2:24) for 30 minutes. Filter and wash with dimethylformamide (2×200 mL), methanol (3×200 mL) and methylene chloride (3×200 mL). Dry in vacuo to give the title compound.

Step f

Asp(β-Chxl)-Glu(δ-oxime resin)-Trp(NHBn)

Briefly wash Boc-Asp(β-Chxl)-Glu(δ-oxime resin)-Trp(NHBn) (2 mmol) with 50 mL of a solution of 25% trifluoroactic acid in methylene chloride with 1% anisole and filter. Treat with 50 mL of a solution of 25% trifluoroactic acid in methylene chloride with 1% anisole, stir for 25 minutes and filter. Briefly wash three times with methylene chloride (50mL) and filter. Briefly wash three times with isopropanol (50 mL) and filter. Briefly wash two times with 50 mL of a solution of 1% diisopropylethylamine in methylene chloride and filter to give the title compound.

Step g

Boc-Gly-Asp(β-Chxl)-Glu(δ-oxime resin)-Trp(NHBn)-SEQ ID NO: 21

Add Asp(β-Chxl)-Glu(δ-oxime resin)-Trp(NHBn) (0.5 mmol) to a solution of Boc-Gly symmetrical anhydride. Stir at room temperature for 2 hours, filter and wash with dimethylformamide (2×50 mL). Suspend in a capping mixture of acetic anhydride:diisopropylethylamine:dimethylformamide (6:2;24) for 30 minutes. Filter, wash with dimethylformamide (3×50 mL), isopropanol (3×50 mL) and methylene chloride (2×50 mL). Dry in vacuo to give the title compound.

Step h

Gly-Asp(β-Chxl)-Glu(δ-oxime resin)-Trp(NHBn)-SEQ ID NO: 22

Briefly wash Boc-Gly-Asp(β-Chxl)-Glu(δ-oxime resin)-Trp(NHBn) (SEQ ID NO: 21) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step i

N$^\alpha$-Boc-Arg(N$^g$-Tos)-Gly-Asp(β-Chxl)-Glu(δ-oxime resin)-Trp(NHBn)-SEQ ID NO: 23

Dissolve N$^\alpha$-Boc-Arg(N$^g$-Tos) symmetrical anhydride (7.5 mmol) in dimethylformamide (40 mL) and add Gly-Asp(β-Chxl)-Glu(δ-oxime resin)-Trp(NHBn) (SEQ ID NO: 22). Shake at room temperature for 3 hours, filter and wash with dimethylformamide (2×50 mL) and methylene chloride. Dry in vacuo to give the title compound.

Step j

Arg(N$^g$-Tos)-Gly-Asp(β-Chxl)-Glu(δ-oxime resin)-Trp(NHBn)-SEQ ID NO: 24

Briefly wash N$^\alpha$-Boc-Arg(N$^g$-Tos)-Gly-Asp(β-Chxl)-Glu(δ-oxime resin)-Trp(NHBn) (SEQ ID NO: 23) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step k

Boc-AlaΨ[CH$_2$NH]-Arg(N$^g$-Tos)-Gly-Asp(β-Chxl)-Glu(δ-oxime resin)-Trp(NHBn)-SEQ ID NO: 25

Dissolve Boc-Ala-al (5 mmol) in a solution of 1% acetic acid in dimethylformamide (10 mL). Add Arg(N$^g$-Tos)-Gly-Asp(β-Chxl)-Glu(δ-oxime resin)-Trp(NHBn) (SEQ ID NO: 24) (0.5 mmol) and sodium cyanoborohydride (150 mg). Shake for 2 hours and filter. Wash with dimethylformamide (3×20 mL), methylene chloride (3×20 mL) and evaporate the solvent in vacuo to give the title compound.

Step m

Cyclo[AlaΨ[CH$_2$NH]-Arg(N$^g$-Tos)-Gly-Asp(β-Chxl)-δ-Glu]-Trp(NHBn)

Treat Boc-AlaΨ[CH$_2$NH]-Arg(N$^g$-Tos)-Gly-Asp(β-Chxl)-Glu(δ-oxime resin)-Trp(NHBn) (SEQ ID NO: 25) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step o

Cyclo[AlaΨ[CH$_2$NH]-Arg-Gly-Asp-δ-Glu]-Trp(NHBn)•CF$_3$CO$_2$H

Suspend Cyclo[AlaΨ[CH$_2$NH]-Arg(N$^g$-Tos)-Gly-Asp(β-Chxl)-δ-Glu]-Trp(NHBn) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

EXAMPLE 8

Cyclo[AlaΨ[CH$_2$NH]-Arg-Gly-Asp-δ-Glu]-Arg (NHBn)•CF$_3$CO$_2$H

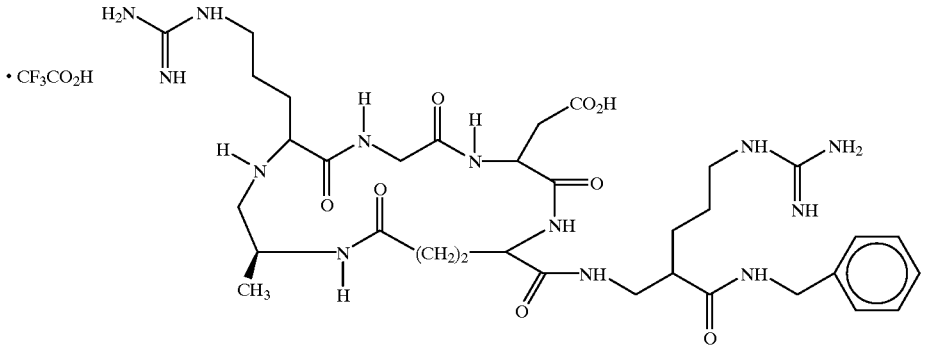

Step a
Boc-Glu(δ-Bn)-Arg(N$^g$-Tos)(NHBn)

Dissolve N$^\alpha$-Boc-Arg(N$^g$-Tos)(NHBn) (2.59 g, 5 mmol) in a solution of 4N hydrochloric acid in dioxane (10 mL). Stir at room temperature for 30 minutes and evaporate the solvent in vacuo to give Arg(N$^g$-Tos)(NHBn)•hydrochloride. Dissolve Boc-Glu(δ-Bn) (1.60 g, 5 mmol) in dichloromethane (10 mL) and add 1-hydroxybenzotriazole hydrate (0.84 g, 5.5 mmol), 1-(3-dimethylaminopropyl)3-ethylcarbodiimide hydrochloride (1.05 g, 5.5 mmol), Arg(N$^g$-Tos)(NHBn)•hydrochloride (5 mmol) and diisopropylethylamine (1.36 mL, mmol). Stir at room temperature overnight and dilute with ethyl acetate (200 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a solid (2.95 g, 80%).

MS (Neg Ion CI/CH$_4$) 735 (M−H)$^-$

Step b
Glu(δ-Bn)-Arg(N$^g$-Tos)(NHBn) hydrochloride

Dissolve Boc-Glu(δ-Bn)-Arg(N$^g$-Tos)(NHBn) (2.95 g) in a solution of 4N hydrochloric acid in dioxane (10 mL). Stir at room temperature for 30 minutes and evaporate the solvent in vacuo to give the title compound.

Step c
Boc-Asp(β-Chxl)-Glu(δ-Bn)-Arg(N$^g$-Tos)(NHBn)

Dissolve Glu(δ-Bn)-Arg(N$^g$-Tos)(NHBn) hydrochloride (4 mmol) in dimethylformamide (10 mL) and add 1-hydroxybenzotriazole hydrate (0.67 g, 4.4 mmol), Boc-Asp(β-Chxl) (1.26 g, 4 mmol), diisopropylethylamine (1.12 mL) and 1-(3-dimethylaminopropyl)3-ethylcarbodiimide hydrochloride (0.84 g, 4.4 mmol). Stir at room temperature overnight and dilute with ethyl acetate (150 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a solid (1.21 g, 32%).

MS (FAB CI/CH$_4$) 943.5 (M+H$^+$)

Step d
Boc-AsP(β-Chxl)-Glu-Arg(N$^g$-Tos)(NHBn)

Dissolve Boc-Asp(β-Chxl)-Glu(δ-Bn)-Arg(N$^g$-Tos)(NHBn) (18.6 mmol) in methanol (200 mL) and add Perlman's catalyst (200 mg). Hydrogenate on a Paar Hydrogenation Apparatus for 4 hours, filter through Celite filter aid and evaporate the solvent in vacuo to give the title compound.

Step e
Boc-Asp(β-Chxl)-Glu(δ-oxime resin)-Arg(N$^g$-Tos)(NHBn)

Dissolve Boc-Asp(β-Chxl)-Glu-Arg(N$^g$-Tos)(NHBn) (18.6 mmol) in methylene chloride (140 mL). Add oxime resin (21 g, 0.69 meq/g, 14.5 mmol) and a 0.5M solution of 1,3-dicyclohexylcarbodiimide in methylene chloride (42 mL, 21 mmol) and mix on a rotary evaporator for 20 hours. Filter, wash with dimethylformamide (2×200 mL), methylene chloride (200 mL), methanol (3×200 mL) and methylene chloride (3×200 mL). Suspend in a capping mixture of acetic anhydride:diisopropylethylamine:dimethylformamide (6:2:24) for 30 minutes. Filter and wash with dimethylformamide (2×200 mL), methanol (3×200 mL) and methylene chloride (3×200 mL). Dry in vacuo to give the title compound.

Step f
Asp(β-Chxl)-Glu(δ-oxime resin)-Arg(N$^g$-Tos)(NHBn)

Briefly wash Boc-Asp(β-Chxl)-Glu(δ-oxime resin)-Arg(N$^g$-Tos)(NHBn) (2 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step g
Boc-Gly-Asp(β-Chxl)-Glu(δ-oxime resin)-Arg(N$^g$-Tos)(NHBn)-SEQ ID NO: 26

Add Asp(β-Chxl)-Glu(δ-oxime resin)-Arg(N$^g$-Tos)(NHBn) (0.5 mmol) to a solution of Boc-Gly symmetrical anhydride (0.5 mmol). Stir at room temperature for 2 hours, filter and wash with dimethylformamide (2×50 mL). Suspend in a capping mixture of acetic anhydride:diisopropylethylamine:dimethylformamide (6:2:24) for 30 minutes. Filter, wash with dimethylformamide (3×50 mL), isopropanol (3×50 mL) and methylene chloride (2×50 mL). Dry in vacuo to give the title compound.

Step h
Gly-Asp(β-Chxl)-Glu(δ-oxime resin)-Arg(N$^g$-Tos)(NHBn)-SEQ ID NO: 27

Briefly wash Boc-Gly-Asp(β-Chxl)-Glu(δ-oxime resin)-Arg(N$^g$-Tos)(NHBn) (SEQ ID NO: 26) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter.

Briefly wash two times with 50 mL of a solution of 1% diisopropylethylamine in methylene chloride and filter to give the title compound.

Step i
Boc-Arg(N$^g$-Tos)-Gly-Asp(β-Chxl)-Glu(δ-oxime resin)-Arg(N$^g$-Tos)(NHBn)-SEQ ID NO: 28

Dissolve Nα-Boc-Arg(N$^g$-Tos) symmetrical anhydride (7.5 mmol) in dimethylformamide (40 mL) and add Gly-Asp(β-Chxl)-Glu(δ-oxime resin)-Arg(N$^g$-Tos)(NHBn) (SEQ ID NO: 27). Shake at room temperature for 3 hours, filter and wash with dimethylformamide (2×50 mL) and methylene chloride. Dry in vacuo to give the title compound.

Step j
Arg(N$^g$-Tos)-Gly-Asp(β-Chxl)-Glu(δ-oxime resin)-Arg(N$^g$-Tos)(NHBn)-SEQ ID NO: 29

Briefly wash Boc-Arg(N$^g$-Tos)-Gly-Asp(β-Chxl)-Glu(δ-oxime resin)-Arg(N$^g$-Tos)(NHBn) (SEQ ID NO: 28) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step k
Boc-AlaΨ[CH$_2$NH]-Ar(N$^g$-Tos)-Gly-Asp(β-Chxl)-Glu(δ-oxime resin)-Arg(N$^g$-Tos)(NHBn)-SEQ ID NO: 30

Dissolve Boc-Ala-al (5 mmol) in a solution of 1% acetic acid in dimethylformamide (10 mL). Add Arg(N$^g$-Tos)-Gly-Asp(β-Chxl)-Glu(δ-oxime resin)-Arg(N$^g$-Tos)(NHBn) (SEQ ID NO: 29) (0.5 mmol) and sodium cyanoborohydride (150 mg). Shake for 2 hours and filter. Wash with dimethylformamide (3×20 mL), methylene chloride (3×20 mL) and evaporate the solvent in vacuo to give the title compound.

Step m
Cyclo[AlaΨ[CH$_2$NH]-Arg(N$^g$-Tos)-Gly-Asp(β-Chxl)-δ-Glu]-Arg(N$^g$-Tos)(NHBn)

Treat Boc-AlaΨ[CH$_2$NH]-Arg(N$^g$-Tos)-Gly-Asp(β-Chxl)-Glu(δ-oxime resin)-Arg(N$^g$-Tos)(NHBn) (SEQ ID NO: 30) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step o
Cyclo[AlaΨ[CH$_2$NH]-Arg-Gly-Asp-δ-Glu]-Arg(NHBn)•CF$_3$CO$_2$H

Suspend Cyclo[AlaΨ[CH$_2$NH]-Arg(N$^g$-Tos)-Gly-Asp(β-Chxl)-δ-Glu]-Arg(N$^g$-Tos)(NHBn) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

EXAMPLE 9

Cyclo[AlaΨ[CH$_2$NH]-Arg-Gly-Asp-δ-Glu]-Asp (NHBn)•CF$_3$CO$_2$H

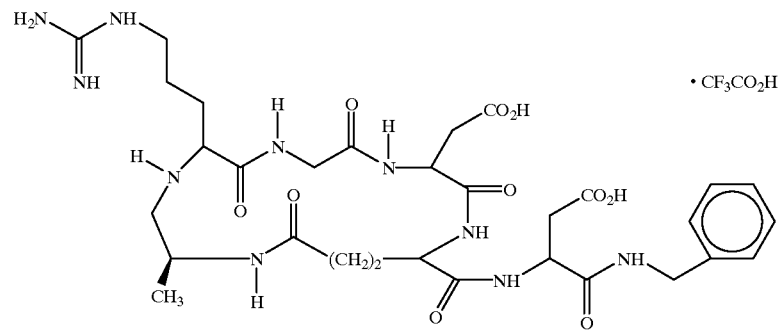

Step a
Boc-Glu(δ-Bn)-Asp(β-Chxl)(NHBn)

Dissolve Boc-Asp(β-Chxl)(NHBn) (2.02 g, 5 mmol) in a solution of 4N hydrochloric acid in dioxane (10 mL). Stir at room temperature for 30 minutes and evaporate the solvent in vacuo to give Asp(β-Chxl)(NHBn)•hydrochloride.

Dissolve Boc-Glu(δ-Bn) (1.60 g, 5 mmol) in dichloromethane (10 mL) and add 1-hydroxybenzotriazole hydrate (0.84 g, 5.5 mmol), 1-(3-dimethylaminopropyl)3-ethylcarbodiimide hydrochloride (1.05 g, 5.5 mmol), Asp (β-Chxl)(NHBn)•hydrochloride (5 mmol) and diisopropylethylamine (1.36 mL, mmol). Stir at room temperature overnight and dilute with ethyl acetate (200 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a solid (3.05 g, 98%).

MS (CI/CH$_4$) 624 (M+H)+

Step b
Glu(δ-Bn)-Asp(β-Chxl)(NHBn) hydrochloride

Dissolve Boc-Glu(δ-Bn)-Asp(β-Chxl)(NHBn) (3.05 g, 4.89 mmol) in a solution of 4N hydrochloric acid in dioxane (10 mL). Stir at room temperature for 30 minutes and evaporate the solvent in vacuo to give the title compound.

Step c
Boc-Asp(β-Chxl)-Glu(δ-Bn)-Asp(β-Chxl)(NHBn)

Dissolve Glu(δ-Bn)-Asp(β-Chxl)(NHBn) hydrochloride (4.89 mmol) in dimethylformamide (10 mL) and add 1-hydroxybenzotriazole hydrate (0.82 g, 5.38 mmol), Boc-Asp(β-Chxl) (1.54 g, 4.89 mmol), diisopropylethylamine (1.39 mL) and 1-(3-dimethylaminopropyl)3-ethylcarbodiimide hydrochloride (1.03 g, 5.38 mmol). Stir at room temperature overnight and dilute with ethyl acetate (150 mL). Wash with 0.5N hydrochloric acid (3×50 mL), saturated sodium hydrogen carbonate (3×50 mL) and saturated sodium chloride (50 mL). Dry (MgSO$_4$), filter and evaporate the solvent in vacuo to give the title compound as a solid.

MS (CI/CH$_4$) 821 (M+H$^+$)

Step d

Boc-Asp(β-Chxl)-Glu-Asp(β-Chxl)(NHBn)

Dissolve Boc-Asp(β-Chxl)-Glu(δ-Bn)-Asp(β-Chxl)(NHBn) (18.6 mmol) in methanol (200 mL) and add Perlman's catalyst (200 mg). Hydrogenate on a Paar Hydrogenation Apparatus for 4 hours, filter through Celite filter aid and evaporate the solvent in vacuo to give the title compound.

Step e

Boc-Asp(β-Chxl)-Glu(δ-oxime resin)-Asp(β-Chxl)(NHBn)

Dissolve Boc-Asp(β-Chxl)-Glu-Asp(β-Chxl)(NHBn) (18.6 mmol) in methylene chloride (140 mL). Add oxime resin (21 g, 0.69meq/g, 14.5 mmol) and a 0.5M solution of 1,3-dicyclohexylcarbodiimide in methylene chloride (42 mL, 21 mmol) and mix on a rotary evaporator for 20 hours. Filter, wash with dimethylformamide (2×200 mL), methylene chloride (200 mL), methanol (3×200 mL) and methylene chloride (3×200 mL). Suspend in a capping mixture of acetic anhydride:diisopropylethylamine:dimethylformamide (6:2:24) for 30 minutes. Filter and wash with dimethylformamide (2×200 mL), methanol (3×200 mL) and methylene chloride (3×200 mL). Dry in vacuo to give the title compound.

Step f

Asp(β-Chxl)-Glu(δ-oxime resin)-Asp(β-Chxl)(NHBn)

Briefly wash Boc-Asp(β-Chxl)-Glu(δ-oxime resin)-Asp(β-Chxl)(NHBn) (2 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step g

Boc-Gly-Asp(β-Chxl)-Glu(δ-oxime resin)-Asp(β-Chxl)(NHBn)-SEQ ID NO: 31

Add Asp(β-Chxl)-Glu(δ-oxime resin)-Asp(β-Chxl)(NHBn) to a solution of Boc-Gly symmetrical anhydride. Stir at room temperature for 2 hours, filter and wash with dimethylformamide (2×50 mL). Suspend in a capping mixture of acetic anhydride:diisopropylethylamine:dimethylformamide (6:2:24) for 30 minutes. Filter, wash with dimethylformamide (3×50 mL), isopropanol (3×50 mL) and methylene chloride (2×50 mL). Dry in vacuo to give the title compound.

Step h

Gly-Asp(β-Chxl)-Glu(δ-oxime resin)-Asp(β-Chxl)(NHBn)-SEQ ID NO: 32

Briefly wash Boc-Gly-Asp(5-Chxl)-Glu(δ-oxime resin)-Asp(β-Chxl)(NHBn) (SEQ ID NO: 31) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step i

Boc-Arg(N$^g$-Tos)-Gly-Asp(β-Chxl)-Glu(δ-oxime resin)-Asp(β-Chxl)(NHBn)-SEQ ID NO: 33

Dissolve N$^\alpha$-Boc-Arg(N$^g$-Tos) symmetrical anhydride (7.5 mmol) in dimethylformamide (40 mL) and add Gly-Asp(β-Chxl)-Glu(δ-oxime resin)-Asp(β-Chxl)(NHBn) (SEQ ID NO: 32). Shake at room temperature for 3 hours, filter and wash with dimethylformamide (2×50 mL) and methylene chloride. Dry in vacuo to give the title compound.

Step j

Arg(N$^g$-Tos)-Gly-Asp(β-Chxl)-Glu(δ-oxime resin)-Asp(β-Chxl)(NHBn)-SEQ ID NO: 34

Briefly wash Boc-Arg(N$^g$-Tos)-Gly-Asp(β-Chxl)-Glu(δ-oxime resin)-Asp(β-Chxl)(NHBn) (SEQ ID NO: 33) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step k

Boc-AlaΨ[CH$_2$NH]-Arg(N$^g$-Tos)-Gly-Asp(β-Chxl)-Glu(δ-oxime resin)-Asp(β-Chxl)(NHBn)-SEQ ID NO: 35

Dissolve Boc-Ala-al (5 mmol) in a solution of 1% acetic acid in dimetylformamide (10 mL). Add Arg(N$^g$-Tos)-Gly-Asp(β-Chxl)-Glu(δ-oxime resin)-Asp(β-Chxl)(NHBn) (SEQ ID NO: 34) (0.5 mmol) and sodium cyanoborohydride (150 mg). Shake for 2 hours and filter. Wash with dimethylformamide (3×20 mL), methylene chloride (3×20 mL) and evaporate the solvent in vacuo to give the title compound.

Step m

Cyclo(AlaΨ[CH$_2$NH]-Arg(N$^g$-Tos)-Gly-Asp(β-Chxl)-δ-Glu]-Asp(β-Chxl)(NHBn)

Treat Boc-AlaΨ[CH$_2$NH]-Arg(N$^g$-Tos)-Gly-Asp(β-Chxl)-Glu(δ-oxime resin)-Asp(β-Chxl)(NHBn) (SEQ ID NO: 35) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step o

Cyclo[AlaΨ[CH$_2$NH]-Arg-Gly-Asp-δ-Glu]-Asp(NHBn)•CF$_3$CO$_2$H

Suspend Cyclo[AlaΨ[CH$_2$NH]-Arg(N$^g$-Tos)-Gly-Asp(β-Chxl)-δ-Glu]-Asp(β-Chxl)(NHBn) (0.5 mmol) in hydrogen fluoride and anisole. Stir for 1 hour at 0° C. Allow the solvent to evaporate and extract into 30% aqueous acetic acid. Lyophillize to give the title compound and purify by Reverse phase-HPLC (aqueous trifluoroacetic acid/acetonitrile) to give the title compound.

The following compounds can be prepared by analogous procedures to those described above in Examples 1–9:

Cyclo[D-PheΨ[CH$_2$NH]-Arg-Gly-Asp-δ-Glu]-Leu(NHBn)•TFA;

Cyclo[D-PheΨ[CH$_2$N(C(O)(CH$_2$)$_2$CO$_2$H)]-Arg-Gly-Asp-δ-Glu]-Leu(NHBn)•TFA;

Cyclo[D-PheΨ[CH$_2$N((CH$_2$)$_3$CO$_2$H)]-Arg-Gly-Asp-δ-Glu]-Leu(NHBn)•TFA;

Cyclo[D-PheΨ[CH$_2$N-Gly-Asp-Ac]-Arg-Gly-Asp-δ-Glu]-Leu(NHBn)•TFA;

Cyclo[PheΨ[CH$_2$NH]-Arg-Gly-Asp-δ-Glu]-Asp(NH$_2$)•TFA;
Cyclo[D-PheΨ[CH$_2$N(C(O)(CH$_2$)$_2$CO$_2$H)]-Arg-Gly-Asp-δ-Glu]-Phe(NH$_2$)•TFA;
Cyclo[D-PheΨ[CH$_2$N((CH$_2$)$_3$CO$_2$H)]-Arg-Gly-Asp-δ-Glu]-Trp(NH$_2$)•TFA;
Cyclo[D-TyrΨ[CH$_2$NH]-Arg-Gly-Asp-δ-Glu]-Leu(NHBn)•TFA;
Cyclo[D-TyrΨ[CH$_2$N(C(O)(CH$_2$)$_2$CO$_2$H)]-Arg-Gly-Asp-δ-Glu]-Leu(NHBn)•TFA;
Cyclo[D-TyrΨ[CH$_2$N((CH$_2$)$_3$CO$_2$H)]-Arg-Gly-Asp-δ-Glu]-Leu(NHBn)•TFA;
Cyclo[D-TyrΨ[CH$_2$N-Gly-Asp-Ac]-Arg-Gly-Asp-Glu]-Leu(NHBn)•TFA;

Cyclo[D-TyrΨ[CH$_2$NH]-Arg-Gly-Asp-δ-Glu]-Asp(NH$_2$)•TFA;
Cyclo[D-TyrΨ[CH$_2$N(C(O)(CH$_2$)$_2$CO$_2$H)]-Arg-Gly-Asp-δ-Glu]-Phe(NH$_2$)•TFA;
Cyclo[D-PheΨ[CH$_2$N((CH$_2$)$_3$CO$_2$H)]-Arg-Gly-Asp-δ-Glu]-Trp(NH$_2$)•TFA.

The conformationally restrained peptide analogs of formula 1 wherein X is CH$_2$NH can be prepared by one of ordinary skill in the art. A general synthetic procedure for preparing these compounds is set forth in Scheme B. In Scheme B, all substituents are as previously described unless otherwise indicated.

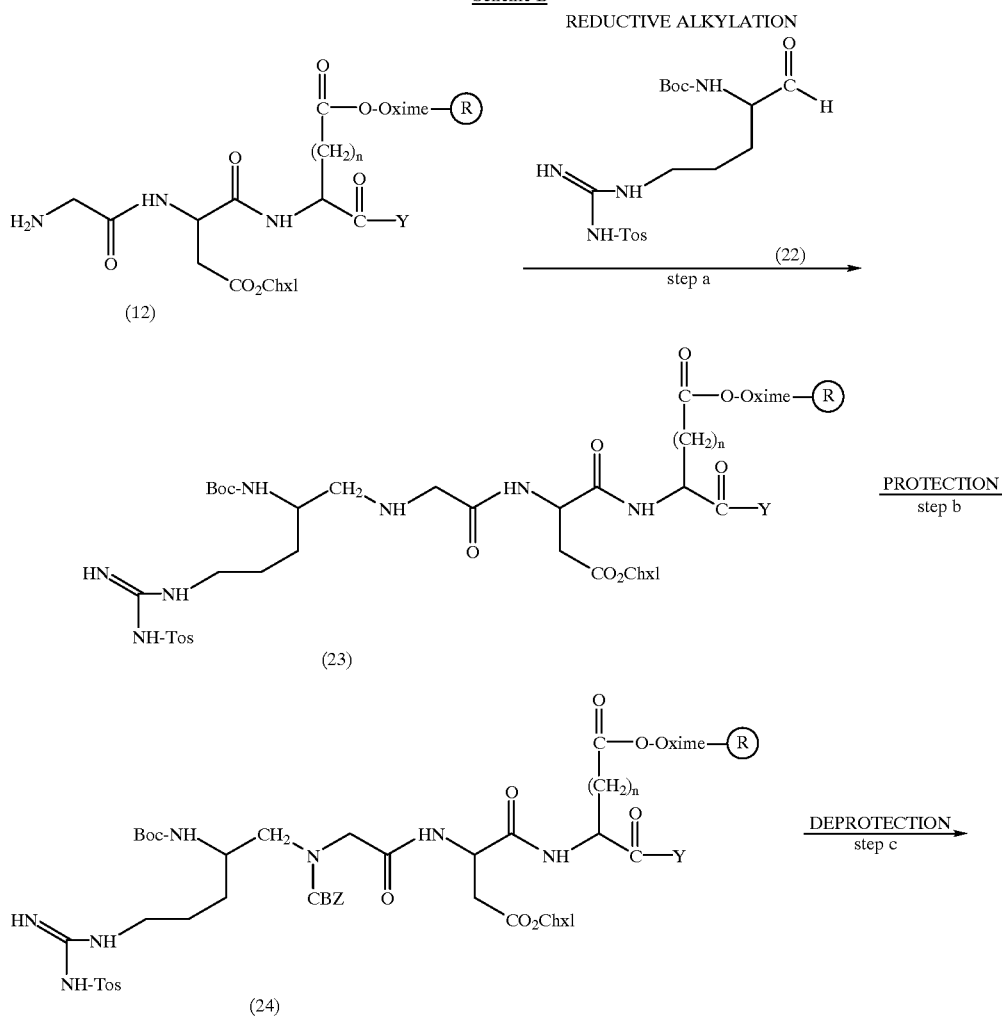

-continued
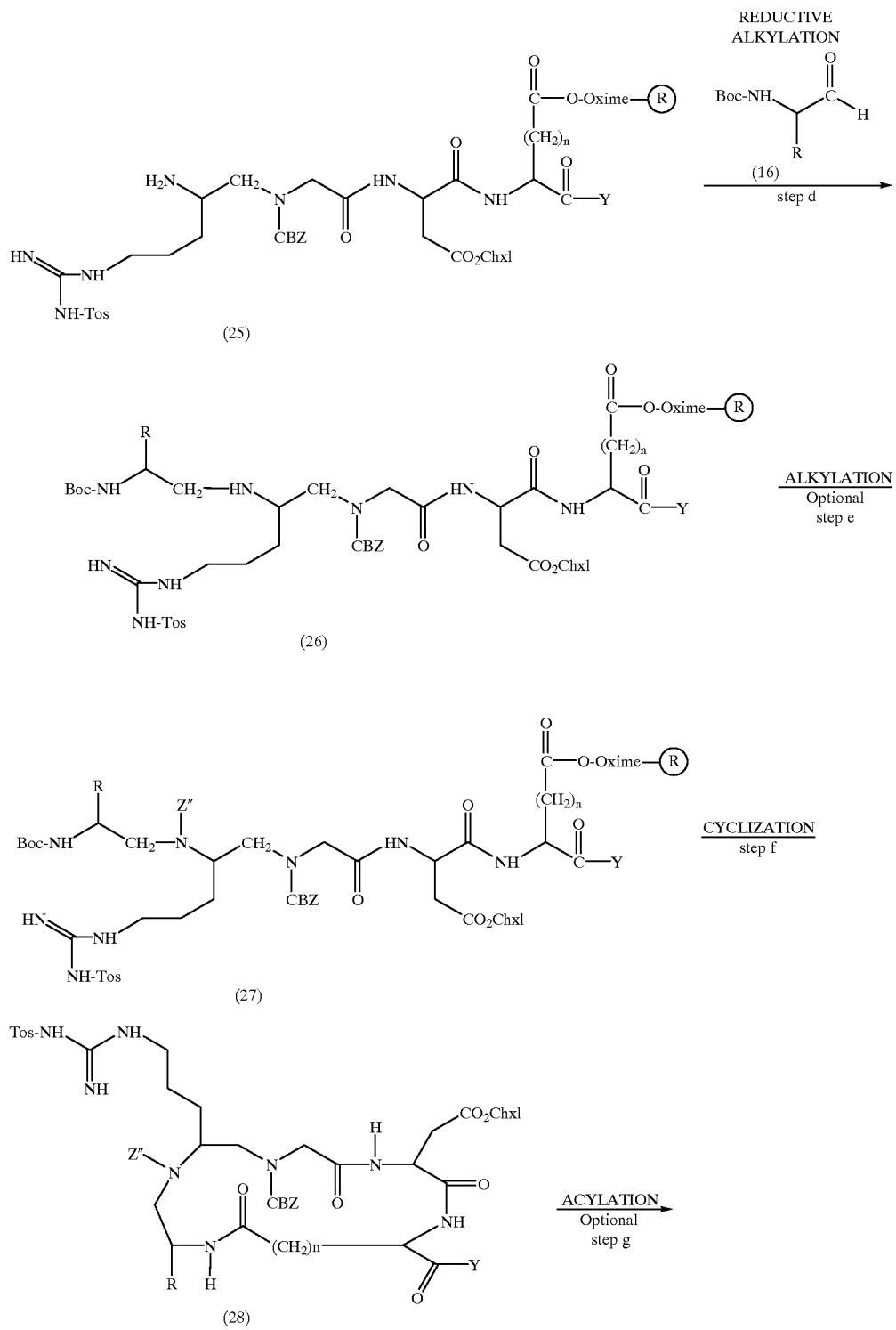

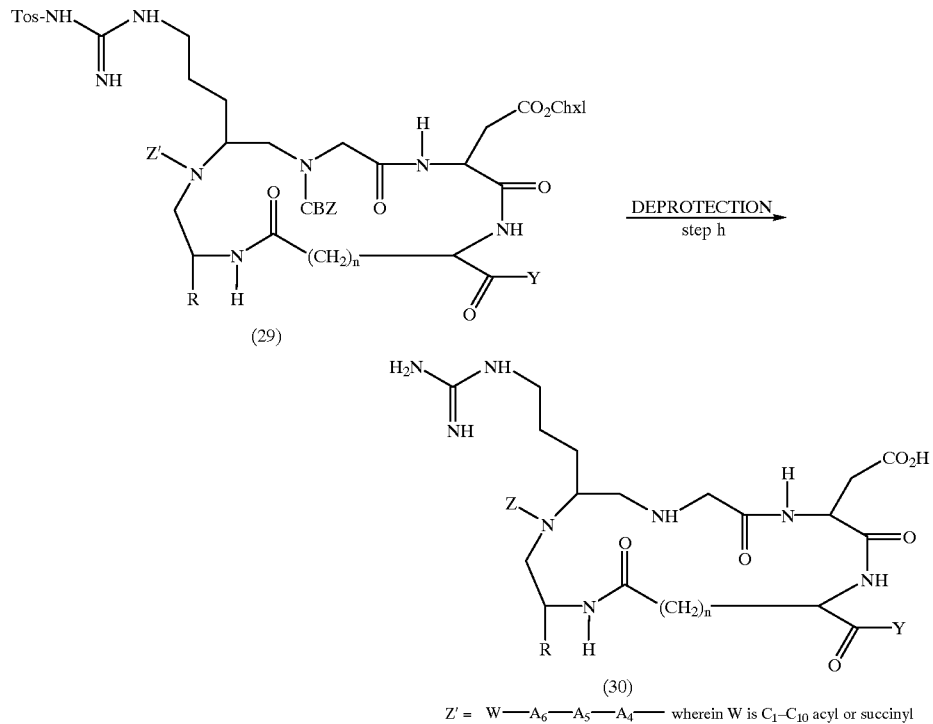

Z' = W—A₆—A₅—A₄— wherein W is $C_1$-$C_{10}$ acyl or succinyl
Z' = W—A₆—A₅—A₄— wherein W is hydrogen or $C_1$-$C_{10}$ alkyl,
—$(CH_2)_mC_6H_5$ or —$(CH_2)_pCO_2H$, m is an integer 1-3, p is an integer 1-4 and A₆, A₅ and A₄ are bonds Scheme B provides a general synthetic procedure for preparing the compounds of formula 1 wherein X is $CH_2NH$.

In step a, the appropriate Gly-Asp(β-Chxl)-amino acid amide oxime resin of structure (12) is coupled with N-Boc-$N^g$-Tos argininal (22) to give the corresponding N-Boc-Arg($N^g$-Tos)Ψ[$CH_2NH$]-Gly-Asp(β-Chxl)-amino acid amide oxime resin of structure (23).

For example, the appropriate Gly-Asp(β-Chxl)-amino acid amide oxime resin of structure (12) is contacted with a molar equivalent of N-Boc-$N^g$-Tos argininal (22) and a molar equivalent of sodium cyanoborohydride. The reactants are typically contacted in a suitable acidic organic solvent mixture such as 1% acetic acid in dimethylformamide. The reactants are typically shaken together at room temperature for a period of time ranging from 1–5 hours. The N-Boc-Arg($N^g$-Tos)Ψ[$CH_2NH$]-Gly-Asp(β-Chxl)-amino acid amide oxime resin of structure (23) is recovered from the reaction zone by filtration and washing with solvent.

In step b, the GlyΨ[$CH_2NH$] functionality of the appropriate N-Boc-Arg($N^g$-Tos)Ψ[$CH_2NH$]-Gly-Asp(β-Chxl)-amino acid amide oxime resin of structure (23) is protected to give the corresponding N-Boc-Arg($N^g$-Tos)Ψ[$CH_2N$-Cbz]-Gly-Asp(β-Chxl)-amino acid amide oxime resin of structure (24).

For example, the appropriate N-Boc-Arg($N^g$-Tos)Ψ[$CH_2NH$]-Gly-Asp(β-Chxl)-amino acid amide oxime resin of structure (23) is contacted with 2.5 molar equivalents of benzyl chloroformate and three molar equivalents of a base, such as triethylamine. The reactants are typically contacted in a suitable organic solvent such as methylene chloride. The reactants are typically stirred together at room temperature for a period of time ranging from 15 minutes to 10 hours.

The N-Boc-Arg($N^g$-Tos)Ψ[$CH_2N$-Cbz]-Gly-Asp(β-Chxl)-amino acid amide oxime resin of structure (24) is recovered from the reaction zone by filtration.

In step c, the N-Boc protecting group of the appropriate N-Boc-Arg($N^g$-Tos)Ψ[$CH_2N$-Cbz]-Gly-Asp(β-Chxl)-amino acid amide oxime resin of structure (24) is cleaved to give the corresponding Arg($N^g$-Tos)Ψ[$CH_2N$-Cbz]-Gly-Asp(β-Chxl)-amino acid amide oxime resin of structure (25) as described previously in Scheme A, step f.

In step d, the appropriate Arg($N^g$-Tos)Ψ[$CH_2N$-Cbz]-Gly-Asp(β-Chxl)-amino acid amide oxime resin of structure (25) is coupled with the appropriate D or L-Boc-NHCHR-aldehyde of structure (16) to give the corresponding Boc-NHCHR-Ψ[$CH_2NH$]-Arg($N^g$-Tos)Ψ[$CH_2N$-Cbz]-Gly-Asp(β-Chxl)-amino acid amide oxime resin of structure (26) as described previously in Scheme A, step k.

In optional step e, the N-Boc-NHCHR-Ψ[$CH_2NH$] functionality of the appropriate N-Boc-NHCHR-Ψ[$CH_2NH$]-Arg($N^g$-Tos)Ψ[$CH_2N$-Cbz]-Gly-Asp(β-Chxl)-amino acid amide oxime resin of structure (26) may be alkylated to give the corresponding N-Boc-NHCHR-Ψ[$CH_2N(Z'')$]-Arg($N^g$-Tos)Ψ[$CH_2N$-Cbz]-Gly-Asp(β-Chxl)-amino acid amide oxime resin of structure (27) wherein Z'' is W—A₆—A₅—A₄— wherein W is $C_1$-$C_{10}$ alkyl, —$(CH_2)_mC_6H_5$ or —$(CH_2)_pCO_2H$ wherein m is an integer 1–3 and p is an integer 1–4 and A₆, A₅ and A₄ are bonds as described previously in Scheme A, optional step 1.

In step f, the appropriate N-Boc-NHCHR-Ψ[$CH_2NH$]-Arg($N^g$-Tos)Ψ[$CH_2N$-Cbz]-Gly-Asp(β-Chxl)-amino acid amide oxime resin of structure (26) or N-Boc-NHCHR-Ψ[$CH_2N(Z'')$]-Arg($N^g$-Tos)Ψ[$CH_2N$-Cbz]-Gly-Asp(β-Chxl)-amino acid amide oxime resin of structure (27) wherein Z'' is W—A₆—A₅—A₄— wherein W is $C_1$-$C_{10}$ alkyl, —$(CH_2)_m C_6H_5$ or —$(CH_2)_pCO_2H$ wherein m is an integer 1–3 and p is an integer 1–4 and $A_6$, $A_5$ and $A_4$ are bonds is cyclized to give the corresponding Cyclo[NHCHR-Ψ[CH$_2$N(Z")]-Arg(N$^g$-Tos)Ψ[CH$_2$N-Cbz]-Gly-Asp(β-Chxl)-amino acid] amide of structure (28) wherein Z" is W—$A_6$—$A_5$—$A_4$— wherein W is hydrogen, $C_1$-$C_{10}$ alkyl, —(CH$_2$)$_m$C$_6$H$_5$ or —(CH$_2$)$_p$CO$_2$H wherein m is an integer 1–3 and p is an integer 1–4 and $A_6$, $A_5$ and A4 are bonds as described previously in Scheme A, step m.

In optional step g, the appropriate Cyclo[NHCHR-Ψ[CH$_2$N(Z")]-Arg(N$^g$-Tos)Ψ[CH$_2$N-Cbz]-Gly-Asp(β-Chxl)-amino acid] amide of structure (28) wherein Z" is W—$A_6$—$A_5$—$A_4$— wherein W is hydrogen and $A_6$, $A_5$ and $A_4$ are bonds may be acylated to give the corresponding Cyclo[NHCHR-Ψ[CH$_2$N(Z')]-Arg(N$^g$-Tos)Ψ[CH$_2$N-Cbz]-Gly-Asp(β-Chxl)-amino acid] amide of structure (29) wherein Z' is W—$A_6$—$A_5$—$A_4$— wherein W is $C_1$-$C_{10}$ acyl or succinyl as described previously in Scheme A, optional step n.

In addition, the appropriate Cyclo[NHCHR-Ψ[CH$_2$N(Z")]-Arg(N$^g$-Tos)Ψ[CH$_2$N-Cbz]-Gly-Asp(β-Chxl)-amino acid] amide of structure (28) wherein Z" is W—$A_6$—$A_5$—$A_4$— wherein W is hydrogen and $A_6$, $A_5$ and $A_4$ are bonds may be converted to the corresponding Cyclo[NHCHR-Ψ[CH$_2$N(Z')]-Arg(N$^g$-Tos)Ψ[CH$_2$N-Cbz]-Gly-Asp(β-Chxl)-amino acid] amide of structure (29) wherein Z' is W—$A_6$—$A_5$—$A_4$— wherein W is hydrogen and at least one of $A_6$, $A_5$ and $A_4$ is an amino acid by standard peptide chemistry as is known in the art. The terminal amino of the peptide side chain A6—A5—A4 may then be acylated as is known in the art to give the corresponding Cyclo[NHCHR-Ψ[CH$_2$N(Z')]-Arg(N$^g$-Tos)Ψ[CH$_2$N-Cbz]-Gly-Asp(β-Chxl)-amino acid] amide of structure (29) wherein Z' is W—$A_6$—$A_5$—$A_4$— wherein W is $C_1$-$C_{10}$ acyl or succinyl and at least one of $A_6$, $A_5$ and $A_4$ is an amino acid.

In step h, the protecting groups of the appropriate Cyclo[NHCHR-Ψ[CH$_2$N(Z")]-Arg(N$^g$-Tos)Ψ[CH$_2$N-Cbz]-Gly-Asp(β-Chxl)-amino acid] amide of structure (28) wherein Z" is W—$A_6$—$A_5$—$A_4$— wherein W is hydrogen, $C_1$-$C_{10}$ alkyl —(CH$_2$)$_m$C$_6$H$_5$ or —(CH$_2$)$_p$CO$_2$H wherein m is an integer 1–3 and p is an integer 1–4 and $A_6$, $A_5$ and $A_4$ are bonds or the appropriate Cyclo[NHCHR-Ψ[CH$_2$N(Z)]-Arg(N$^g$-Tos)Ψ[CH$_2$N-Cbz]-Gly-Asp(β-Chxl)-amino acid] amide] of structure (29) wherein Z' is W—$A_6$—$A_5$—$A_4$— wherein W is hydrogen, $C_1$-$C_{10}$ acyl or succinyl and at least one of $A_6$, $A_5$ and $A_4$ is an amino acid are removed to give the corresponding Cyclo[NHCHR-Ψ[CH$_2$N(Z)]-ArgΨ[CH$_2$NH]-Gly-Asp-amino acid] amide of structure (30) as described previously in Scheme A, step o.

Starting materials for use in Scheme B are readily available to one of ordinary skill in the art. For example, N-Boc-N$^g$-Tos argininal is described by J. M. Maraganore, J. W. Fenton and T. Kline, PCT International Publication Number WO 91/02750, Mar. 7, 1991.

The following examples present typical syntheses as described in Scheme B. These examples are understood to be illustrative only and are not intended to limit the scope of the present invention in any way.

EXAMPLE 10

Cyclo[AlaΨ[CH$_2$NH]-ArgΨ[CH$_2$NH]-Gly-Asp-δ-Glu](NHBn)•CF$_3$CO$_2$H-SEQ ID NO: 36

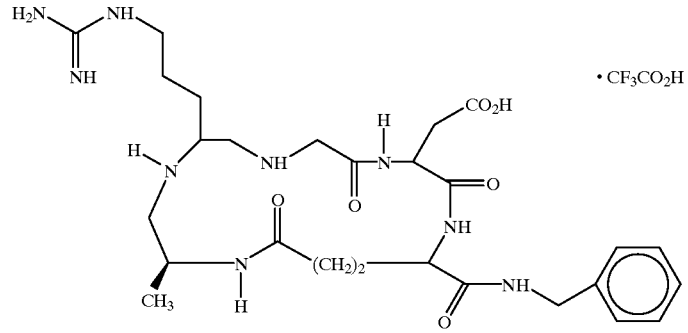

Step a
N$^α$-Boc-Arg(N$^g$-Tos)•[CH$_2$NH]-Gly-Asp(β-Chxl)-Glu(δ-oxime resin)(NHBn)-SEQ ID NO: 37

Dissolve N$^α$-Boc-Ng-Tos argininal (5 mmol) in a solution of 1% acetic acid in dimethylformamide (10 mL). Add Gly-Asp(β-Chxl)-Glu(δ-oxime resin)(NHBn) (0.5 mmol) and sodium cyanoborohydride (150 mg). Shake for 2 hours and filter. Wash with dimethylformamide (3×20 mL), methylene chloride (3×20 mL) and recover the title compound by filtration.

Step b
N$^α$-Boc-Arg(N$^g$-Tos)Ψ[CH$_2$N-Cbz]-Gly-Asp(β-Chxl)-Glu(δ-oxime resin)(NHBn)- SEQ ID NO: 38

Dissolve benzyl chloroformate (5 mmol) in methylene chloride (7 mL) and add N$^α$-Boc-Arg(N$^g$-Tos)Ψ[CH$_2$NH]-Gly-Asp(β-Chxl)-Glu(δ-oxime resin)(NHBn) (SEQ ID NO: 37) (1.0 mmol) followed by triethylamine (0.26 mL, 2.0 mmol). Stir at room temperature for 30 minutes, wash with dimethylformamide (3×20 mL), methylene chloride (3×20 mL) and recover the title compound by filtration.

Step c
Arg(N$^g$-Tos)Ψ[CH$_2$N-Cbz]-Gly-Asp(β-Chxl)-Glu(δ-oxime resin)(NHBn)-SEQ ID NO: 39

Briefly wash N$^α$-Boc-Arg(N$^g$-Tos)Ψ[CH$_2$N-Cbz]-Gly-Asp(β-Chxl)-Glu(δ-oxime resin)(NHBn) (SEQ ID NO: 38) (0.5 mmol) with 50 mL of a solution of 25% trifluoroactic acid in methylene chloride with 1% anisole and filter. Treat with 50 mL of a solution of 25% trifluoroactic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step d
Boc-AlaΨ[CH$_2$NH]-Arg(N$^g$-Tos)Ψ[CH$_2$N(Cbz)]-Gly-Asp(δ-Chxl)-Glu(δ-oxime resin)(NHBn)-SEQ ID NO: 40

Dissolve Boc-Ala-al (5 mmol) in a solution of 1% acetic acid in dimethylformamide (10 mL). Add Arg(N$^g$-Tos)Ψ

[CH₂N-Cbz]-Gly-Asp(β-Chxl)-Glu(δ-oxime resin)(NHBn) (SEQ ID NO: 39) (0.50.5 mmol) and sodium cyanoborohydride (150 mg). Shake for 2 hours and filter. Wash with dimethylformamide (3×20 mL), methylene chloride (3×20 mL) and recover the title compound by filtration.

Step f
Cyclo[AlaΨ[CH₂NH]-Arg(N$^g$-Tos)Ψ[CH₂N-Cbz]-Gly-Asp(δ-Chxl)-δ-Glu](NHBn)-SEQ ID NO: 41

Treat Boc-AlaΨ[CH₂NH]-Arg(N$^g$-Tos)Ψ[CH₂N(Cbz)]-Gly-Asp(δ-Chxl)-Glu(δ-oxime resin)(NHBn) (SEQ ID NO: 40) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step h
Cyclo[AlaΨ[CH₂NH]-ArgΨ[CH₂NH]-Gly-Asp-δ-Glu](NHBn)•CF₃CO₂H-SEQ ID NO: 36

Suspend Cyclo[AlaΨ[CH₂NH]-Arg(N$^g$-Tos)Ψ[CH₂N-Cbz]-Gly-Asp(β-Chxl)-δ-Glu](NHBn) (SEQ ID NO: 41) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

EXAMPLE 11

Cyclo[AlaΨ[CH₂N(CH₃)]-ArgΨ[CH₂NH]-Gly-Asp-δ-Glu](NHBn)•CF₃CO₂H-SEQ ID NO: 42

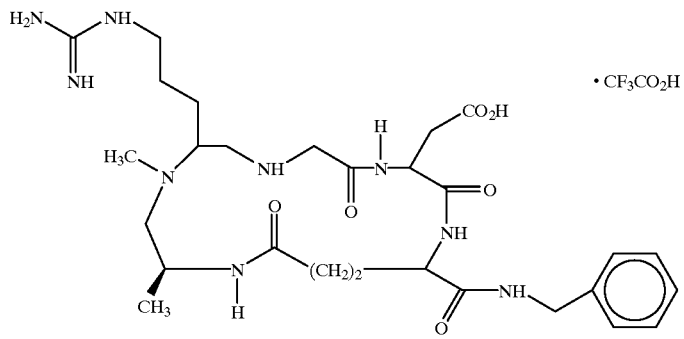

Optional Step e
Boc-AlaΨ[CH₂N(CH₃)]-Arg(N$^g$-Tos)Ψ[CH₂N(Cbz)]-Gly-Asp(β-Chxl)-Glu(δ-oxime resin)(NHBn)-SEQ ID NO: 43

Suspend Boc-AlaΨ[CH₂NH]-Arg(N$^g$-Tos)Ψ[CH₂N(Cbz)]-Gly-Asp(β-Chxl)-Glu(δ-oxime resin)(NHBn) (SEQ ID NO: 40) (5 mmol) in methanol (distilled from Mg) (50 mL) and add formaldehyde (0.405 mL of a 37% solution in water, 5 mmol), sodium cyanoborohydride (0.62 g, 5 mmol) and 1 drop of 1% bromocresol green in methanol. Maintain the pH of the reaction with 1N hydrochloric acid in methanol until the indicator no longer changes and filter. Briefly wash three times with methylene chloride (50 mL) and filter. Briefly wash three times with isopropanol (50 mL) and filter. Briefly wash two times with methylene chloride and filter to give the title compound.

Step f
Cyclo[AlaΨ[CH₂N(CH₃)]-Arg(N$^g$-Tos)Ψ[CH₂N(Cbz)]-Gly-Asp(β-Chxl)-δ-Glu](NHBn)-SEQ ID NO: 44

Treat Boc-AlaΨ[CH₂N(CH₃)]-Arg(N$^g$-Tos)Ψ[CH₂N(Cbz)]-Gly-Asp(β-Chxl)-Glu(δ-oxime resin)(NHBn) (SEQ ID NO: 43) (5 mmol) with 25% triflouroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step h
Cyclo[AlaΨ[CH₂N(CH₃)]-ArgΨ[CH₂NH]-Gly-Asp-δGlu](NHBn)•CF₃CO₂H-SEQ ID NO: 42

Suspend Cyclo[AlaΨ[CH₂N(CH₃)]-Arg(N$^g$-Tos)Ψ[CH₂N(Cbz)]-Gly-Asp(β-Chxl)-δ-Glu](NHBn) (SEQ ID NO: 44) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

The following compounds can be prepared by analogous procedure to those described above in Example 10–11:

Cyclo[D-PheΨ[CH₂NH]-ArgΨ[CH₂NH]-Gly-Asp-δ-Glu]-Leu(NHBn)•TFA;

Cyclo[D-PheΨ[CH₂N(C(O)(CH₂)₂CO₂H)]-ArgΨ[CH₂NH]-Gly-Asp-δ-Glu]-Leu(NHBn)•TFA;

Cyclo[D-PheΨ[CH₂N((CH₂)₃CO₂H)]-ArgΨ[CH₂NH]-Gly-Asp-δ-Glu]-Leu(NHBn)•TFA;

Cyclo[D-PheΨ[CH₂N-Gly-Asp-Ac]-ArgΨ[CH₂NH]-Gly-Asp-δ-Glu]-Leu(NHBn)•TFA;

Cyclo[D-PheΨ[CH₂NH]-ArgΨ[CH₂NH]-Gyl-Asp-δ-Glu]-Asp(NH₂)•TFA;

Cyclo[D-PheΨ[CH₂N(C(O)(CH₂)₂CO₂H)]-ArgΨ[CH₂NH]-Gly-Asp-δ-Glu]-Phe(NH₂)•TFA;

Cyclo[D-PheΨ[CH₂N((CH₂)₃CO₂H)]-ArgΨ[CH₂NH]-Gly-Asp-δ-Glu]-Trp(NH₂)ΨTFA;

Cyclo[D-TyrΨ[CH₂NH]-ArgΨ[CH₂NH]-Gly-Asp-δ-Glu•-Leu(NHBn)]TFA;

Cyclo[D-TyrΨ[CH₂N(C(O)(CH₂)₂CO₂H)]-ArgΨ[CH₂NH]-Gyl-Asp-δ-Glu]-Leu(NHBn)•TFA;

Cyclo[D-TyrΨ[CH₂N((CH₂)₃CO₂H)]-ArgΨ[CH₂NH]-Gly-Asp-δ-Glu]-Leu(NHBn)•TFA;

Cyclo[D-TyrΨ[CH₂N-Gly-Asp-Ac]-ArgΨ[CH₂NH]-Gly-Asp-δ-Glu]-Leu(NHBn)•TFA;

Cyclo[D-TyrΨ[CH₂NH]-ArgΨ[CH₂NH]-Gly-Asp-δ-Gyl-Asp-δ-Glu]-Asp(NH₂)•TFA;
Cyclo[D-TyrΨ[CH₂N(C(O)(CH₂)₂CO₂H)]-ArgΨ[CH₂NH]-Gly-Asp-δ-Glu]-Phe(NH₂)•TFA;
Cyclo[D-PheΨ[CH₂N((CH₂)₃CO₂H)]-ArgΨ[CH₂NH]-Gly-Asp-δ-Glu]-Trp(NH₂)•TFA.

The conformationally restrained peptide analogs of formula 1 wherein X is CH=CH can be prepared by one of ordinary skill in the art. A general synthetic procedure for preparing these compounds is set forth in Scheme C. In Scheme C, all substituents are as previously described unless otherwise indicated.

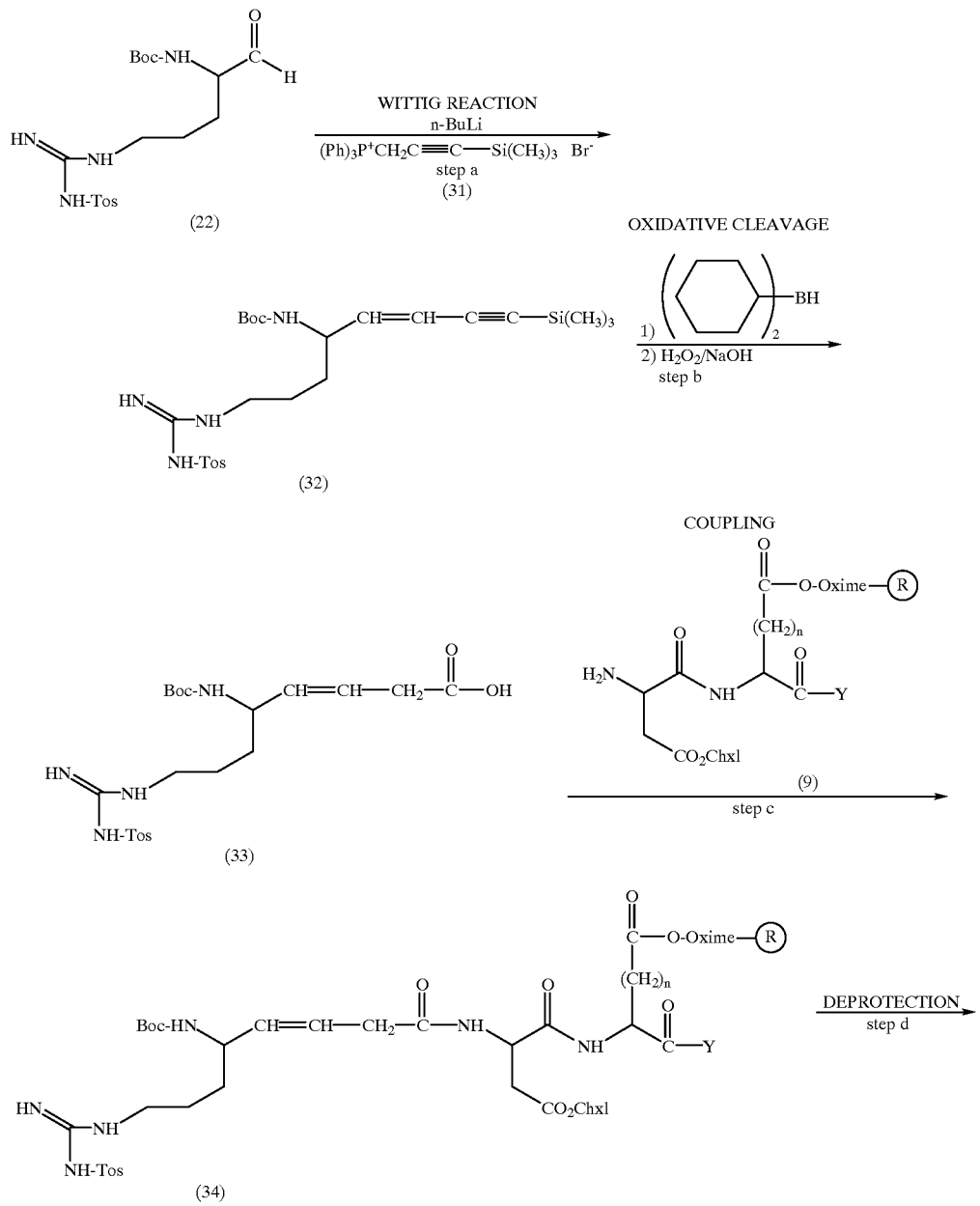

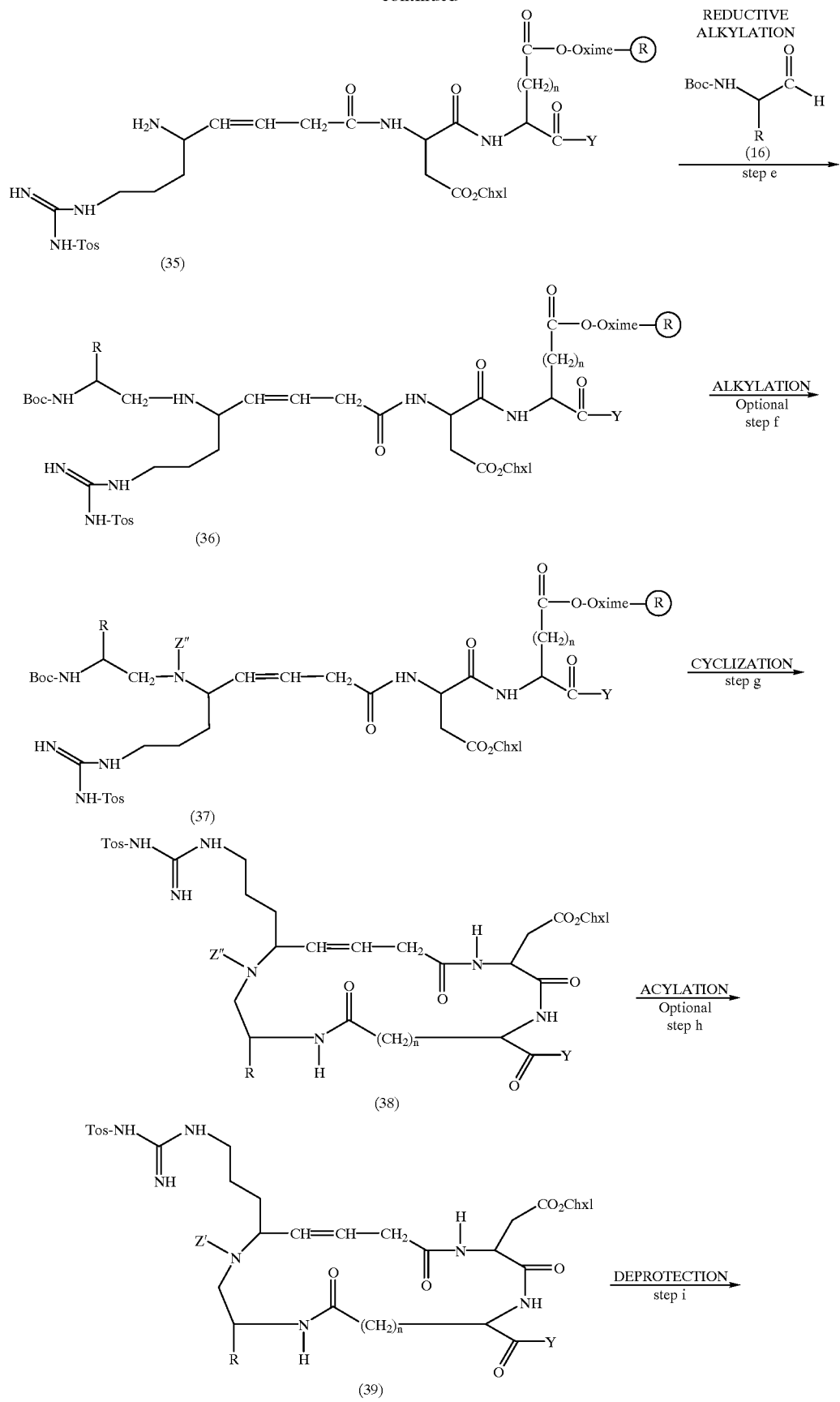

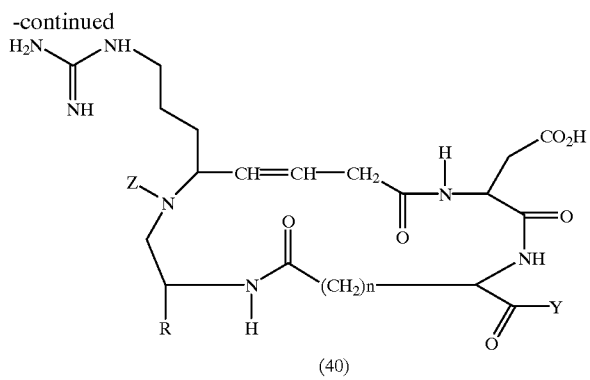

(40)

Z' = W—A₆—A₅—A₄— wherein W is $C_1$–$C_{10}$ acyl or succinyl
Z' = W—A₆—A₅—A₄— wherein W is hydrogen or $C_1$–$C_{10}$ alkyl,
—$(CH_2)_mC_6H_5$ or —$(CH_2)_pCO_2H$, m is an integer 1-3, p is an integer 1-4 and A₆, A₅ and A₄ are bonds Scheme C provides a general synthetic procedure for preparing the compounds of formula 1 wherein X is CH=CH.

In step a, N-Boc-N$^g$-Tos argininal (22) is coupled under Wittig conditions with (3-trimethylsilyl-2-propynyl) triphenylphosphonium bromide (31) to give E-8-(tosylguanidino)-5-(t-butyloxycarbonylamino)-3-ene-trimethylsilyloctyne (32).

For example, (3-trimethylsilyl-2-propynyl) triphenylphosphonium bromide (31) is first contacted with a molar equivalent of a suitable base such as n-butyllithium. The reactants are typically contacted in a suitable anhydrous solvent such as tetrahydrofuran.

The reactants are typically stirred together for a period of time ranging from 5 minutes to 2 hours and at a temperature range of from −78° to 0° C. The resulting intermediate yield is then contacted with a molar equivalent of N-Boc-N$^g$-Tos argininal (22). The reactants are typically stirred together for a period of time ranging from 2–24 hours and at a temperature range of from 0° C. to room temperature. The E-8-(tosylguanidino)-5-(t-butyloxycarbonylamino)-3-ene-trimethylsilyloctyne (32) is recovered from the reaction zone by extractive methods as is known in the art. It may be purified by chromatography.

In step b, E-8-(tosylguanidino)-5-(t-butyloxycarbonylamino)-3-ene-trimethylsilyloctyne (32) is oxidized to give N$^α$-Boc-Arg(N$^g$-Tos)Ψ[E-CH=CH]-Gly (33).

For example, E-8-(tosylguanidino)-5-(t-butyloxycarbonylamino)-3-ene-trimethylsilyloctyne (32) is first contacted with 2 molar equivalents of a reducing agent such as dicyclohexylborane. The reactants are typically contacted in a suitable organic solvent such as tetrahydrofuran. The reactants are typically stirred together at room temperature for a period of time ranging from 2–24 hours. The resulting borane complex is then contacted with a molar excess of appropriate oxidizing agent such as a mixture of aqueous sodium hydroxide/hydrogen perioxide. The reactants are typically stirred together for a period of time ranging from 1 minute to 1 hour and at a temperature range of from −20° to 0° C. The N$^α$-Boc-Arg(N$^g$-Tos)Ψ[E-CH=CH]-Gly (33) is recovered from the reaction zone by exctractive methods as is known in the art. It may be purified by chromatography.

In step c, N$^α$-Boc-Arg(N$^g$-Tos)Ψ[E-CH=CH]-Gly (33) is coupled with the appropriate Asp(β-Chxl)-amino acid amide oxime resin of structure (9) to give the corresponding N$^α$-Boc-Arg(N$^g$-Tos)Ψ[E-CH=CH]-Gly-Asp(β-Chxl)-amino acid amide oxime resin of structure (34).

For example, N$^α$-Boc-Arg(N$^g$-Tos)Ψ[E-CH=CH]-Gly (33) is contacted with two molar equivalents of the appropriate Asp(β-Chxl)-amino acid amide oxime resin of structure (9), two molar equivalents of an activating agent such as a mixture of 1-hydroxybenzotriazole hydrate and 1-(3-dimethylaminopropyl)-3-ethylcarbodiimide hydrochloride and a suitable non-nucleophilic base such as triethylamine or diisopropylethylamine. The reactants are typically contacted in a suitable organic solvent such as methylene chloride or tetrahydrofuran. The reactants are typically stirred together at room temperature for a period of time ranging from 5–24 hours. The N$^α$-Boc-Arg(N$^g$-Tos)Ψ[E-CH=CH]-Gly-Asp (β-Chxl)-amino acid amide oxime resin of structure (34) is recovered from the reaction zone by filtration.

In step d, the N-Boc protecting group of the appropriate N$^α$-Boc-Arg(N$^g$-Tos)Ψ[E-CH=CH]-Gly-Asp(β-Chxl)-amino acid amide oxime resin of structure (34) is cleaved to give the corresponding Arg(N$^g$-Tos)Ψ[E-CH=CH]-Gly-Asp(β-Chxl)-amino acid amide oxime resin of structure (35) as described previously in Scheme A, step f.

In step e, the appropriate Arg(N$^g$-Tos)Ψ[E-CH=CH]-Gly-Asp(β-Chxl)-amino acid amide oxime resin of structure (35) is coupled with the appropriate D or L-N-Boc-NHCHR-aldehyde of structure (16) to give the corresponding N-Boc-NHCHR-Ψ[CH$_2$NH]-Arg(N$^g$-Tos)Ψ[E-CH=CH]-Gly-Asp (β-Chxl)-amino acid amide oxime resin of structure (36) as described previously in Scheme A, step k.

In optional step f, the N-Boc-NHCHR-Ψ[CH$_2$NH] functionality of the appropriate N-Boc-NHCHR-Ψ[CH$_2$NH]-Arg(N$^g$-Tos)Ψ[E-CH=CH]-Gly-Asp(β-Chxl)-amino acid amide oxime resin of structure (36) may be alkylated to give the corresponding N-Boc-NHCHR-Ψ[CH$_2$N(Z")]-Arg(N$^g$-Tos)Ψ[E-CH=CH]-Gly-Asp(β-Chxl)-amino acid amide oxime resin of structure (37) wherein Z" is W—A₆—A₅—A₄— wherein W is $C_1$–$C_{10}$ alkyl, —$(CH_2)_mC_6H_5$ or —$(CH_2)_pCO_2H$ wherein m is an integer 1–3 and p is an integer 1–4 and A₆, A₅ and A₄ are bonds as described previously in Scheme A, optional step l.

In step g, the appropriate N-Boc-NHCHR-Ψ[CH$_2$NH]-Arg(N$^g$-Tos)Ψ[E-CH=CH]-Gly-Asp(β-Chxl)-amino acid amide oxime resin of structure (36) or N-Boc-NHCHR-Ψ[CH$_2$N(Z")]-Arg(N$^g$-Tos)Ψ[E-CH=CH]-Gly-Asp(β-Chxl)-amino acid amide oxime resin of structure (37) wherein Z" is W—A₆—A₅—A₄— wherein W is $C_1$–$C_{10}$ alkyl, —$(CH_2)_mC_6H_5$ or —$(CH_2)_pCO_2H$ wherein m is an integer 1–3 and p is an integer 1–4 and $A_6$, $A_5$ and $A_4$ are bonds is cyclized to give the corresponding Cyclo[NHCHR-Ψ[CH$_2$N(Z")]-Arg(N$^g$-Tos)Ψ[E-CH═CH]-Gly-Asp(β-Chxl)-amino acid] amide of structure (38) wherein Z" is W—$A_6$—$A_5$—$A_4$— wherein W is hydrogen, $C_1$–$C_{10}$ alkyl, —(CH$_2$)$_m$C$_6$H$_5$ or —(CH$_2$)$_p$CO$_2$H wherein m is an integer 1–3 and p is an integer 1–4 and $A_6$, $A_5$ and $A_4$ are bonds as described previously in Scheme A, step m.

In optional step h, the appropriate Cyclo[NHCHR-Ψ[CH$_2$N(Z")]-Arg(N$^g$-Tos)Ψ[E-CH═CH]-Gly—Asp(β-Chxl)-amino acid] amide of structure (38) wherein Z" is W—$A_6$—$A_5$—$A_4$— wherein W is hydrogen and $A_6$, $A_5$ and $A_4$ are bonds may be acylated as is known in the art to give the corresponding Cyclo[NHCHR-Ψ[CH$_2$N(Z')]-Arg(N$^g$-Tos)Ψ[E-CH═CH]-Gly—Asp(β-Chxl)-amino acid] amide of structure (39) wherein Z' is W—$A_6$—$A_5$—$A_4$— wherein W is $C_1$–$C_{10}$ acyl or succinyl and $A_6$, $A_5$ and $A_4$ are bonds.

In addition, the appropriate Cyclo[NHCHR-Ψ[CH$_2$N(Z")]-Arg(N$^g$-Tos)Ψ[E-CH═CH]-Gly-Asp(β-Chxl)-amino acid] amide of structure (38) wherein Z" is W—$A_6$—$A_5$—$A_4$— wherein W is hydrogen and $A_6$, $A_5$ and $A_4$ are bonds may be converted to the corresponding Cyclo[NHCHR-Ψ[CH$_2$N(Z')]-Arg(N$^g$-Tos)Ψ[E-CH═CH]-Gly—Asp(β-Chxl)-amino acid] amide of structure (39) wherein Z' is W—$A_6$—$A_5$—$A_4$— wherein W is hydrogen and at least one of $A_6$, $A_5$ and $A_4$ is an amino acid by standard peptide chemistry as is known in the art. The terminal amino of the peptide side chain $A_6$—$A_5$—$A_4$ may then be acylated as is known in the art to give the corresponding Cyclo[NHCHR-Ψ[CH$_2$N(Z')]-Arg(N$^g$-Tos)Ψ[E-CH═CH]-Gly-Asp(β-Chxl)-amino acid] amide of structure (39) wherein Z' is W—$A_6$—$A_5$—$A_4$— wherein W is $C_1$–$C_{10}$ acyl or succinyl and at least one of $A_6$, $A_5$ and $A_4$ is an amino acid.

In step i, the protecting groups of the appropriate Cyclo [NHCHR-Ψ[CH$_2$N(Z")]-Arg(N$^g$-Tos)Ψ[E-CH═CH]-Gly-Asp(β-Chxl)-amino acid] amide of structure (38) wherein Z" is W—$A_6$—$A_5$—$A_4$— wherein W is hydrogen, $C_1$–$C_{10}$ alkyl, (CH$_2$)$_m$C$_6$H$_5$ or —(CH$_2$)$_p$CO$_2$H wherein m is an integer 1–3 and p is an integer 1–4 and $A_6$, $A_5$ and $A_4$ are bonds or the appropriate Cyclo[NHCHR-Ψ[CH$_2$N(Z)]-Arg (N$^g$-Tos)Ψ[E-CH═CH]-Gly-Asp(β-Chxl)-amino acid] amide of structure (39) wherein Z' is W—$A_6$—$A_5$—$A_4$— wherein W is hydrogen, $C_1$–$C_{10}$ acyl or succinyl and at least one of $A_6$, $A_5$ and $A_4$ is an amino acid are removed to give the corresponding Cyclo[NHCHR-Ψ[CH$_2$N(Z)]-ArgΨ[E-CH═CH]-Gly-Asp-amino acid] amide of structure (40) as described previously in Scheme A, step o.

Starting materials for use in Scheme C are readily available to one of ordinary skill in the art.

The following example presents a typical synthesis as described above in Scheme C. This example is understood to be illustrative only and is not intended to limit the scope of the present invention in any way.

EXAMPLE 12

Cyclo[AlaΨ[CH$_2$NH]-ArgΨ[E-CH═CH]-Gly-Asp-δ-Glu](NHBn)•CF$_3$CO$_2$H-SEQ ID NO: 45

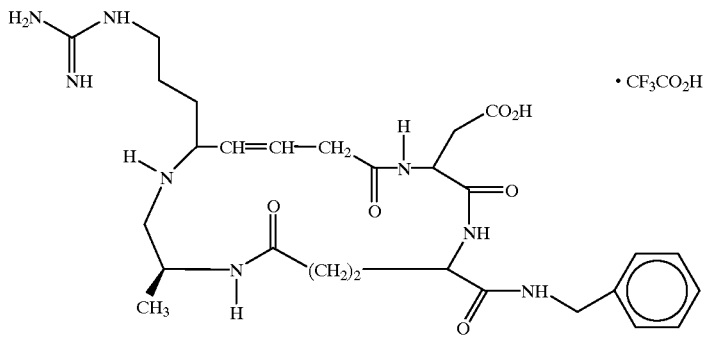

Step a
E-8-(Tosylguanidino)-5-(t-butyloxycarbonylamino)-3-ene-trimethylsilyloctyne Dissolve (3-trimethylsilyl-2-propynyl) triphenylphosphonium bromide (24 mmol) in anhydrous tetrahydrofuran (250 mL), cool to –78° C. and place under an argon atmosphere. Add a solution of n-butyllithium in hexane (16.3 mL, 26 mmol). Stir at –78° C. for 10 minutes, then add, by dropwise addition, a solution of N$^α$-Boc-Arg (N$^ε$-Tos)-al (20 mmol) in tetrahydrofuran (5 mL). Stir for 10 minutes, allow to warm to room temperature, and stir for an additional 17 hours. Dilute with saturated ammonium chloride (100 mL), wash twice with 10% sodium hydroxide and dry (MgSO$_4$). Evaporate the solvent in vacuo to give the title compound.

Step b
N$^α$-Boc-Arg(N$^g$-Tos)Ψ[E-CH═CH]-Gly

Dissolve cyclohexene (9.035 g, 0.11 mol) in tetrahydrofuran (3 mL) and cool to –15° C. Slowly add borane (24.1 mL of a 2.3M solution in tetrahydrofuran) and stir at –15° C. for 1 hour to give dicyclohexylborane (55 mmol).

Add a 0° C. solution of E-8-(Tosylguanidino)-5-(t-5 butyloxycarbonylamino)-3-ene-trimethylsilyloctyne (25 mmol) in tetrahydrofuran (15 mL) and stir at room temperature until the reaction mixture becomes homogeneous. Cool to 0° C., dilute with 3N sodium hydroxide (25 mL) and immediately oxidize by adding 30% hydrogen peroxide (2 mL). Saturate with potassium carbonate, acidify the aqueous phase with 1N hydrochloric acid and decant the upper phase.

Extract the aqueous phase with ethyl ether (2×), dry (MgSO$_4$) and evaporate the solvent in vacuo to give the title compound.

Step c
N$^α$-Boc-Arg(N$^g$-Tos)Ψ[E-CH═CH]-Gly-Asp(β-Chxl)-Glu (δ-oxime resin)(NHBn)-SEQ ID NO: 46

Mix Asp(β-Chxl)-Glu(δ-oxime resin)(NHBn) (10 mmol), N$^α$-Boc-Arg(N$^g$-Tos)Ψ[E-CH═CH]-Gly (5.3 mmol), hydroxybenztriazole (1.65 g, 11 mmol) and 1-(3-dimethylaminopropyl)-3-ethyl carbodiimide hydrochloride (2.1 g, 11 mmol). Add a solution of diisopropylethylamine (3.8 mL) in methylene chloride (20 mL) and stir at room temperature for several hours. Briefly wash two times with 5 mL of a solution of 1% diisopropylethylamine in methylene chloride and filter to give the title compound.

Step d
Arg(N$^g$-Tos)Ψ[E-CH=CH]-Gly-Asp(β-Chxl)-Glu(δ-oxime resin)(NHBn)-SEQ ID NO: 47

Briefly wash N$^α$-Boc-Arg(N$^g$-Tos)Ψ[E-CH=CH]-Gly-Asp(β-Chxl)-Glu(δ-oxime resin)(NHBn) (SEQ ID NO: 46) (2 mmol) with 50 mL of a solution of 25% trifluoroactic acid in methylene chloride with 1% anisole and filter. Treat with 50 mL of a solution of 25% trifluoroactic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step e
Boc-AlaΨ[CH$_2$NH]-Arg(N$^g$-Tos)Ψ[E-CH=CH]-Gly-Asp(β-Chxl)-Glu(δ-oxime resin)(NHBn)-SEQ ID NO: 48

Dissolve Boc-Ala-al (5 mmol) in a solution of 1% acetic acid in dimethylformamide (10 mL). Add Arg(N$^g$-Tos)Ψ[E-CH=CH]-Gly-Asp(β-Chxl)-Glu(δ-oxime resin)(NHBn) (SEQ ID NO: 47) (0.5 mmol) and sodium cyanoborohydride (150 mg). Shake for 2 hours and filter. Wash with dimethylformamide (3×20 mL), methylene chloride (3×20 mL) and filter to give the title compound.

Step g
Cyclo[AlaΨ[CH$_2$NH]-Arg(N$^g$-Tos)Ψ[E-CH=CH]-Gly-Asp(β-Chxl)-δ-Glu](NHBn)-SEQ ID NO: 49

Treat Boc-AlaΨ[CH$_2$NH]-Arg(N$^g$-Tos)Ψ[E-CH=CH]-Gly-Asp(β-Chxl)-Glu(δ-oxime resin)(NHBn) (SEQ ID NO: 48) (5 mmol) with 25% trifluoroacetic acid in methylene chloride (25 mL) for 25 minutes. Wash with methylene chloride (3×20 mL), isopropanol (3×20 mL), methylene chloride (2 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step i
Cyclo[AlaΨ[CH$_2$NH]ArgΨ[E-CH=CH]-Gly-Asp-δ-Glu](NHBn)•CF$_3$CO$_2$H-SEQ ID NO: 45

Suspend Cyclo[AlaΨ[CH$_2$NH]-Arg(N$^g$-Tos)Ψ[E-CH=CH]-Gly-Asp(β-Chxl)-δ-Glu](NHBn) (SEQ ID NO: 49) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

The following compounds may be prepared by analogous procedures to those described above in Example 12:

Cyclo[D-PheΨ[CH$_2$NH]-ArgΨ[E-CH=CH]-Gly-Asp-δ-Glu]-Leu(NHBn)•TFA;

Cyclo[D-PheΨ[CH$_2$N(C(O)(CH$_2$)$_2$CO$_2$H)]-ArgΨ[(E-CH=CH]-Gly-Asp-δ-Glu]-Leu(NHBn)•TFA;

Cyclo[D-PheΨ[CH$_2$N((CH$_2$)$_3$CO$_2$H)]-ArgΨ[E-CH=CH]-Gly-Asp-δ-Glu]-Leu(NHBn)•TFA;

Cyclo[D-PheΨ[CH$_2$N-Gly-Asp-Ac]-ArgΨ[E-CH=CH]-Gly-Asp-δ-Glu]-Leu(NHBn)•TFA;

Cyclo[D-PheΨ[CH$_2$NH]-ArgΨ[[E-CH=CH]-Gly-Asp-δ-Glu]-Asp(NH$_2$)•TFA;

Cyclo[D-PheΨ[CH$_2$N(C(O)(CH$_2$)$_2$CO$_2$H)]-ArgΨ[E-CH=CH]-Gly-Asp-δ-Glu]-Phe(NH$_2$)•TFA;

Cyclo[D-PheΨ[CH$_2$N((CH$_2$)$_3$CO$_2$H)]-ArgΨ[E-CH=CH]-Gly-Asp-δ-Glu]-Trp(NH$_2$)•TFA;

Cyclo[D-TyrΨ[CH$_2$NH]-ArgΨ[E-CH=CH]-Gly-Asp-δ-Glu]-Leu(NHBn)•TFA;

Cyclo[D-TyrΨ[CH$_2$N(C(O)(CH$_2$)$_2$CO$_2$H)]-ArgΨ[E-CH=CH]-Gly-Asp-δ-Glu]-Leu(NHBn)•TFA;

Cyclo[D-TyrΨ[CH$_2$N((CH$_2$)$_3$CO$_2$H)]-ArgΨ[E-CH=CH]-Gly-Asp-δ-Glu]-Leu(NHBn)•TFA;

Cyclo[D-TyrΨ(CH$_2$N-Gly-Asp-Ac]-ArgΨ[E-CH=CH]-Gly-Asp-δ-Glu]-Leu(NHBn)•TFA;

Cyclo[D-TyrΨ[CH$_2$NH]-ArgΨ[E-CH=CH]-Gly-Asp-δ-Glu]-Asp(NH$_2$)•TFA;

Cyclo[D-TyrΨ[CH$_2$N(C(O)(CH$_2$)$_2$CO$_2$H)]-ArgΨ[E-CH=CH]-Gly-Asp-δ-Glu]-Phe(NH$_2$)•TFA;

Cyclo[D-PheΨ[CH$_2$N((CH$_2$)$_3$CO$_2$H)]-ArgΨ[E-CH=CH]-Gly-Asp-δ-Glu]-Trp(NH$_2$)•TFA.

The conformationally restrained peptides of formula 1 wherein X is CH$_2$CH$_2$ can be prepared by one of ordinary skill in the art. A general synthetic procedure for preparing these compounds is set forth in Scheme D. In Scheme D, all substituents are as previously described unless otherwise indicated.

Scheme D

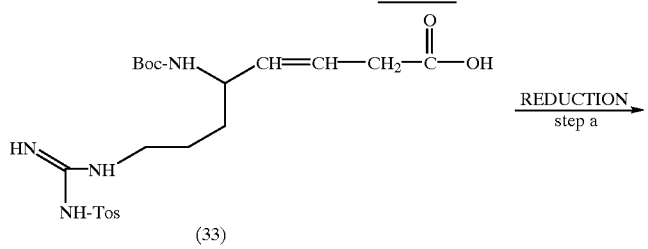

(33)

-continued
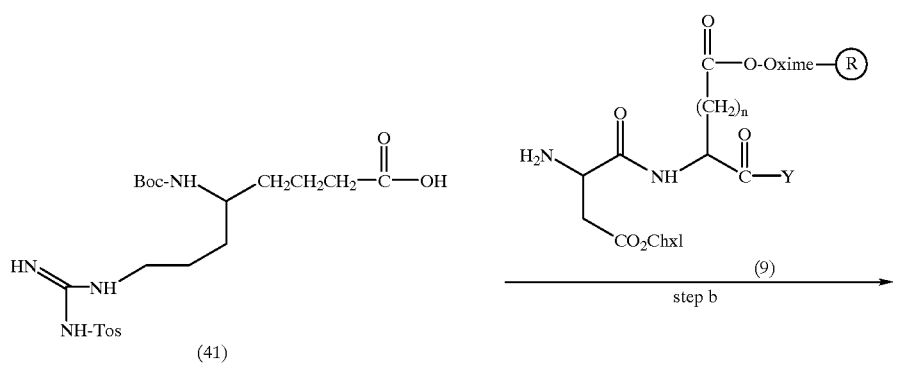
(41)
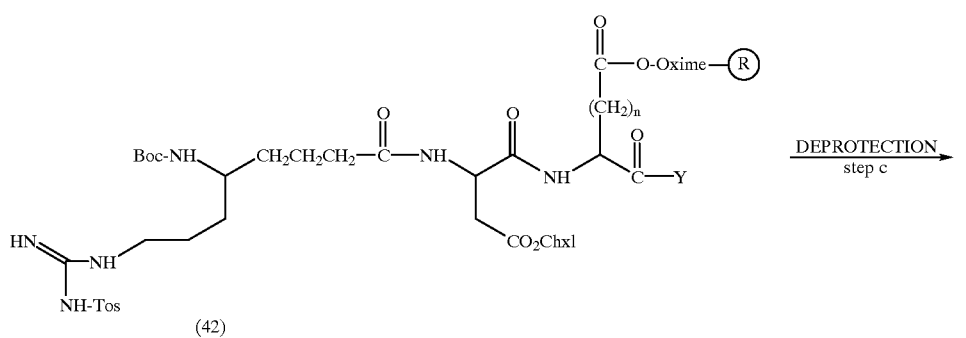
(42)
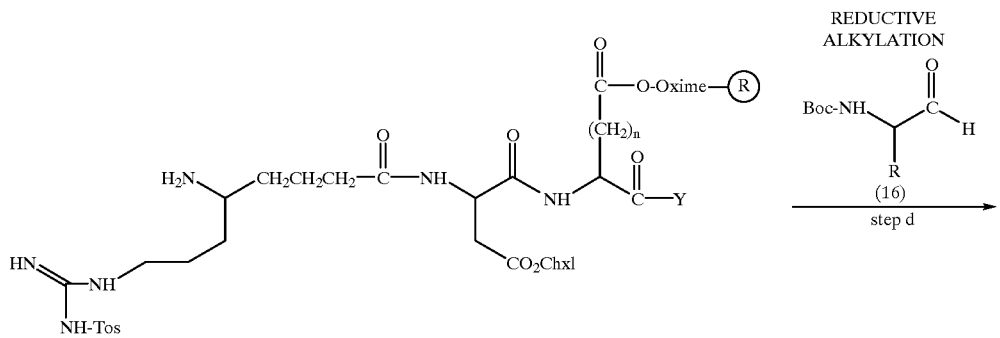
(43)
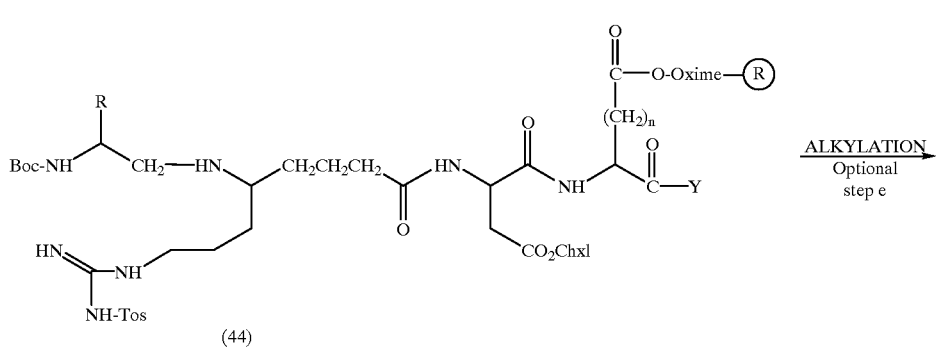
(44)

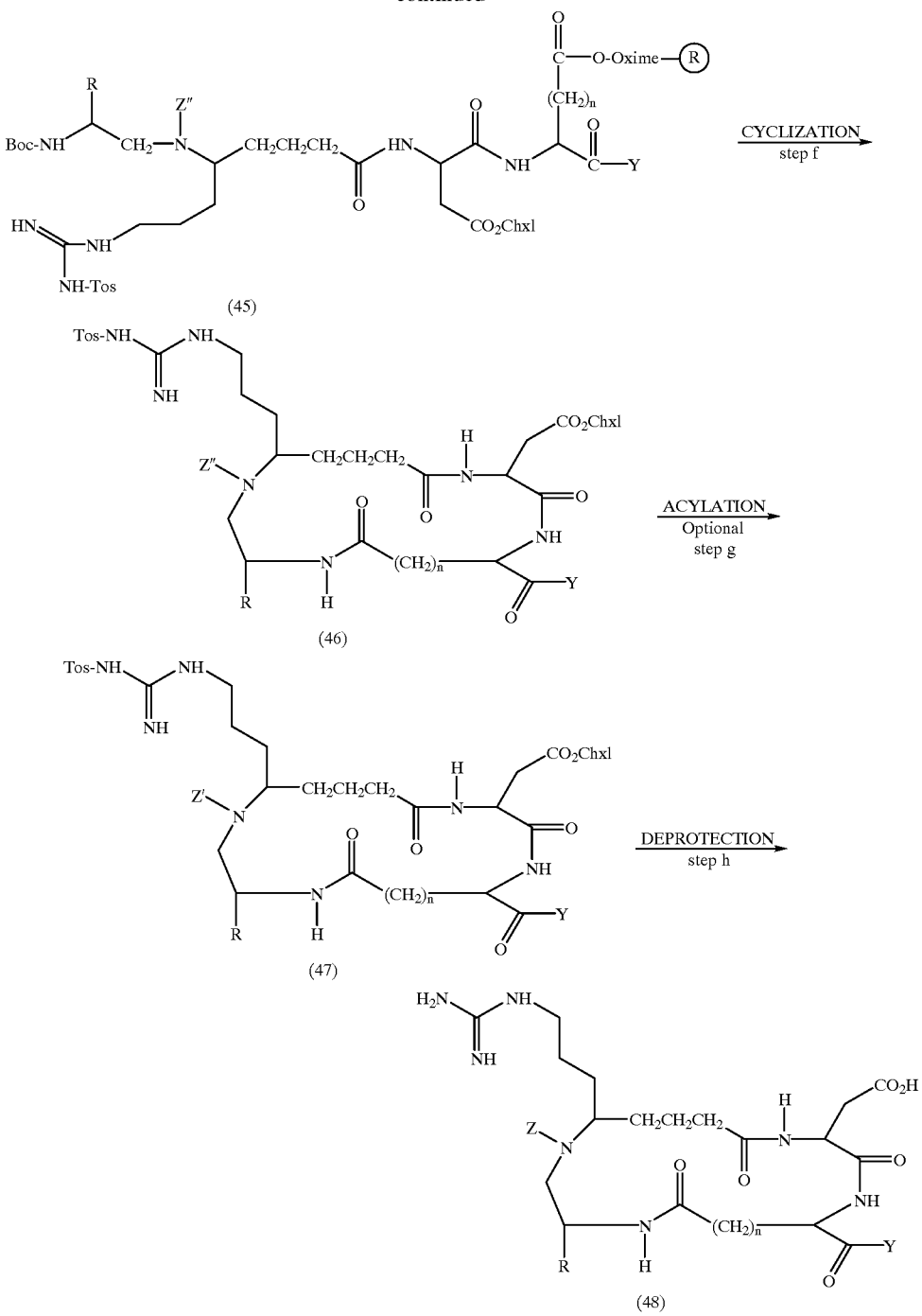

Scheme D provides a general synthetic procedure for preparing the compounds of formula 1 wherein X is $CH_2CH_2$.

In step a, the olefin functionality of the appropriate $N^\alpha$-Boc-Arg($N^g$-Tos)Ψ[E-CH=CH]-Gly (33) is reduced to give the corresponding $N^\alpha$-Boc-Arg($N^g$-Tos)Ψ[$CH_2CH_2$]-Gly (41).

For example, the appropriate $N^\alpha$-Boc-Arg($N^g$-Tos)Ψ[E-CH=CH]-Gly (33) is contacted with a catalytic amount with a suitable hydrogenation catalyst such as palladium/carbon. The reactants are typically contacted in a suitable protic solvent such as methanol. The reactants are shaken at room temperature under an atmosphere of hydrogen at a pressure range of from 35–50 psi. The $N^\alpha$-Boc-Arg($N^g$-Tos)

Ψ[CH₂CH₂]-Gly (41) is recovered from the reaction zone by filtration and evaporation of the solvent.

In step b, N$^\alpha$-Boc-Arg(N$^g$-Tos)Ψ[CH₂CH₂]-Gly (41) is coupled with the appropriate Asp(β-Chxl)-amino acid amide oxime resin of structure (9) to give the corresponding N$^\alpha$-Boc-Arg(N$^g$-Tos)Ψ[CH₂CH₂]-Gly-Asp(β-Chxl)-amino acid amide oxime resin of structure (42) as described previously in Scheme C, step c.

In step c, the N-Boc protecting group of the appropriate N$^\alpha$-Boc-Arg(N$^g$-Tos)Ψ[CH₂CH₂]-Gly-Asp(β-Chxl)-amino acid amide oxime resin of structure (42) is cleaved to give the corresponding Arg(N$^g$-Tos)Ψ[CH₂CH₂]-Gly-Asp(β-Chxl)-amino acid amide oxime resin of structure (43) as described previously in Scheme A, step f.

In step d, the appropriate Arg(N$^g$-Tos)Ψ[CH₂CH₂]-Gly-Asp(β-Chxl)-amino acid amide oxime resin of structure (43) is coupled with the appropriate D or L-N-Boc-NHCHR-aldehyde of structure (16) to give the corresponding N-Boc-NHCHR-Ψ[CH₂NH]-Arg(N$^g$-Tos)Ψ[CH₂CH₂]-Gly-Asp(β-Chxl)-amino acid amide oxime resin of structure (44) as described previously in Scheme A, step k.

In optional step e, the N-Boc-NHCHR-Ψ[CH₂NH] functionality of the appropriate N-Boc-NHCHR-Ψ[CH₂NH]-Arg(N$^g$-Tos)Ψ[CH₂CH₂]-Gly-Asp(β-Chxl)-amino acid amide oxime resin of structure (44) may be alkylated to give the corresponding N-Boc-NHCHR-Ψ[CH₂N(Z")]-Arg(N$^g$-Tos)Ψ[CH₂CH₂]-Gly-Asp(β-Chxl)-amino acid amide oxime resin of structure (45) wherein Z" is W—A₆—A₅—A₄— wherein W is C₁–C₁₀ alkyl, —(CH₂)$_m$C₆H₅ or —(CH₂)$_p$CO₂H wherein m is an integer 1–3 and p is an integer 1–4 and A₆, A₅ and A₄ are bonds as described previously in Scheme A, optional step l.

In step f, the appropriate N-Boc-NHCHR-Ψ[CH₂NH]-Arg(N$^g$-Tos)Ψ[CH₂CH₂]-Gly-Asp(β-Chxl)-amino acid amide oxime resin of structure (44) or N-Boc-NHCHR-Ψ[CH₂N(Z")]-Arg(N$^g$-Tos)Ψ[CH₂CH₂]-Gly-Asp(β-Chxl)-amino acid amide oxime resin of structure (45) wherein Z" is W—A₆—A₅—A₄— wherein W is C₁–C₁₀ alkyl, —(CH₂)$_m$ C₆H₅ or —(CH₂)$_p$CO₂H wherein m is an integer 1–3 and p is an integer 1–4 and A₆, A₅ and A₄ are bonds is cyclized to give the corresponding Cyclo[NHCHR-Ψ[CH₂N(Z")]-Arg(N$^g$-Tos)Ψ[CH₂CH₂]-Gly—Asp(β-Chxl)-amino acid] amide of structure (46) wherein Z" is W—A₆—A₅—A₄— wherein W is hydrogen, C₁–C₁₀ alkyl, —(CH₂)$_m$C₆H₅ or —(CH₂)$_p$CO₂H wherein m is an integer 1–3 and p is an integer 1–4 and A₆, A₅ and A₄ are bonds as described previously in Scheme A, step m.

In optional step g, the appropriate Cyclo[NHCHR-Ψ[CH₂N(Z")]-Arg(N$^g$-Tos)Ψ[CH₂CH₂]-Gly-Asp(β-Chxl)-amino acid] amide of structure (46) wherein Z" is W—A₆—A₅—A₄— wherein W is hydrogen and A₆, A₅ and A₄ are bonds may be acylated as is known in the art to give the corresponding Cyclo[NHCHR-Ψ[CH₂N(Z')]-Arg(N$^g$-Tos)Ψ[CH₂CH₂]-Gly-Asp(β-Chxl)-amino acid] amide of structure (47) wherein Z' is W—A₆—A₅—A₄— wherein W is C₁–C₁₀ acyl or succinyl and A₆, A₅ and A₄ are bonds.

In addition, the appropriate Cyclo[NHCHR-Ψ[CH₂N(Z")]-Arg(N$^g$-Tos)Ψ[CH₂CH₂]-Gly-Asp(β-Chxl)-amino acid] amide of structure (46) wherein Z" is W—A₆—A₅—A₄— wherein W is hydrogen and A₆, A₅ and A₄ are bonds may be converted to the corresponding Cyclo[NHCHR-Ψ[CH₂N(Z')]-Arg(N$^g$-Tos)Ψ[CH₂CH₂]-Gly-Asp(β-Chxl)-amino acid] amide of structure (47) wherein Z' is W—A₆—A₅—A₄— wherein W is hydrogen and at least one of A₆, A₅ and A₄ is an amino acid by standard peptide chemistry as is known in the art. The terminal amino of the peptide side chain A₆—A₅—A₄ may then be acylated as is known in the art to give the corresponding Cyclo[NHCHR-Ψ[CH₂N(Z')]-Arg(N$^g$-Tos)Ψ[CH₂CH₂]-Gly-Asp(β-Chxl)-amino acid] amide of structure (47) wherein Z' is W—A₆—A₅—A₄— wherein W is C₁–C₁₀ acyl or succinyl and at least one of A₆, A₅ and A₄ is an amino acid.

In step h, the protecting groups of the appropriate Cyclo[NHCHR-Ψ[CH₂N(Z")]-Arg(N$^g$-Tos)Ψ[CH₂CH₂]-Gly-Asp(β-Chxl)-amino acid] amide of structure (46) wherein Z" is W—A₆—A₅—A₄— wherein W is hydrogen, C₁–C₁₀ alkyl, —(CH₂)$_m$C₆H₅ or —(CH₂)$_p$CO₂H wherein m is an integer 1–3 and p is an integer 1–4 and A₆, A₅ and A₄ are bonds or the appropriate Cyclo[NHCHR-Ψ[CH₂N(Z')]-Arg(N$^g$-Tos)Ψ[CH₂CH₂]-Gly-Asp(β-Chxl)-amino acid] amide of structure (47) wherein Z' is W—A₆—A₅—A₄— wherein W is hydrogen, C₁–C₁₀ acyl or succinyl and at least one of A₆, A₅ and A₄ is an amino acid are removed to give the corresponding Cyclo[NHCHR-Ψ[CH₂N(Z)]-Arg(N$^g$-Tos)Ψ[CH₂CH₂]-Gly-Asp(β-Chxl)-amino acid] amide of structure (47) as described previously in Scheme A, step o.

Starting materials for use in Scheme D are readily available to one of ordinary skill in the art.

The following example presents a typical synthesis as described above in Scheme D. This example is understood to be illustrative only and is not intended to limit the scope of the present invention in any way.

EXAMPLE 13

Cyclo[AlaΨ[CH₂NH]-ArgΨ[CH₂CH₂]-Gly-Asp-δ-Glu](NHBn)·CF₃CO₂H-SEQ ID NO: 50

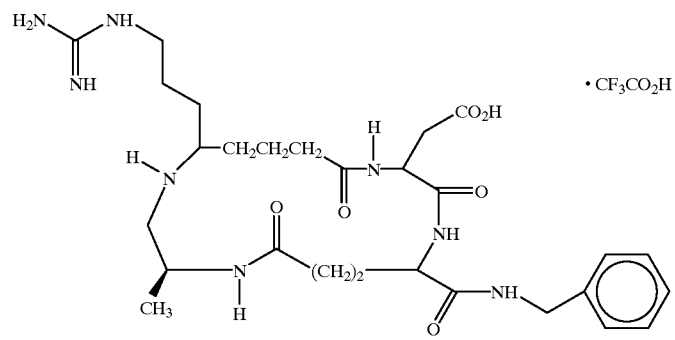

Step a
N$^\alpha$-Boc-Arg(N$^g$-Tos)Ψ[CH$_2$CH$_2$]-Gly

Dissolve N$^\alpha$-Boc-Arg(N$^g$-Tos)Ψ[E-CH=CH]-Gly (5.5 mmol) in methanol (50 mL) and place in a Paar hydrogenation flask. Add 10% palladium/C (500 mg). Charge the vessel to 50 psi and shake for 18 hours. Filter through Celite and remove the solvent in vacuo to give the title compound.

Step b
N$^\alpha$-Boc-Arg(N$^g$-Tos)Ψ[CH$_2$CH$_2$]-Gly-Asp(β-Chxl)-Glu(δ-oxime resin)(NHBn)-SEQ ID NO: 51

Mix Asp(β-Chxl)-Glu(δ-oxime resin)(NHBn) (10 mmol), N$^\alpha$-Boc-Arg(N$^g$-Tos)Ψ[CH$_2$CH$_2$]-Gly (10 mmol), hydroxybenztriazole (1.65 g, 11 mmol) and 1-(3-dimethylaminopropyl)-3-ethyl carbodiimide hydrochloride (2.1 g, 11 mmol). Add a solution of diisopropylethylamine (3.8 mL) in methylene chloride (20 mL) and stir at room temperature for several hours. Briefly wash two times with 50 mL of a solution of 1% diisopropylethylamine in methylene chloride and filter to give the title compound.

Step c
Arg(N$^g$-Tos)Ψ[CH$_2$CH$_2$]-Gly-Asp(β-Chxl)-Glu(δ-oxime resin)(NHBn)-SEQ ID NO: 52

Briefly wash N$^\alpha$-Boc-Arg(N$^g$-Tos)Ψ[CH$_2$CH$_2$]-Gly-Asp (β-Chxl)-Glu(δ-oxime resin)(NHBn) (SEQ ID NO: 51) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step d
Boc-AlaΨ[CH$_2$NH]-Arg(N$^g$-Tos)Ψ[CH$_2$CH$_2$]-Gly-Asp(β-Chxl)-Glu(δ-oxime resin)(NHBn)-SEQ ID NO: 53

Dissolve Boc-Ala-al (5 mmol) in a solution of 1% acetic acid in dimethylformamide (10 mL). Add Arg(N$^g$-Tos)Ψ [CH$_2$CH$_2$]-Gly-Asp(β-Chxl)-Glu(δ-oxime resin)(NHBn) (SEQ ID NO: 52) (0.5 mmol) and sodium cyanoborohydride (150 mg). Shake for 2 hours and filter. Wash with dimethylformamide (3×2 mL), methylene chloride (3×2 mL) and filter to give the title compound.

Step f
Cyclo[AlaΨ[CH$_2$NH]-Arg(N$^g$-Tos)Ψ[CH$_2$CH$_2$]-Gly-Asp (β-Chxl)-δ-Glu](NHBn)-SEQ ID NO: 54

Treat Boc-AlaΨ[CH$_2$NH]-Arg(N$^g$-Tos)Ψ[CH$_2$CH$_2$]-Gly-Asp(β-Chxl)-Glu(δ-oxime resin)(NHBn) (SEQ ID NO: 53) (0.5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step h
Cyclo[AlaΨ[CH$_2$NH]-ArgΨ[CH$_2$CH$_2$]-Gly-Asp-δ-Glu] (NHBn)•CF$_3$CO$_2$H-SEQ ID NO: 50

Suspend Cyclo[AlaΨ[CH$_2$NH]-Arg(N$^g$-Tos)Ψ [CH$_2$CH$_2$]-Gly-Asp(β-Chxl)-δ-Glu](NHBn) (SEQ ID NO: 54) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

The following compounds can be prepared by analogous procedures to those described above in Example 13:

Cyclo[D-PheΨ[CH$_2$NH]-ArgΨ[CH$_2$CH$_2$]-Gly-Asp-δ-Glu]-Leu(NHBn)•TFA;

Cyclo[PheΨ[CH$_2$N(C(O)(CH$_2$)$_2$CO$_2$H)]-ArgΨ[CH$_2$CH$_2$]-Gly-Asp-δ-Glu]-Leu(NHBn)•TFA;

Cyclo[D-PheΨ[CH$_2$N((CH$_2$)$_3$CO$_2$H)]-ArgΨ[CH$_2$CH$_2$]-Gly-Asp-δ-Glu]-Leu(NHBn)•TFA;

Cyclo[D-PheΨ[CH$_2$N-Gly-Asp-Ac]-ArgΨ[CH$_2$CH$_2$]-Gly-Asp-δ-Glu]Leu(NHBn)•TFA;

Cyclo[D-PheΨ[CH$_2$NH]-ArgΨ[CH$_2$CH$_2$]-Gly-Asp-δ-Glu]-Asp(NH$_2$)•TFA;

Cyclo[D-PheΨ[CH$_2$N(C(O)(CH$_2$)$_2$CO$_2$H)]-ArgΨ [CH$_2$CH$_2$]-Gly-Asp-δ-Glu]-Phe(NH$_2$)•TFA;

Cyclo[D-PheΨ[CH$_2$N((CH$_2$)$_3$CO$_2$H)]-ArgΨ[CH$_2$CH$_2$]-Gly-Asp-δ-Glu]-Trp(NH$_2$)•TFA;

Cyclo[D-TyrΨ[CH$_2$NH]-ArgΨ[CH$_2$CH$_2$]-Gly-Asp-δ-Glu]-Leu(NHBn)•TFA;

Cyclo[D-TyrΨ[CH$_2$N(C(O)(CH$_2$)$_2$CO$_2$H)]-ArgΨ [CH$_2$CH$_2$]-Gly-Asp-δ-Glu]-Leu(NHBn)•TFA;

Cyclo[D-TyrΨ[CH$_2$N((CH$_2$)$_3$CO$_2$H)]-ArgΨ[CH$_2$CH$_2$]-Gly-Asp-δ-Glu]-Leu(NHBn)•TFA;

Cyclo[D-TyrΨ[CH$_2$N-Gly-Asp-Ac]-ArgΨ[CH$_2$CH$_2$]-Gly-Asp-δ-Glu]-Leu(NHBn)•TFA;

Cyclo[D-TyrΨ[CH$_2$NH]-ArgΨ[CH$_2$CH$_2$]-Gly-Asp-δ-Glu]-Asp(NH$_2$)•TFA;

Cyclo[D-TyrΨ[CH$_2$N(C(O)(CH$_2$)$_2$CO$_2$H)]-ArgΨ [CH$_2$CH$_2$]-Gly-Asp-δ-Glu]-Phe(NH$_2$)•TFA;

Cyclo[D-PheΨ[CH$_2$N((CH$_2$)$_3$CO$_2$H)]-ArgΨ[CH$_2$CH$_2$]-Gly-Asp-δ-Glu]-Trp(NH$_2$)•TFA.

The conformationally restrained peptides of formula 1 wherein X is COCH$_2$ can be prepared by one of ordinary skill in the art. A general synthetic procedure for preparing these compounds is set forth in Scheme E. In Scheme E, all substituents are as previously described unless otherwise indicated.

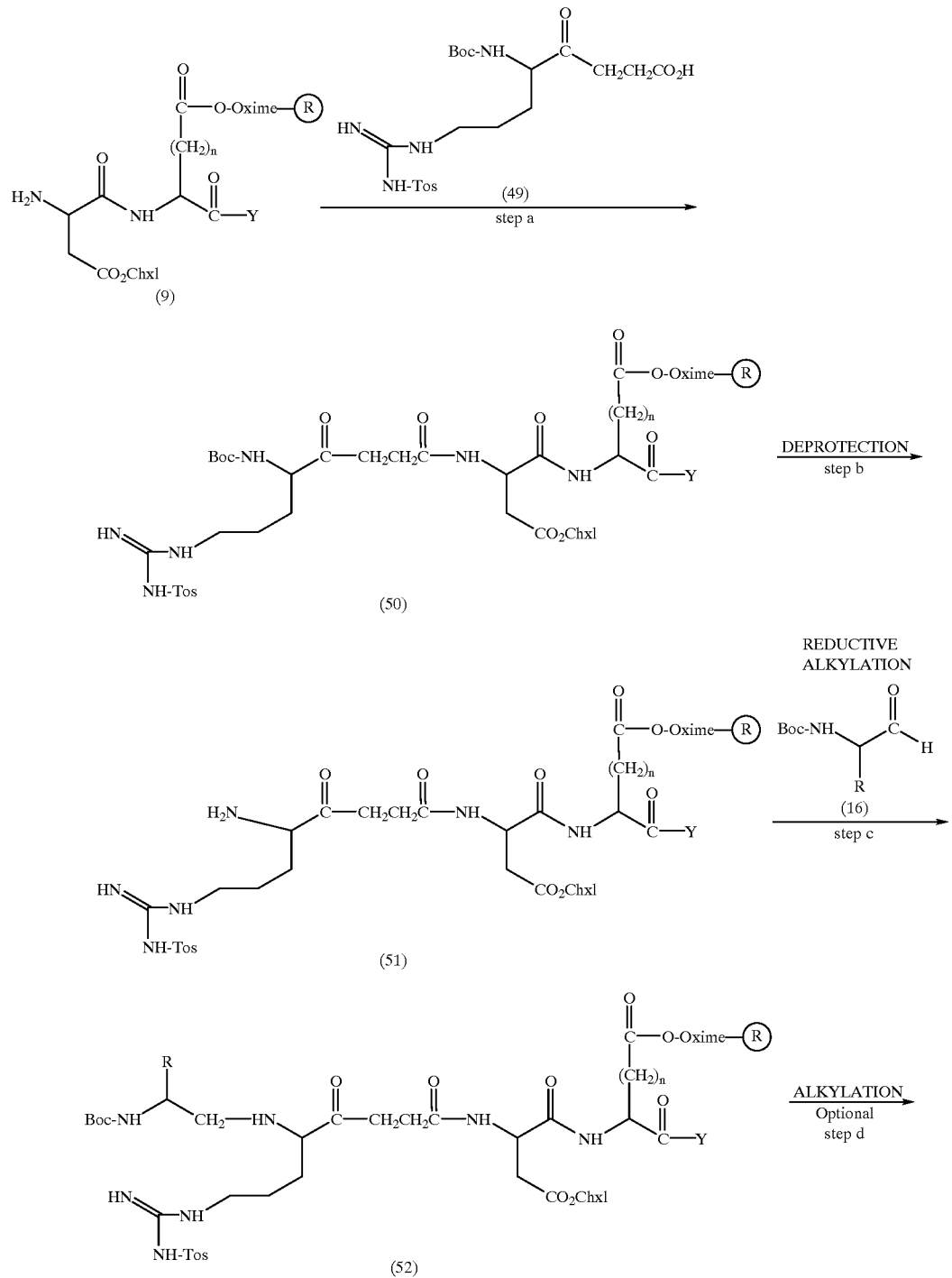

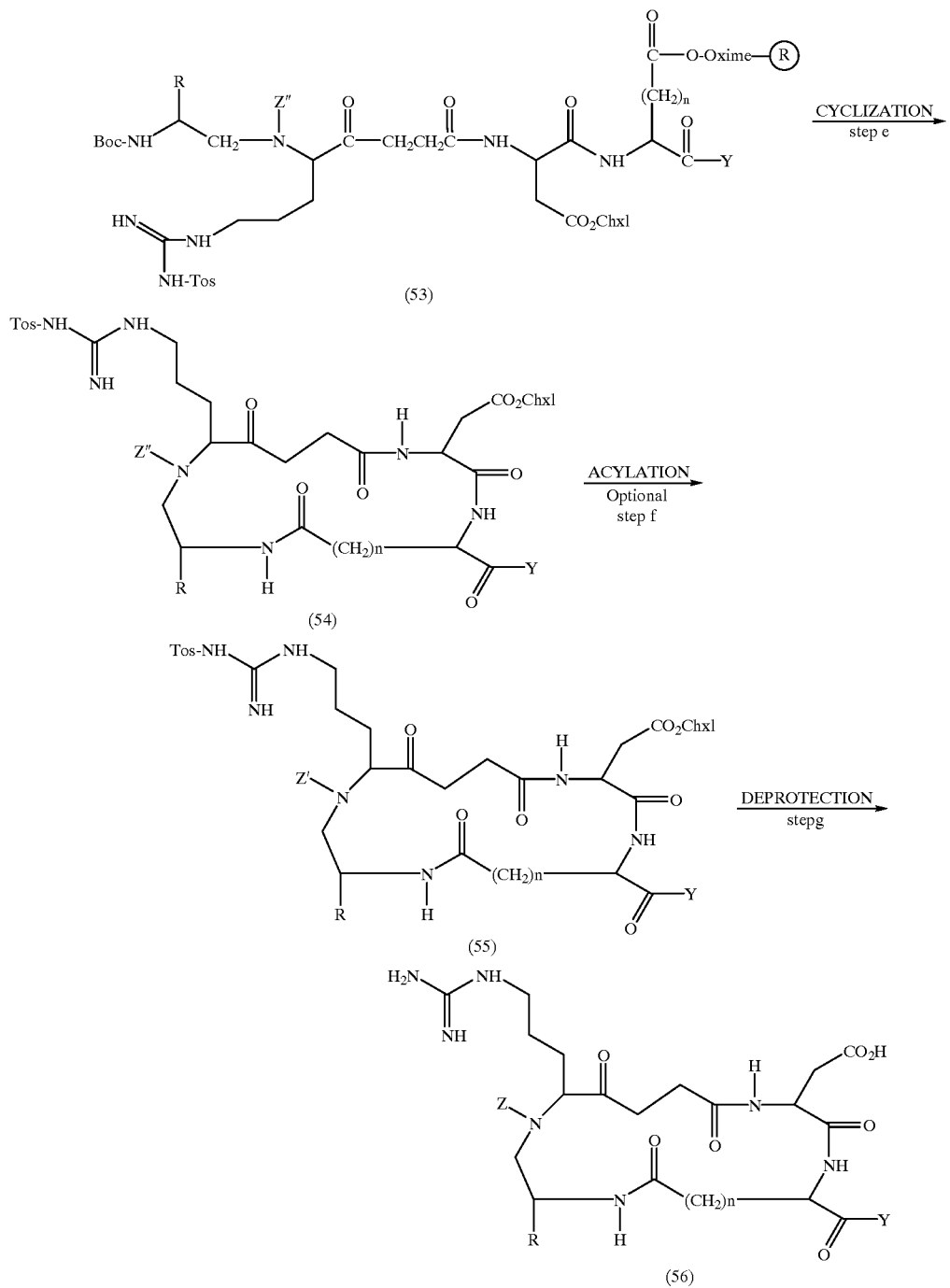

Scheme E provides a general synthetic procedure for preparing the compounds of formula 1 wherein X is $COCH_2$.

In step a, the appropriate Asp(β-Chxl)-amino acid amide oxime resin of structure (9) is coupled with $N^\alpha$-Boc-Arg($N^g$-Tos)Ψ[$COCH_2$]-Gly-OH (49) to give the corresponding $N^\alpha$-Boc-Arg($N^g$-Tos)Ψ[$COCH_2$]-Gly-Asp(β-Chxl)-amino acid amide oxime resin of structure (50) as described previously in Scheme D, step b.

In step b, the N-Boc protecting group of the appropriate $N^\alpha$-Boc-Arg($N^g$-Tos)Ψ[$COCH_2$]-Gly-Asp(β-Chxl)-amino acid amide oxime resin of structure (50) is cleaved to give the corresponding Arg($N^g$-Tos)Ψ[$COCH_2$]-Gly-Asp(β-

Chxl)-amino acid amide oxime resin of structure (51) as described previously in Scheme A, step f.

In step c, the appropriate Arg($N^g$-Tos)Ψ[COCH$_2$]-Gly-Asp(β-Chxl)-amino acid amide oxime resin of structure (51) is coupled with the appropriate D or L-N-Boc-NHCHR-aldehyde of structure (16) to give the corresponding N-Boc-NHCHR-Ψ[CH$_2$NH]-Arg($N^g$-Tos)Ψ[COCH$_2$]-Gly-Asp(β-Chxl)-amino acid amide oxime resin of structure (52) as described previously in Scheme A, step k.

In optional step d, the N-Boc-NHCHR-Ψ[CH$_2$NH] functionality of the appropriate N-Boc-NHCHR-Ψ[CH$_2$NH]-Arg($N^g$-Tos)Ψ[COCH$_2$]-Gly-Asp(β-Chxl)-amino acid amide oxime resin of structure (52) may be alkylated to give the corresponding N-Boc-NHCHR-Ψ[CH$_2$N(Z")]-Arg($N^g$-Tos)Ψ[COCH$_2$]-Gly-Asp(β-Chxl)-amino acid amide oxime resin of structure (53) wherein Z" is W—A$_6$—A$_5$—A$_4$— wherein W is C$_1$-C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds as described previously in Scheme A, optional step l.

In step e, the appropriate N-Boc-NHCHR-Ψ[CH$_2$NH]-Arg($N^g$-Tos)Ψ[COCH$_2$]-Gly-Asp(β-Chxl)-amino acid amide oxime resin of structure (52) or N-Boc-NHCHR-Ψ[CH$_2$N(Z")]-Arg($N^g$-Tos)Ψ[COCH$_2$]-Gly-Asp(β-Chxl)-amino acid amide oxime resin of structure (53) wherein Z" is W—A$_6$—A$_5$—A$_4$— wherein W is C$_1$-C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds is cyclized to give the corresponding Cyclo[NHCHR-Ψ[CH$_2$N(Z")]-Arg($N^g$-Tos)Ψ[COCH$_2$]-Gly-Asp(β-Chxl)-amino acid] amide of structure (54) wherein Z" is W—A$_6$—A$_5$—A$_4$— wherein W is hydrogen, C$_1$-C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds as described previously in Scheme A, step m.

In optional step f, the appropriate Cyclo[NHCHR-Ψ[CH$_2$N(Z")]-Arg($N^g$-Tos)Ψ[COCH$_2$]-Gly-Asp(β-Chxl)-amino acid] amide of structure (54) wherein Z" is W—A$_6$—A$_5$—A$_4$— wherein W is hydrogen and A$_6$, A$_5$ and A$_4$ are bonds may be acylated as is known in the art to give the corresponding Cyclo[NHCHR-Ψ[CH$_2$N(Z')]-Arg($N^g$-Tos)Ψ[COCH$_2$]-Gly-Asp(β-Chxl)-amino acid] amide of structure (55) wherein Z' is W—A$_6$—A$_5$—A$_4$— wherein W is C$_1$-C$_{10}$ acyl or succinyl and A$_6$, A$_5$ and A$_4$ are bonds.

In addition, the appropriate Cyclo[NHCHR-Ψ[CH$_2$N(Z")]-Arg($N^g$-Tos)Ψ[COCH$_2$]-Gly-Asp(β-Chxl)-amino acid] amide of structure (54) wherein Z" is W—A$_6$—A$_5$—A$_4$— wherein W is hydrogen and A$_6$, A$_5$ and A$_4$ are bonds may be converted to the corresponding Cyclo[NHCHR-Ψ[CH$_2$N(Z')]-Arg($N^g$-Tos)Ψ[COCH$_2$]-Gly-Asp(β-Chxl)-amino acid] amide of structure (55) wherein Z' is W—A$_6$—A$_5$—A$_4$— wherein W is hydrogen and at least one of A$_6$, A$_5$ and A$_4$ is an amino acid by standard peptide chemistry as is known in the art. The terminal amino of the peptide side chain A$_6$—A$_5$—A$_4$ may then be acylated as is known in the art to give the corresponding Cyclo[NHCHRΨ[CH$_2$N(Z')]-Arg($N^g$-Tos)Ψ[COCH$_2$]-Gly-Asp(β-Chxl)-amino acid] amide of structure (55) wherein Z' is W—A$_6$—A$_5$—A$_4$— wherein W is C$_1$-C$_{10}$ acyl or succinyl and at least one of A$_6$, A$_5$ and A$_4$ is an amino acid.

In step g, the protecting groups of the appropriate Cyclo[NHCHR-Ψ[CH$_2$N(Z")]-Arg($N^g$-Tos)Ψ[COCH$_2$]-Gly-Asp(β-Chxl)-amino acid] amide of structure (54) wherein Z" is W—A$_6$—A$_5$—A$_4$— wherein W is hydrogen, C$_1$-C$_{10}$ alkyl, —(CH$_2$)$_m$C$_6$H$_5$ or —(CH$_2$)$_p$CO$_2$H wherein m is an integer 1–3 and p is an integer 1–4 and A$_6$, A$_5$ and A$_4$ are bonds or the appropriate Cyclo[NHCHR-Ψ[CH$_2$N(Z)]-Arg($N^g$-Tos)Ψ[COCH$_2$]-Gly-Asp(β-Chxl)-amino acid] amide of structure (55) wherein Z' is W—A$_6$—A$_5$—A$_4$— wherein W is hydrogen, C$_1$-C$_{10}$ acyl or succinyl and at least one of A$_6$, A$_5$ and A$_4$ is an amino acid are removed to give the corresponding Cyclo[NHCHR-Ψ[CH$_2$N(Z)]-ArgΨ[COCH$_2$]-Gly-Asp-amino acid] amide of structure (56) as described previously in Scheme A, step o.

Starting materials for use in Scheme E are readily available to one of ordinary skill in the art.

The following example presents a typical sythesis as described in Scheme E. This example is understood to be illustrative only and is not intended to limit the scope of the present invention in any way.

EXAMPLE 14

Cyclo[AlaΨ[CH$_2$NH]-ArgΨ[COCH$_2$]-Gly-Asp-δ-Glu](NHBn)•CF$_3$CO$_2$H-SEQ ID NO: 55

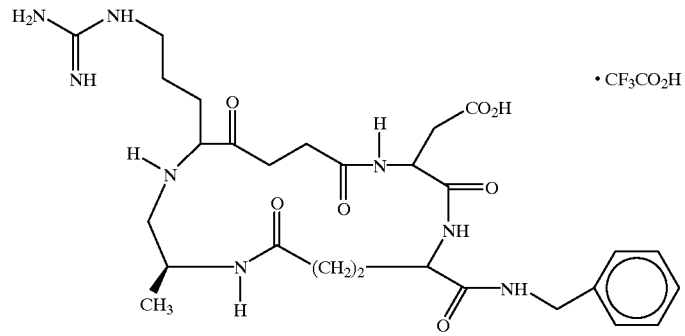

Step a

Boc-Arg($N^g$-Tos)Ψ[COCH$_2$]-Gly-Asp(β-Chxl)-Glu(δ-oxime resin)(NHBn)-SEQ ID NO: 56

Suspend $N^\alpha$-Boc-Arg($N^g$-Tos) (1.0 mmol) in benzene (4 mL) and add N-methylmorpholine (252 mg, 2.5 mmol). Cool to −22° C. and add isobutylchloroformate (136 mg, 1.0 mmol). Stir for 20 minutes and slowly add to a solution of excess diazomethane (previously prepared from 8.7 g of nitrosomethylurea and dried for several hours at 0° C. over potassium hyroxide pellets). Stir at 0° C. for several hours and remove residual benzene and diazomethane on a steam-bath in the hood. Evaporate the residual benzene in vacuo to give $N^\alpha$-Boc-Arg($N^g$-Tos)-CHN$_2$.

Dissolve $N^\alpha$-Boc-Arg($N^g$-Tos)-CHN$_2$ in anhydrous ethyl ether (5 mL) and treat with a slight excess of hydrochloric acid in dioxane. Evaporate the solvent on a steam bath then in vacuo to give $N^\alpha$-Boc-Arg($N^g$-Tos)-CH$_2$Cl.

Mix N$^\alpha$-Boc-Arg(N$^g$-Tos)-CH$_2$Cl (0.485 mmol), dimethylformamide (40 mL) and sodium iodide (10 g). Reflux for 8 hours, cool and add methylene chloride (40 mL). Filter and evaporate the filtrate to a residue. Partition the residue between methylene chloride (2 mL) and water (2 mL). Separate the organic phase, dry (MgSO$_4$) and evaporate the solvent in vacuo to give N$^\alpha$-Boc-Arg(N$^g$-Tos)-CH$_2$I.

Suspend sodium hydride (1 g, 0.21 mmol) in tetrahydrofuran, place under a nitrogen atmosphere and cool to 0° C. Add, by dropwise addition, dibenzyl malonate (0.2 mmol). Stir at 0° C. until anion formation is complete and add N$^\alpha$-Boc-Arg(N$^g$-Tos)-CH$_2$I (0.21 mmol). Heat at reflux for several hours, cool and pour into water (40 mL). Extract with ethyl acetate (3×60 mL), dry (MgSO$_4$) and evaporate the solvent in vacuo to give N$^\alpha$-Boc-Arg(N$^g$-Tos)-CH$_2$CH(CO$_2$CH$_2$Ph)$_2$.

Mix N$^\alpha$-Boc-Arg(N$^g$-Tos)-CH$_2$CH(CO$_2$CH$_2$Ph)$_2$ (5.3 mmol) and 10% palladium/carbon (0.5 g) in 95% ethanol (40 mL). Hydrogenate at room temperature at atmospheric pressure. Filter and evaporate the filtrate in vacuo to give N$^\alpha$-Boc-Arg(N$^g$-Tos)-CH$_2$CH(CO$_2$H)$_2$.

Suspend N$^\alpha$-Boc-Arg(N$^g$-Tos)-CH$_2$CH(CO$_2$H)$_2$ (0.2 mmol) in acetonitrile (80 mL) and treat with copper(I) oxide (1.5 mg, 0.01 mmol). Heat at reflux for 7 hours. Cool, filter and evaporate the solvent in vacuo. Take the residue up in ethyl ether (10 mL) and wash with 10% hydrochloric acid (2×5 mL), water (5 mL) and brine (5 mL). Dry (MgSO$_4$) and evaporate the solvent in vacuo to give N$^\alpha$-Boc-Arg(N$^g$-Tos)Ψ[COCH$_2$]-Gly.

Mix Asp(β-Chxl)-Glu(δ-oxime resin)(NHBn) (10 mmol), N$^\alpha$-Boc-Arg(N$^g$-Tos)Ψ[COCH$_2$]-Gly (5.3 mmol), hydroxybenztriazole (1.65 g, 11 mmol) and 1-(3-dimethylaminopropyl)-3-ethyl carbodiimide hydrochloride (2.1 g, 11 mmol). Add a solution of diisopropylethylamine (3.8 mL) in methylene chloride (20 mL) and stir at room temperature for several hours. Briefly wash two times with 50 mL of a solution of 1% diisopropylethylamine in methylene chloride and filter to give the title compound.

Step b

Arg(N$^g$-Tos)Ψ[COCH$_2$]-Gly-Asp(β-Chxl)-Glu(δ-oxime resin)(NHBn)-SEQ ID NO: 57

Briefly wash Boc-Arg(N$^g$-Tos)Ψ[COCH$_2$]-Gly-Asp(β-Chxl)-Glu(δ-oxime resin)(NHBn) (SEQ ID NO: 56) (0.5 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step c

Boc-AlaΨ[CH$_2$NH]-Arg(N$^g$-Tos)Ψ[COCH$_2$]-Gly-Asp(β-Chxl)-Glu(δ-oxime resin)(NHBn)-SEQ ID NO: 58

Dissolve Boc-Ala-al (5 mmol) in a solution of 1% acetic acid in dimethylformamide (10 mL). Add Arg(N$^g$-Tos)Ψ[COCH$_2$]-Gly-Asp(β-Chxl)-Glu(δ-oxime resin)(NHBn) (SEQ ID NO: 57) (0.5 mmol) and sodium cyanoborohydride (150 mg). Shake for 2 hours and filter. Wash with dimethylformamide (3×2 mL), methylene chloride (3×2 mL) and evaporate the solvent in vacuo to give the title compound.

Step e

Cyclo[AlaΨ[CH$_2$NH]-Arg(N$^g$-Tos)Ψ[COCH$_2$]-Gly-Asp(β-Chxl)-δ-Glu](NHBn)-SEQ ID NO: 59

Treat Boc-AlaΨ[CH$_2$NH]-Arg(N$^g$-Tos)Ψ[COCH$_2$]-Gly-Asp(β-Chxl)-Glu(δ-oxime resin)(NHBn) (SEQ ID NO: 58) (5 mmol) with 25% trifluoroacetic acid in methylene chloride (25 mL) for 25 minutes. Wash with methylene chloride (3×2 mL), isopropanol (3×2 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step g

Cyclo[AlaΨ[CH$_2$NH]-ArgΨ[COCH$_2$]-Gly-Asp-δ-Glu](NHBn)•CF$_3$CO$_2$H-SEQ ID NO: 55

Suspend Cyclo[AlaΨ[CH$_2$NH]-Arg(N$^g$-Tos)Ψ[COCH$_2$]-Gly-Asp(β-Chxl)-δ-Glu](NHBn) (SEQ ID NO: 59) (269 mg) in hydrogen fluoride and anisole. Stir for 1 hour at 0° C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

The following compounds may be prepared by analogous procedures to those described above in Example 14:

Cyclo[D-PheΨ[CH$_2$NH]-ArgΨ[COCH$_2$]-Gly-Asp-δ-Glu]-Leu(NHBn)•TFA;

Cyclo[D-PheΨ[CH$_2$N(C(O)(CH$_2$)$_2$CO$_2$H)]-ArgΨ[COCH$_2$]-Gly-Asp-δ-Glu]-Leu(NHBn)•TFA;

Cyclo[D-PheΨ[CH$_2$N((CH$_2$)$_3$CO$_2$H)]-ArgΨ[COCH$_2$]-Gly-Asp-δ-Glu]-Leu(NHBn)•TFA;

Cyclo[D-PheΨ[CH$_2$N-Gly-Asp-Ac]-ArgΨ[COCH$_2$]-Gly-Asp-δ-Glu]-Leu(NHBn)•TFA;

Cyclo[D-PheΨ[CH$_2$NH]-ArgΨ[COCH$_2$]-Gly-Asp-δ-Glu]-Asp(NH$_2$)•TFA;

Cyclo[D-PheΨ[CH$_2$N(C(O)(CH$_2$)$_2$CO$_2$H)]-ArgΨ[COCH$_2$]-Gly-Asp-δ-Glu]-Phe(NH$_2$)•TFA;

Cyclo[D-PheΨ[CH$_2$N((CH$_2$)$_3$CO$_2$H)]-ArgΨ[COCH$_2$]-Gly-Asp-δ-Glu]-Trp(NH$_2$)•TFA;

Cyclo[D-TyrΨ[CH$_2$NH]-ArgΨ[COCH$_2$]-Gly-Asp-δ-Glu]-Leu(NHBn)•TFA;

Cyclo[D-TyrΨ[CH$_2$N(C(O)(CH$_2$)$_2$CO$_2$H)]-ArgΨ[COCH$_2$]-Gly-Asp-δ-Glu]-Leu(NHBn)•TFA;

Cyclo[D-TyrΨ[CH$_2$N((CH$_2$)$_3$CO$_2$H)]-ArgΨ[COCH$_2$]-Gly-Asp-δ-Glu]-Leu(NHBn)•TFA;

Cyclo[D-TyrΨ[CH$_2$N-Gly-Asp-Ac]-ArgΨ[COCH$_2$]-Gly-Asp-δ-Glu]-Leu(NHBn)•TFA;

Cyclo[D-TyrΨ[CH$_2$NH]-ArgΨ[COCH$_2$]-Gly-Asp-δ-Glu]-Asp(NH$_2$)•TFA;

Cyclo[D-TyrΨ[CH$_2$N(C(O)(CH$_2$)$_2$CO$_2$H)]-ArgΨ[COCH$_2$]-Gly-Asp-δ-Glu]-Phe(NH$_2$)•TFA;

Cyclo[D-PheΨ[CH$_2$N((CH$_2$)$_3$CO$_2$H)]-ArgΨ[COCH$_2$]-Gly-Asp-δ-Glu]-Trp(NH$_2$)•TFA;

The conformationally restrained peptides of formula 1 wherein X is CH$_2$O can be prepared by one of ordinary skill in the art. A general synthetic procedure for preparing these compounds is set forth in Scheme F. In Scheme F, all substituents are as previously described unless otherwise indicated.

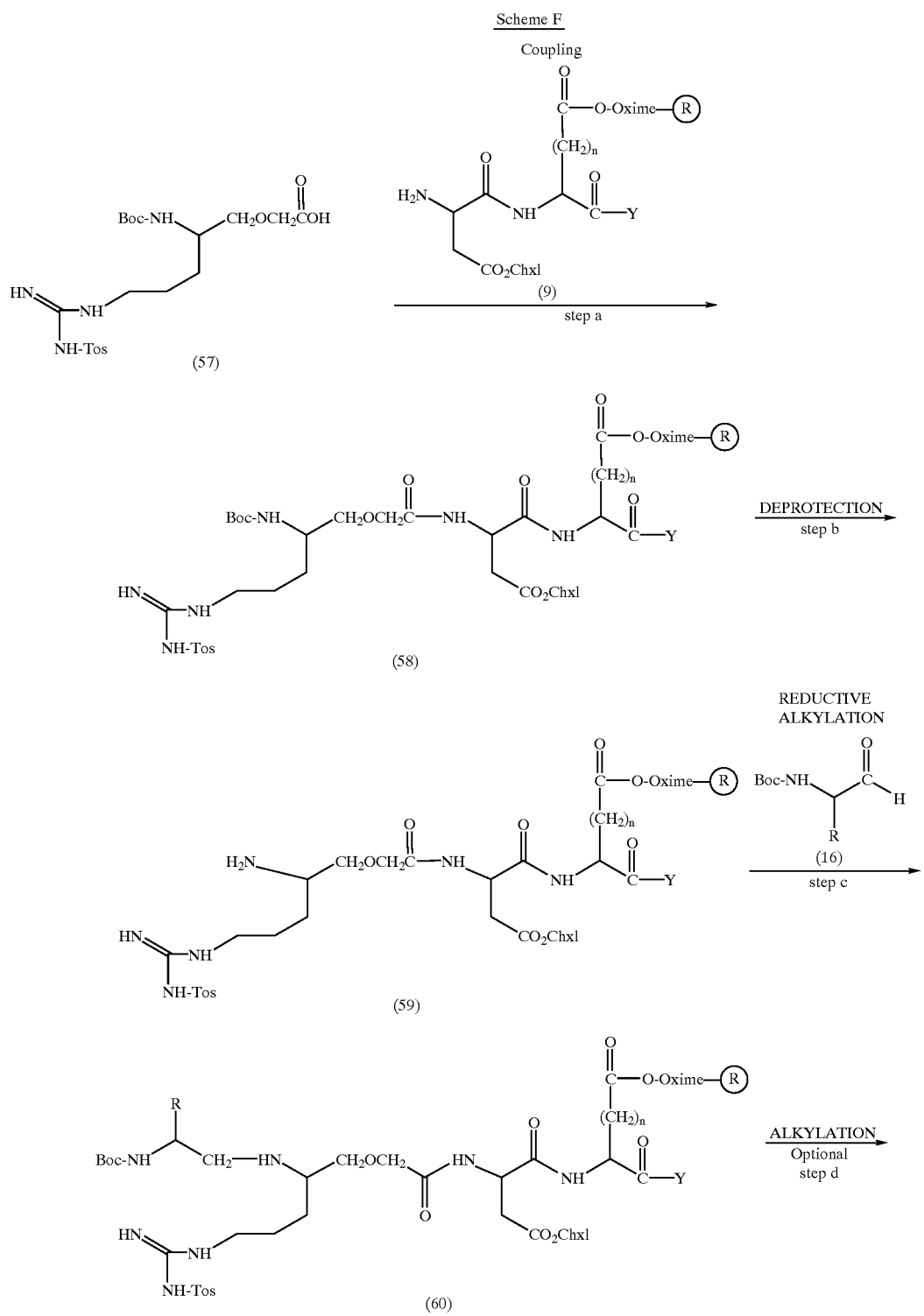

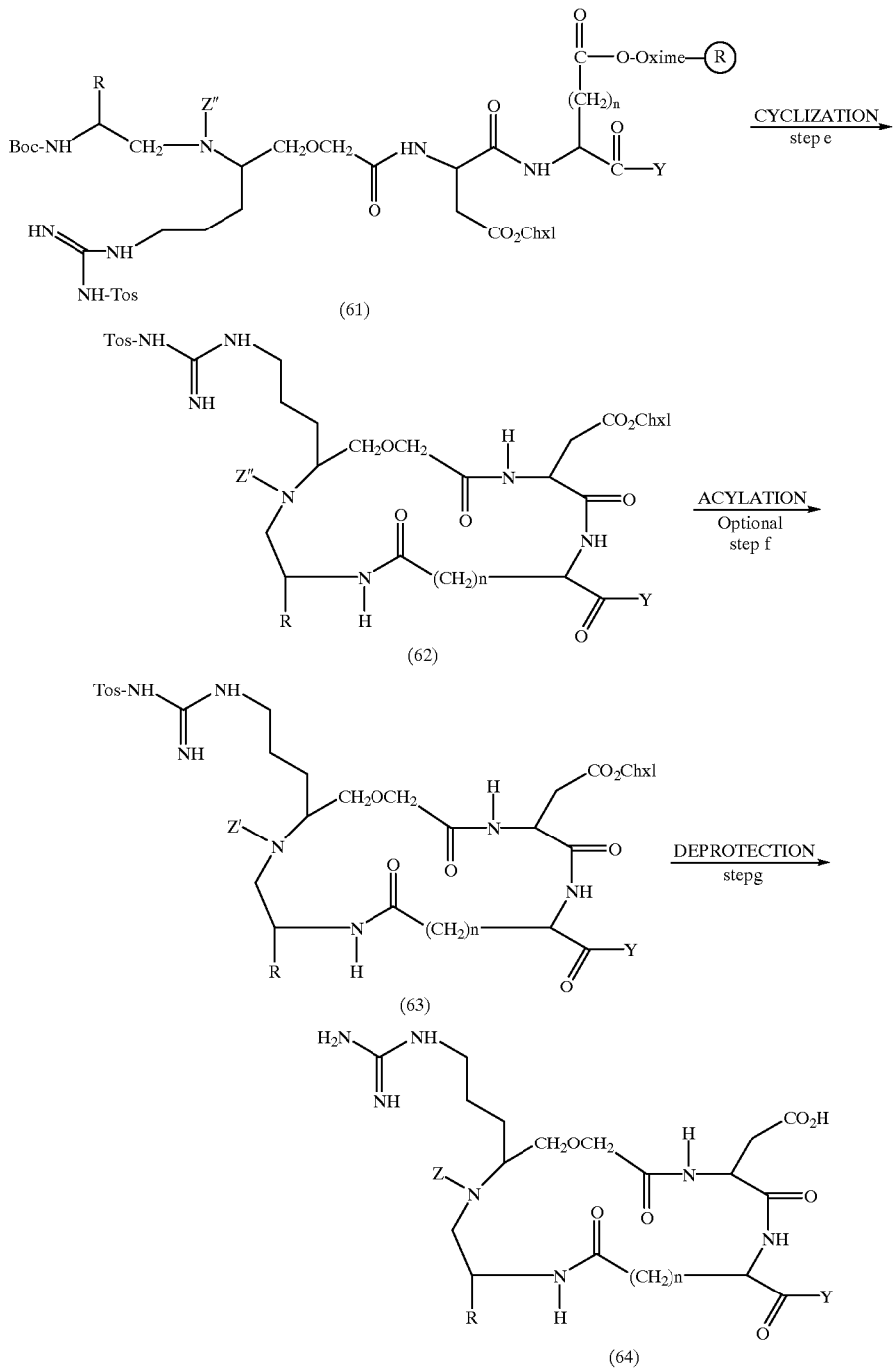

Scheme F provides a general synthetic procedure for preparing the compounds of formula 1 wherein X is $CH_2O$.

In step a, $N^\alpha$-Boc-Arg($N^g$-Tos)Ψ[$CH_2O$]-Gly (57) is coupled with the appropriate Asp(β-Chxl)-amino acid amide oxime resin of structure (9) to give the corresponding $N^\alpha$-Boc-Arg($N^g$-Tos)Ψ[$CH_2O$]-Gly-Asp(β-Chxl)-amino acid amide oxime resin of structure (58) as described previously in Scheme C, step c.

In step b, the $N^\alpha$-Boc protecting group of the appropriate $N^\alpha$-Boc-Arg($N^g$-Tos)Ψ[$CH_2O$]-Gly-Asp(β-Chxl)-amino acid amide oxime resin of structure (58) is cleaved to give the corresponding Arg($N^g$-Tos)Ψ[$CH_2O$]-Gly-Asp(β-Chxl)- amino acid amide oxime resin of structure (59) as described previously in Scheme A, step f.

In step c, the appropriate Arg($N^g$-Tos)Ψ[$CH_2O$]-Gly-Asp (β-Chxl)-amino acid amide oxime resin of structure (59) is coupled with the appropriate D or L-N-Boc-NHCHR-aldehyde of structure (16) to give the corresponding N-Boc-NHCHR-Ψ[$CH_2NH$]-Arg($N^g$-Tos)Ψ[$CH_2O$]-Gly-Asp(β-Chxl)-amino acid amide oxime resin of structure (60) as described previously in Scheme A, step k.

In optional step d, the N-Boc-NHCHR-Ψ[$CH_2NH$] functionality of the appropriate N-Boc-NHCHR-Ψ[$CH_2NH$]-Arg($N^g$-Tos)Ψ[$CH_2O$]-Gly-Asp(β-Chxl)-amino acid amide oxime resin of structure (60) may be alkylated to give the corresponding N-Boc-NHCHR-Ψ[$CH_2N(Z")$]-Arg($N^g$-Tos)Ψ[$CH_2O$]-Gly-Asp(β-Chxl)-amino acid amide oxime resin of structure (61) wherein Z" is W—$A_6$—$A_5$—$A_4$— wherein W is $C_1$–$C_{10}$ alkyl, —$(CH_2)_mC_6H_5$ or —$(CH_2)_pCO_2H$ wherein m is an integer 1–3 and p is an integer 1–4 and $A_6$, $A_5$ and $A_4$ are bonds as described previously in Scheme A, optional step l.

In step e, the appropriate N-Boc-NHCHR-Ψ[$CH_2NH$]-Arg($N^g$Tos)Ψ[$CH_2O$]-Gly-Asp(β-Chxl)-amino acid amide oxime resin of structure (60) or N-Boc-NHCHR-Ψ[$CH_2N(Z")$]-Arg($N^g$Tos)Ψ[$CH_2O$]-Gly-Asp(β-Chxl)-amino acid amide oxime resin of structure (61) wherein Z" is W—$A_6$—$A_5$—$A_4$— wherein W is $C_1$–$C_{10}$ alkyl, —$(CH_2)_mC_6H_5$ or —$(CH_2)_pCO_2H$ wherein m is an integer 1–3 and p is an integer 1–4 and $A_6$, $A_5$ and $A_4$ are bonds is cyclized to give the corresponding Cyclo[NHCHR-Ψ[$CH_2N(Z")$]-Arg($N^g$-Tos)Ψ[$CH_2O$]-Gly-Asp(β-Chxl)-amino acid] amide of structure (62) wherein Z" is W—$A_6$—$A_5$—$A_4$— wherein W is hydrogen, $C_1$–$C_{10}$ alkyl, —$(CH_2)_mC_6H_5$ or —$(CH_2)_pCO_2H$ wherein m is an integer 1–3 and p is an integer 1–4 and $A_6$, $A_5$ and $A_4$ are bonds as described previously in Scheme A, step m.

In optional step f, the appropriate Cyclo[NHCHR-Ψ[$CH_2N(Z")$]-Arg($N^g$-Tos)Ψ[$CH_2O$]-Gly-Asp(β-Chxl)-amino acid] amide of structure (62) wherein Z" is W—$A_6$—$A_5$—$A_4$— wherein W is hydrogen and $A_6$, $A_5$ and $A_4$ are bonds may be acylated as is known in the art to give the corresponding Cyclo[NHCHR-Ψ[$CH_2N(Z')$]-Arg($N^g$-Tos)Ψ[$CH_2O$]-Gly-Asp(β-Chxl)-amino acid] amide of structure (63) wherein Z' is W—$A_6$—$A_5$—$A_4$— wherein W is $C_1$–$C_{10}$ acyl or succinyl and $A_6$, $A_5$ and $A_4$ are bonds.

In addition, the appropriate Cyclo[NHCHR-Ψ[$CH_2N(Z")$]-Arg($N^g$-Tos)Ψ[$CH_2O$]-Gly-Asp(β-Chxl)-amino acid] amide of structure (62) wherein Z" is W—$A_6$—$A_5$—$A_4$— wherein W is hydrogen and $A_6$, $A_5$ and $A_4$ are bonds may be converted to the corresponding Cyclo[NHCHR-Ψ[$CH_2N(Z')$]-Arg($N^g$-Tos)Ψ[$CH_2O$]-Gly-Asp(β-Chxl)-amino acid] amide of structure (63) wherein Z' is W—$A_6$—$A_5$—$A_4$— wherein W is hydrogen and at least one of $A_6$, $A_5$ and $A_4$ is an amino acid by standard peptide chemistry as is known in the art. The terminal amino of the peptide side chain $A_6$—$A_5$—$A_4$ may then be acylated as is known in the art to give the corresponding Cyclo[NHCHR-Ψ[$CH_2N(Z')$]-Arg($N^g$-Tos)Ψ[$CH_2O$]-Gly-Asp(β-Chxl)-amino acid] amide of structure (63) wherein Z' is W—$A_6$—$A_5$—$A_4$— wherein W is $C_1$–$C_{10}$ acyl or succinyl and at least one of $A_6$, $A_5$ and $A_4$ is an amino acid.

In step g, the protecting groups of the appropriate Cyclo [NHCHR-Ψ[$CH_2N(Z")$]-Arg($N^g$-Tos)Ψ[$CH_2O$]-Gly-Asp (β-Chxl)-amino acid] amide of structure (62) wherein Z" is W—$A_6$—$A_5$—$A_4$— wherein W is hydrogen, $C_1$–$C_{10}$ alkyl, —$(CH_2)_mC_6H_5$ or —$(CH_2)_pCO_2H$ wherein m is an integer 1–3 and p is an integer 1–4 and $A_6$, $A_5$ and $A_4$ are bonds or the appropriate Cyclo[NHCHR-Ψ[$CH_2N(Z)$]-Arg($N^g$-Tos) Ψ[$CH_2O$]-Gly-Asp(β-Chxl)-amino acid] amide of structure (63) wherein Z' is W—$A_6$—$A_5$—$A_4$— wherein W is hydrogen, $C_1$–$C_{10}$ acyl or succinyl and at least one of $A_6$, $A_5$ and $A_4$ is an amino acid are removed to give the corresponding Cyclo[NHCHR-Ψ[$CH_2N(Z)$]-ArgΨ[$CH_2O$]-Gly-Asp-amino acid] amide of structure (64) as described previously in Scheme A, step o.

Starting materials for use in Scheme F are readily available to one of ordinary skill in the art.

The following example presents a typical synthesis as described above in Scheme F. This example is understood to be illustrative only and is not intended to limit the scope of the present invention in any way.

EXAMPLE 15

Cyclo[AlaΨ[$CH_2NH$]-ArgΨ[$CH_2O$]-Gly-Asp-δ-Glu]-(NHBn)·$CF_3CO_2H$-SEQ ID NO: 60

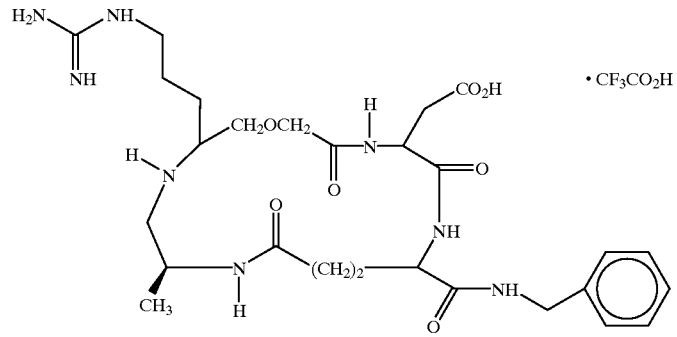

Step a $N^α$-Boc-Arg($N^g$-Tos)Ψ[$CH_2O$]-Gly-Asp(β-Chxl)-Glu(δ-oxime resin)(NHBn)-SEQ ID NO: 61

Suspend $N^α$-Boc-$N^g$-Tos arginine (10 g) in anhydrous tetrahydrofuran (80 mL) and cool to 0–5° C. Add 1,1'-carbonyldiimidazole (3.61 g) all at once and continue stirring for 20 minutes. Immerse in a dry ice/acetone bath to maintain a temperature of −20° to −30° C. Add, by dropwise addition, a suspension of lithium aluminum hydride (1.8 g in 80 mL of tetrahydrofuran) over 45 minutes. Stir an additional 30 minutes at −20° C., quench with the dropwise addition of 2N hydrochloric acid (63 mL) at −10° C. Filter and evaporate the solvent in vacuo to give $N^α$-Boc-$N^g$-Tos argininol.

Dissolve $N^α$-Boc-$N^g$-Tos argininol (70.5 mmol) in acetone (500 mL) and treat with potassium carbonate (10.7 g, 77.6 mmol), potassium iodide (1.17 g, 7.05 mmol) and ethyl bromoacetate (77.6 mmol). Reflux for several hours, cool, filter and evaporate the solvent in vacuo. Purify by flash chromatography to give $N^\alpha$-Boc-Arg($N^g$-Tos)Ψ[$CH_2O$]-Gly(OEt).

Dissolve $N^\alpha$-Boc-Arg($N^g$-Tos)Ψ[$CH_2O$]-Gly(OEt) (20 mmol) in methanol (40 mL). Add 1N lithium hydroxide (25 ml, 20 mmol) and stir under an argon atmosphere for 3.5 hours. Acidify with 1N hydrochloric acid (25 mL), saturate with sodium chloride and extract with ethyl acetate (3×25 mL). Combine the organic phases, dry ($MgSO_4$) and evaporate the solvent in vacuo to give $N^\alpha$-Boc-Arg($N^g$-Tos)Ψ[$CH_2O$]-Gly.

Mix Asp(β-Chxl)-Glu(δ-oxime resin)(NHBn) (10 mmol), $N^\alpha$-Boc-Arg($N^g$-Tos)Ψ[$CH_2O$]-Gly (5.3 mmol), hydroxybenztriazole (1.65 g, 11 mmol) and 1-(3-dimethylaminopropyl)-3-ethyl carbodiimide hydrochloride (2.1 g, 11 mmol). Add a solution of diisopropylethylamine (3.8 mL) in methylene chloride (20 mL) and stir at room temperature for several hours. Briefly wash two times with 50 mL of a solution of 1% diisopropylethylamine in methylene chloride and filter to give the title compound.

Step b
Arg($N^g$-Tos)Ψ[$CH_2O$]-Gly-Asp(β-Chxl)-Glu(δ-oxime resin)(NHBn)-SEQ ID NO: 62

Briefly wash $N^\alpha$-Boc-Arg($N^g$-Tos)Ψ[$CH_2O$]-Gly-Asp(β-Chxl)-Glu(δ-oxime resin)(NHBn) (SEQ ID NO: 61) (2 mmol) with 50 mL of a solution of 25% trifluoroacetic acid in methylene chloride with 1% anisole and filter. Treat with 50 mL of a solution of 25% trifluoroacetic acid in methylene chloride with 1% anisole, stir for 25 minutes and filter. Briefly wash three times with methylene chloride (50 mL) and filter. Briefly wash three times with isopropanol (50 mL) and filter. Briefly wash two times with 50 mL of a solution of 1% diisopropylethylamine in methylene chloride and filter to give the title compound.

Step c
Boc-AlaΨ[$CH_2NH$]-Arg($N^g$-Tos)Ψ[$CH_2O$]-Gly-Asp(β-Chxl)-Glu(δ-oxime resin)(NHBn)-SEQ ID NO: 63

Dissolve Boc-Ala-al (5 mmol) in a solution of 1% acetic acid in dimethylformamide (10 mL). Add Arg($N^g$-Tos)Ψ[$CH_2O$]-Gly-Asp(β-Chxl)-Glu(δ-oxime resin)(NHBn) (SEQ ID NO: 62) (0.5 mmol) and sodium cyanoborohydride (150 mg). Shake for 2 hours and filter. Wash with dimethylformamide (3×20 mL), methylene chloride (3×20 mL) and evaporate the solvent in vacuo to give the title compound.

Step e
Cyclo[(AlaΨ[$CH_2NH$]-Arg($N^g$-Tos)Ψ[$CH_2O$]-Gly-Asp(β-Chxl)-δ-Glu](NHBn)-SEQ ID NO: 64

Treat Boc-AlaΨ[$CH_2NH$]-Arg($N^g$-Tos)Ψ[$CH_2O$]-Gly-Asp(β-Chxl)-Glu(δ-oxime resin)(NHBn) (SEQ ID NO: 63) (5 mmol) with 25% trifluoroacetic acid in methylene chloride (25 mL) for 25 minutes. Wash with methylene chloride (3×20 mL), isopropanol (3×20 mL), methylene chloride (20 mL), 1% diisopropylethylamine in methylene chloride (2×25 mL) and methylene chloride (25 mL).

Suspend in a solution of 1% acetic acid in dimethylformamide and shake for 2 days. Filter and wash with dimethylformamide. Evaporate the solvent in vacuo and dissolve the residual oil in acetic acid. Lyophillize to give the title compound.

Step g
Cyclo[AlaΨ[$CH_2NH$]-ArgΨ[$CH_2O$]-Gly-Asp-δ-Glu]-(NHBn)•$CF_3CO_2H$-SEQ ID NO: 60

Suspend Cyclo[AlaΨ[$CH_2NH$]-Arg($N^g$-Tos)Ψ[$CH_2O$]-Gly-Asp(β-Chxl)-δ-Glu](NHBn) (SEQ ID NO: 64) (269 mg) in hydrogen fluoride and anisole. Stir for 1 hour at 0°

C. Allow the solvent to evaporate and extract into 30% aqueous acetic acid. Lyophillize to give the title compound (232 mg) and purify by Reverse phase-HPLC (aqueous trifluoroacetic acid/acetonitrile) to give the title compound.

The following compounds may be prepared by analogous procedures to those described above in Example 15:

Cyclo[D-PheΨ[$CH_2NH$]-ArgΨ[$CH_2O$]-Gly-Asp-δ-Glu]-Leu(NHBn)•TFA;

Cyclo[D-PheΨ[$CH_2N(C(O)(CH_2)_2CO_2H)$]-ArgΨ[$CH_2O$]-Gly-Asp-δ-Glu]-Leu(NHBn)•TFA;

Cyclo[D-PheΨ[$CH_2N((CH_2)_3CO_2H)$]-ArgΨ[$CH_2O$]-Gly-Asp-δ-Glu]-Leu(NHBn)•TFA;

Cyclo[D-PheΨ[$CH_2$N-Gly-Asp-Ac]-ArgΨ[$CH_2O$]-Gly-Asp-δ-Glu]-Leu(NHBn)•TFA;

Cyclo[D-PheΨ[$CH_2NH$]-ArgΨ[$CH_2O$]-Gly-Asp-δ-Glu]—Asp($NH_2$)•TFA;

Cyclo[D-PheΨ[$CH_2N(C(O)(CH_2)_2CO_2H)$]-ArgΨ[$CH_2O$]-Gly-Asp-δ-Glu]-Phe($NH_2$)•TFA;

Cyclo[D-PheΨ[$CH_2N((CH_2)_3CO_2H)$]-ArgΨ[$CH_2O$]-Gly-Asp-δ-Glu]-Trp($NH_2$)•TFA;

Cyclo[D-TyrΨ[$CH_2NH$]-ArgΨ[$CH_2O$]-Gly-Asp-δ-Glu]-Leu(NHBn)•TFA;

Cyclo[D-TyrΨ[$CH_2N(C(O)(CH_2)_2CO_2H)$]-ArgΨ[$CH_2O$]-Gly-Asp-δ-Glu]-Leu(NHBn)•TFA;

Cyclo[D-Tyr•[$CH_2N((CH_2)_3CO_2H)$]-ArgΨ[$CH_2O$]-Gly-Asp-δ-Glu]-Leu(NHBn)•TFA;

Cyclo[D-TyrΨ[$CH_2$N-Gly-Asp-Ac]-ArgΨ[$CH_2O$]-Gly-Asp-δ-Glu]-Leu(NHBn)•TFA;

Cyclo[D-TyrΨ[$CH_2NH$]-ArgΨ[$CH_2O$]-Gly-Asp-δ-Glu]-Asp($NH_2$)•TFA;

Cyclo[D-TyrΨ[$CH_2N(C(O)(CH_2)_2CO_2H)$]-ArgΨ[$CH_2O$]-Gly-Asp-δ-Glu]-Phe($NH_2$)•TFA;

Cyclo[D-PheΨ[$CH_2N((CH_2)_3CO_2H)$]-ArgΨ[$CH_2O$]-Gly-Asp-δ-Glu]-Trp($NH_2$)•TFA.

The antiplatelet dose of a peptide analog of this invention is from 0.2 mg/kg to 250 mg/kg of patient body weight per day depending on the patient, the severity of the thrombotic condition to be treated and the peptide analog selected. The suitable dose for a particular patient can be readily determined. Preferably from 1 to 4 daily doses would be administered typically with from 5 mg to 100 mg of active compound per dose.

Antiplatelet therapy is indicated for the prevention or recurrence of myocardial infarction and stroke, as well as other disease conditions associated with platelet aggregation. Those experienced in this field are readily aware of the circumstances requiring anticoagulant and antiplatelet therapy. The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; by application to the mucous membranes, such as, that of the nose, throat and bronchial tubes, for example, in an aerosol can containing a peptide derivative of this invention in a spray or dry powder form, or transdermally.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The efficacy of the compounds of this invention to act as antithrombotic and antiplatelet aggregation agents can be demonstrated using standard art recognized tests. Applicants have determined the relevant activities for the representative compounds of Table I by the procedures outlined in Example 16 and the results are tabulated in Table II.

TABLE I

COMPOUNDS EVALUATED FOR ANTIPLATELET AND ANTITHROMBOTIC ACTIVITY

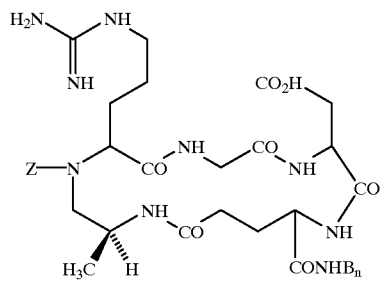

| Test Compound # | Z |
|---|---|
| I | H |
| II | HOC(=O)(CH$_2$)$_3$— |
| III | H$_2$N(CH$_2$)$_2$C(=O)— |
| IV | C$_6$H$_5$—(CH$_2$)$_3$— |

TABLE II

ANTIPLATELET AND ANTITHROMBOTIC ACTIVITY OF VARIOUS FORMULA I COMPOUNDS

| Test Compound # | $^{125}$I-Fibrinogen Binding to Platelets IC$_{50}$ ($\mu$M) | Platelet Aggregation ADP Induced IC$_{50}$ ($\mu$M) | GPIIbIIIa (Fibrogen ELISA IC$_{50}$ ($\mu$M) | Cyclic Flow Reduction mg/min |
|---|---|---|---|---|
| I | 2.4 | — | 0.20 | 0.3 |
| II | 1.2 | — | 0.54 | 0.01 |
| III | 2.4 | 49.2 | 3.0 | 0.1 |
| IV | 0.27 | 6.4 | 0.3 | 0.3 |

EXAMPLE 16

Determination of antiplatelet and antithrombotic activity

Experimental Animals

Male Sprague-Dawley rats (300–400 gm) purchased from Harlan Sprague Dawley, Inc., (Indianapolis, Ind. 46229) were used in these studies.

Blood Sampling

Blood samples were drawn into plastic syringes containing 3.8% trisodium citrate (1:10, V:V). Plasma was prepared by centrifugation at 2,000×g for 10 min. Venous blood for in vitro studies was collected from healthy, drug free, male volunteers.

Coagulation Assays

Activated partial thromboplastin time (aPTT) determinations were carried out using the reagents and methods of Dade Diagnostics, Inc., (Aguada, Puerto Rico 00602).

Thrombin clotting times were determined by incubating 0.1 ml of rat plasma at 37° C. with 0.1 ml of 0.1M Tris buffer, pH 7.5 for 30 seconds. Coagulation was started with 0.1 ml of bovine thrombin (Sigma Diagnostics, St. Louis, Mo. 63178) solution (12 NIH units/ml). All clotting times were measured semiautomatically using a MLA-Electra 750, MLA, Inc. (Pleasantville, N.Y. 10570). The concentration required for doubling the clotting time ($ID_2$) was calculated using simple linear regression.

Platelet Aggregation In Vitro

Human platelet rich plasma (PRP) was prepared by centrifugation at 200×g for 10 min. at room temperature. Platelet poor plasma (PPP) was prepared by centrifugation at 2000×g for 10 min. PRP was exposed only to plastic laboratory ware. All experiments were completed within 3 hr of blood collection. Platelet aggregation was measured photometrically using a Chrono-log dual channel aggregometer (Chrono-log Corp., Haverstown, Pa. 19083). One hundred percent light transmission was defined with autologus PPP. Percent maximal change in light transmission was determined from PRP following addition of ADP ($1 \mu M$) or thrombin. Thrombin (0.2–2.0 Units/ml)-induced platelet aggregation was concentration dependent and the half-maximal concentration used for inhibition studies. MDL 102,530 was incubated with PRP (0.45 ml) for 30 sec prior to the addition of ADP or thrombin. Aggregation was measured in a total volume of 0.5 ml. Inhibitory responses were expressed s percent inhibition when compared to a control value. The concentration resulting in 50% inhibition of aggregation ($IC_{50}$) was calculated by simple linear regression.

Preparation of Human Platelets

Human blood was collected by venipuncture in tubes containing one-tenth volume of acid-citrate-dextrose as an anticoagulant. Platelet-rich plasma was prepared by centrifugation of the blood for 10 min at 500 g at room temperature. The platelet-rich plasma was decanted and one-tenth volume of acid-citrate-dextrose was added followed by centrifugation at 1000 g at room temperature for 10 min to sediment the platelets. The platelets were suspended in two ml modified Tyrode's buffer (2 M NaCl, 0.5 M dextrose, 0.2 M $NaHCO_3$, 0.1 M KCl, 0.1 M $MgCl_2$, 0.1 M $NaH_2PO_4$ and 0.1 M HEPES, pH 7.3) containing 0.35% bovine serum albumin and then filtered on a 50 ml column of Sepharose 2B (Pharmacia) equilibrated with Tyrode's buffer. Finally, the platelets were counted in an automated hematology analyzer.

Platelet Aggregation In Vivo in Anesthetized Dogs

In open-chest anesthetized dogs, left anterior descending coronary arterial (LAD) blood flow, aortic blood pressure, heart rate and EKG were recorded. In the presence of a critical stenosis and endothelial damage of the LAD, LAD coronary arterial flow showed a slow and progressive decrease to near zero followed by a sudden return to near control level which is referred to as a cyclic flow reduction (CFR). Cyclic flow reductions are known to be caused by platelet thrombi formation followed by their dissemination. The antithrombotic activity of these compounds were evaluated in this model by their abilities to abolish CFRs.

Fibrinogen Iodination

Human low solubility fibrinogen (Kabi) was prepared as described previously (Lipinska et al., 1974). For $^{125}I$ labeling, fibrinogen (1 mg) was incubated with three Iodo-Beads (Pierce Chemical Co.) and 1 mCi of $Na^{125}I$ for 15 min after with $^{125}I$-fibrinogen was separated from free radioactivity by filtration through a PD-10 column (Pharmacia). The specific activity was approximately $1-5 \times 10^{17}$ CPM/mol fibrinogen.

Fibrinogen Binding Assay

Binding of fibrinogen to human platelets was performed as described by Plow and Ginsberg (1981). Binding assays contained, in a volume of 0.2 ml, $1-2 \times 10^7$ platelets, $0.1 \mu M$ $^{125}I$-fibrinogen, 2 mM $CaCl_2$ and 0.1 U/ml thrombin or various concentrations of activator peptides as a stimulus. Incubations were carried out in 1.2 ml Eppendorf microcentrifuge tubes at room temperature for 30 min and then duplicate 75 $\mu l$ aliquots were layered onto 0.4 ml of 20% sucrose in Tyrode's buffer containing 1% bovine serum albumin and platelets were sedimented by centrifugation at 10,000 g for 5 min in a Beckman microcentrifuge. Tips of the centrifuge tubes were amputated and bound $^{125}I$-fibrinogen was measured in a gamma counter (LKB/Pharmacia). Nonspecifically bound radioactivity was determined in incubations in which activators were excluded and these values were 1–5% of those obtained with thrombin activation.

GPIIbIIIa Enzyme-Linked Immunoassay

Low solubility fibrinogen, prepared as described by Lipinska et al., *J. Lab. Clin. Med.*, 84, 509–516 (1974) (human, KABI) was immobilized at 5 $\mu g$/well on Immunolon 2-96 well plates (inculated overnight at 4° to bind to the wells). The wells were blocked with 0.5% bovine serum albumin in buffer A (20 nM Tris-HCl, pH 7.5, 2 mM $CaCl_2$, 120 mM CaCl, and 0.02% $NaN_3$) for two hours at room temperature. All subsequent steps were carried out at room temperature. The wells were washed three times with buffer A plus 0.5% Tween 20 (BioRad). Purified GPIIbIIIa (2 $\mu g$/well) plus synthetic peptides supplements at the indicated concentrations were conincubated for 90 to 120 min with immobilized fibrinogen. The wells were washed as above, then the anti-GPIIbIIIa monoclonal antibody, CD41a, was added to each well and incubated for 60 min. After another three washes, goat anti-mouse horseradish peroxidase conjugate was added to each well (60 min). The wells were washed three times with buffer A plus detergent, followed by two washes with buffer A minus detergent. The peroxidase substrate, 3,3',5,5'-tetramethylbenzidine (Kirkegaard and Perry Laboratories, Inc.) was added to the wells for color development. The reaction was stopped with 0.3N $H_2SO_4$, and absorbances were measured at 450 mn using a microplate reader (Multiscan II, Flow-Titertek).

GPIIbIIIa Purification

GPIIbIIIa was purified from human platelets as described by Fitzgerald, et al., *Anal. Biochem.*, 151, 169–177 (1985), except that the final gel purification step was performed with an HW55 size exclusion column (Waters, Advanced Protein Purification System), instead of Sephacryl S-300. The protein, greater than 90% pure as assessed by SDS polyacrylamide gel electrophoresis, was stored at −80° C. in small aliquots.

What is claimed is:

1. A compound of the formula

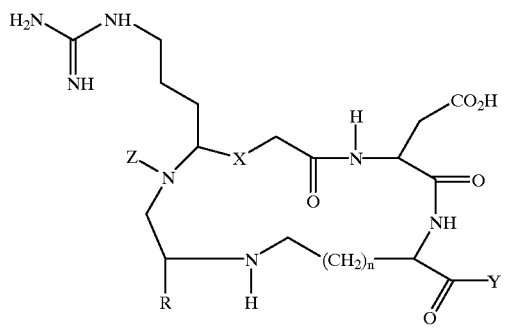

wherein

Y is a fragment —$A_1$—$A_2$—$A_3$—$NR_1R_2$ wherein
$A_1$ is a bond or an amino acid selected from the group consisting of Ser, Asp and Phe; $A_2$ is a bond; $A_3$ is a bond and $R_1$ and $R_2$ are each independently hydrogen, $C_1$–$C_{10}$ alkyl, benzyl, or phenyl optionally substituted with 1 substituent selected from the group consisting of Cl, Br, OH and $OCH_3$;

Z is a fragment W—$A_5$ or $A_4$ wherein
$A_4$ is a bond or an amino acid selected from the group consisting of Gly and βAla; $A_5$ is a bond or is Asp; $A_6$ is a bond and W is hydrogen, succinyl, $C_1$–$C_{10}$ acyl, $C_1$–$C_{10}$ alkyl, —$(CH_2)_mC_6H_5$ wherein m is an integer 1–3, or —$(CH_2)_pCO_2H$ wherein p is an integer 1–4;

X is CONH, $COCH_2$ or $CH_2CH_2$;

R is hydrogen, $CH_3$, benzyl, or p-HO-benzyl; and n is an integer 1–3, with the proviso that when either of $A_6$, $A_5$ and $A_4$ are amino acids, W is not $C_1$–$C_{10}$ alkyl, —$(CH_2)_mC_6H_5$ or —$(CH_2)_pCO_2H$, or a pharmaceutically acceptable salt thereof.

2. A compound of claim 1 wherein Y is benzylamine or Asp-$NH_2$.

3. A compound of claim 1 wherein n is 2.

4. A compound of claim 1 wherein R is $CH_3$, benzyl or p-OH-benzyl.

5. A compound of claim 1 wherein Z is succinyl, —$(CH_2)_3$ $CO_2H$ or $CH_3CO$-Asp-Gly.

6. A compound of claim 1 wherein

Y is benzylamine or Asp-$NH_2$;

n is 2;

R is $CH_3$, benzyl or p-OH-benzyl; and

Z is succinyl, —$(CH_2)_3CO_2H$, or $CH_3CO$-Asp-Gly.

7. A compound of claim 1 which is Cyclo[AlaΨ[$CH_2NH$]-Arg-Gly-Asp-δ-Glu](NHBn)•$CF_3CO_2H$.

8. A compound of claim 1 which is Cyclo[AlaΨ[$CH_2N$(CO($CH_2$)$_2CO_2H$)]-Arg-Gly-Asp-δ-Glu](NHBn)•$CF_3CO_2H$.

9. A compound of claim 1 which is Cyclo[AlaΨ[$CH_2N$(($CH_2$)$_2$Ph)]-Arg-Gly-Asp-δ-Glu](NHBn)•$CF_3CO_2H$.

10. A compound of claim 1 which is Cyclo[AlaΨ[$CH_2N$(($CH_2$)$_3CO_2H$)]-Arg-Gly-Asp-δ-Glu](NHBn)•$CF_3CO_2H$.

11. A method of treating a thrombotic condition in a patient in need thereof which comprises administering to the patient an antiplatelet effective dose of a compound of claim 1.

* * * * *

SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:1:

Xaa Arg Gly Asp Xaa
1               5

(2) INFORMATION FOR SEQ ID NO:2:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:2:

Xaa Gly Xaa Xaa
1

(2) INFORMATION FOR SEQ ID NO:3:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:3:

Xaa Gly Xaa Xaa
1

(2) INFORMATION FOR SEQ ID NO:4:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:4:

Xaa Xaa Gly Xaa Xaa
1               5

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:5:

Xaa Xaa Gly Xaa Xaa
1               5

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:6:

Xaa Arg Gly Asp Xaa
1               5

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:7:

Xaa Xaa Gly Xaa Xaa
1               5

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:8:

Xaa Arg Gly Asp Xaa
1               5

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:9:

Xaa Xaa Gly Xaa Xaa
1               5

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:10:

Xaa Xaa Gly Xaa Xaa
1               5

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:11:

Xaa Arg Gly Asp Xaa
1               5

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:12:

Xaa Xaa Gly Xaa Xaa
1               5

(2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:13:

Xaa Xaa Gly Xaa Xaa
1               5

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:14:

Xaa Arg Gly Asp Xaa
1               5

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:15:

Xaa Xaa Gly Xaa Xaa
1               5

(2) INFORMATION FOR SEQ ID NO:16:

(i) SEQUENCE CHARACTERISTICS:
        (A) LENGTH: 4 amino acids

```
        (B) TYPE: amino acid
        (D) TOPOLOGY: linear (ii) MOLECULE TYPE: peptide (xi) SEQUENCE DESCRIPTION: SEQ ID NO:16:

Xaa Xaa Xaa Xaa
1

(2) INFORMATION FOR SEQ ID NO:17:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:17:

Gly Xaa Xaa Xaa
1

(2) INFORMATION FOR SEQ ID NO:18:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:18:

Xaa Gly Xaa Xaa Xaa
1               5

(2) INFORMATION FOR SEQ ID NO:19:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:19:

Xaa Gly Xaa Xaa Xaa
1               5

(2) INFORMATION FOR SEQ ID NO:20:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:20:

Xaa Xaa Gly Xaa Xaa Xaa
1               5

(2) INFORMATION FOR SEQ ID NO:21:

(i) SEQUENCE CHARACTERISTICS:
        (A) LENGTH: 4 amino acids
        (B) TYPE: amino acid
        (D) TOPOLOGY: linear (ii) MOLECULE TYPE: peptide
```

(xi) SEQUENCE DESCRIPTION: SEQ ID NO:21:

Xaa Xaa Xaa Xaa
1

(2) INFORMATION FOR SEQ ID NO:22:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:22:

Gly Xaa Xaa Xaa
1

(2) INFORMATION FOR SEQ ID NO:23:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:23:

Xaa Gly Xaa Xaa Xaa
1               5

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:24:

Xaa Gly Xaa Xaa Xaa
1               5

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:25:

Xaa Xaa Gly Xaa Xaa Xaa
1               5

(2) INFORMATION FOR SEQ ID NO:26:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:26:

Xaa Xaa Xaa Xaa (2) INFORMATION FOR SEQ ID NO:27:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:27:

Gly Xaa Xaa Xaa
1

(2) INFORMATION FOR SEQ ID NO:28:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:28:

Xaa Gly Xaa Xaa Xaa
1               5

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:29:

Xaa Gly Xaa Xaa Xaa
1               5

(2) INFORMATION FOR SEQ ID NO:30:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:30:

Xaa Xaa Gly Xaa Xaa Xaa
1               5

(2) INFORMATION FOR SEQ ID NO:31:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:31:

Xaa Xaa Xaa Xaa
1

(2) INFORMATION FOR SEQ ID NO:32:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:32:

Gly Xaa Xaa Xaa
1

(2) INFORMATION FOR SEQ ID NO:33:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:33:

Xaa Gly Xaa Xaa Xaa
1               5

(2) INFORMATION FOR SEQ ID NO:34:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:34:

Xaa Gly Xaa Xaa Xaa
1               5

(2) INFORMATION FOR SEQ ID NO:35:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO:35:

Xaa Xaa Gly Xaa Xaa Xaa
1               5

(2) INFORMATION FOR SEQ ID NO:36:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (xi) SEQUENCE DESCRIPTION: SEQ ID NO:36:

Xaa Xaa Gly Asp Xaa
1               5

(2) INFORMATION FOR SEQ ID NO:37:

(i) SEQUENCE CHARACTERISTICS:
            (A) LENGTH: 4 amino acids
            (B) TYPE: amino acid (D) TOPOLOGY: linear (ii) MOLECULE TYPE: peptide (xi) SEQUENCE DESCRIPTION: SEQ ID NO:37:

Xaa Gly Xaa Xaa
1

(2) INFORMATION FOR SEQ ID NO:38:

(i) SEQUENCE CHARACTERISTICS:
           (A) LENGTH: 4 amino acids
           (B) TYPE: amino acid
           (D) TOPOLOGY: linear (ii) MOLECULE TYPE: peptide (xi) SEQUENCE DESCRIPTION: SEQ ID NO:38:

Xaa Gly Xaa Xaa
1

(2) INFORMATION FOR SEQ ID NO:39:

(i) SEQUENCE CHARACTERISTICS:
           (A) LENGTH: 4 amino acids
           (B) TYPE: amino acid
           (D) TOPOLOGY: linear (ii) MOLECULE TYPE: peptide (xi) SEQUENCE DESCRIPTION: SEQ ID NO:39:

Xaa Gly Xaa Xaa
1

(2) INFORMATION FOR SEQ ID NO:40:

(i) SEQUENCE CHARACTERISTICS:
           (A) LENGTH: 5 amino acids
           (B) TYPE: amino acid
           (D) TOPOLOGY: linear (ii) MOLECULE TYPE: peptide (xi) SEQUENCE DESCRIPTION: SEQ ID NO:40:

Xaa Xaa Gly Xaa Xaa
1               5

(2) INFORMATION FOR SEQ ID NO:41:

(i) SEQUENCE CHARACTERISTICS:
           (A) LENGTH: 5 amino acids
           (B) TYPE: amino acid
           (D) TOPOLOGY: circular (ii) MOLECULE TYPE: peptide (xi) SEQUENCE DESCRIPTION: SEQ ID NO:41:

Xaa Xaa Gly Xaa Xaa
1               5

(2) INFORMATION FOR SEQ ID NO:42:

(i) SEQUENCE CHARACTERISTICS:
           (A) LENGTH: 5 amino acids
           (B) TYPE: amino acid
           (D) TOPOLOGY: circular (ii) MOLECULE TYPE: peptide (xi) SEQUENCE DESCRIPTION: SEQ ID NO:42:

Xaa Xaa Gly Asp Xaa
1               5

(2) INFORMATION FOR SEQ ID NO:43:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (xi) SEQUENCE DESCRIPTION: SEQ ID NO:43:

Xaa Xaa Gly Xaa Xaa
1               5

(2) INFORMATION FOR SEQ ID NO:44:

(i) SEQUENCE CHARACTERISTICS:
         (A) LENGTH: 5 amino acids
         (B) TYPE: amino acid
         (D) TOPOLOGY: circular (ii) MOLECULE TYPE: peptide (xi) SEQUENCE DESCRIPTION: SEQ ID NO:44:

Xaa Xaa Gly Xaa Xaa
1               5

(2) INFORMATION FOR SEQ ID NO:45:

(i) SEQUENCE CHARACTERISTICS:
         (A) LENGTH: 5 amino acids
         (B) TYPE: amino acid
         (D) TOPOLOGY: circular (ii) MOLECULE TYPE: peptide (xi) SEQUENCE DESCRIPTION: SEQ ID NO:45:

Xaa Xaa Gly Asp Xaa
1               5

(2) INFORMATION FOR SEQ ID NO:46:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:46:

Xaa Gly Xaa Xaa
1

(2) INFORMATION FOR SEQ ID NO:47:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:47:

Xaa Gly Xaa Xaa
1

(2) INFORMATION FOR SEQ ID NO:48:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:48:

Xaa Xaa Gly Xaa Xaa
1               5

(2) INFORMATION FOR SEQ ID NO:49:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:49:

Xaa Xaa Gly Xaa Xaa
1               5

(2) INFORMATION FOR SEQ ID NO:50:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:50:

Xaa Xaa Gly Asp Xaa
1               5

(2) INFORMATION FOR SEQ ID NO:51:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:51:

Xaa Gly Xaa Xaa
1

(2) INFORMATION FOR SEQ ID NO:52:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:52:

Xaa Gly Xaa Xaa
1

(2) INFORMATION FOR SEQ ID NO:53:

```
    (i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:53:

Xaa Xaa Gly Xaa Xaa
1               5

(2) INFORMATION FOR SEQ ID NO:54:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:54:

Xaa Xaa Gly Xaa Xaa
1               5

(2) INFORMATION FOR SEQ ID NO:55:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:55:

Xaa Xaa Gly Asp Xaa
1               5

(2) INFORMATION FOR SEQ ID NO:56:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:56:

Xaa Gly Xaa Xaa
1

(2) INFORMATION FOR SEQ ID NO:57:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:57:

Xaa Gly Xaa Xaa
1

(2) INFORMATION FOR SEQ ID NO:58:

(i) SEQUENCE CHARACTERISTICS:
        (A) LENGTH: 5 amino acids
        (B) TYPE: amino acid
        (D) TOPOLOGY: linear
```

(ii) MOLECULE TYPE: peptide (xi) SEQUENCE DESCRIPTION: SEQ ID NO:58:

Xaa Xaa Gly Xaa Xaa
1               5

(2) INFORMATION FOR SEQ ID NO:59:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (xi) SEQUENCE DESCRIPTION: SEQ ID NO:59:

Xaa Xaa Gly Xaa Xaa
1               5

(2) INFORMATION FOR SEQ ID NO:60:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (xi) SEQUENCE DESCRIPTION: SEQ ID NO:60:

Xaa Xaa Gly Asp Xaa
1               5

(2) INFORMATION FOR SEQ ID NO:61:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:61:

Xaa Gly Xaa Xaa
1

(2) INFORMATION FOR SEQ ID NO:62:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:62:

Xaa Gly Xaa Xaa
1

(2) INFORMATION FOR SEQ ID NO:63:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:63:

```
Xaa Xaa Gly Xaa Xaa
1             5

(2) INFORMATION FOR SEQ ID NO:64:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (xi) SEQUENCE DESCRIPTION: SEQ ID NO:64:

Xaa Xaa Gly Xaa Xaa
1             5
```